(12) United States Patent
Dintzis et al.

(10) Patent No.: US 7,083,959 B2
(45) Date of Patent: *Aug. 1, 2006

(54) THERAPEUTIC SUPPRESSION OF SPECIFIC IMMUNE RESPONSES BY ADMINISTRATION OF OLIGOMERIC FORMS OF ANTIGEN OF CONTROLLED CHEMISTRY

(75) Inventors: Howard M. Dintzis, Baltimore, MD (US); Renee Z. Dintzis, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/757,774

(22) Filed: Jan. 9, 2001

(65) Prior Publication Data

US 2002/0187156 A1    Dec. 12, 2002

Related U.S. Application Data

(63) Continuation of application No. 08/440,331, filed on May 12, 1995, now Pat. No. 6,375,951, and a continuation of application No. 08/440,322, filed on May 12, 1995, now Pat. No. 6,340,460, which is a continuation of application No. 08/391,267, filed on Feb. 21, 1995, now Pat. No. 6,022,544, which is a continuation of application No. 07/808,797, filed on Dec. 17, 1991, now abandoned, which is a continuation-in-part of application No. 07/628,858, filed on Dec. 17, 1990, now abandoned, which is a continuation-in-part of application No. 07/354,710, filed on May 22, 1989, now abandoned, which is a continuation-in-part of application No. 07/248,293, filed on Sep. 21, 1988, now Pat. No. 5,126,131, which is a continuation of application No. 06/869,808, filed on May 29, 1986, now abandoned, which is a continuation of application No. 06/460,266, filed on Jan. 24, 1983, now abandoned.

(51) Int. Cl.
*A61K 39/00* (2006.01)

(52) U.S. Cl. .............................. 435/185.1; 424/193.1; 530/402; 530/403

(58) Field of Classification Search ............. 424/185.1, 424/193.1; 530/402, 403
See application file for complete search history.

(56) References Cited

U.S. PATENT DOCUMENTS

| | | | | |
|---|---|---|---|---|
| 4,191,668 A | * | 3/1980 | Katz | |
| 4,220,565 A | | 9/1980 | Katz | ........................ 525/54.1 |
| 4,222,907 A | | 9/1980 | Katz | ........................ 525/54.1 |
| 4,253,995 A | | 3/1981 | Katz | ........................ 525/54.1 |
| 4,253,996 A | | 3/1981 | Katz | ........................ 525/54.1 |
| 4,276,206 A | | 6/1981 | Katz | ........................ 525/54.1 |
| 4,722,899 A | | 2/1988 | Hamaoka et al. | ......... 435/172.2 |
| 5,126,131 A | | 6/1992 | Dintzis et al. | ................. 424/88 |
| 5,268,454 A | * | 12/1993 | Barstad et al. | ............... 530/403 |
| 5,370,871 A | | 12/1994 | Dintzis et al. | ............ 424/244.1 |

OTHER PUBLICATIONS

Katz et al (1973) Induction of Immunological Tolerance in Bone Marrow—Derived Lymphoxytes of the IgE Antibody Class PNAS 70(10):2776-2780.
Dintzis et al, Inhibition of Anti-DNP Antibody Formation by High Doses of DNP-Polyacrylamide Molecules; Effects of Hapten Density and Hapten Valence, The Journal of Immunology, vol. 135, No. 1, pp. 423-427, Jul. 1985.
Dintzis et al, Molecular Determinants of Immunogenicity: The Immunon Model of Immune Response, Proc. Natl. Acad. Sci. USA, vol. 73, No. 10, pp. 3671-3675, Oct. 1976.
Vogelstein et al, Specific Cellular Stimulation in the Primary Immune Response: A Quantized Model, Proc. Natl. Acad. Sci. USA, vol. 79, pp. 395-399, Jan. 1982.
Dintzis et al, Specific Cellular Stimulation in the Primary Response: Experimental Test of a Quantized Model, Proc. Natl. Acad. Sci. USA, vol. 79, pp. 884-888, Feb. 1982.
Dintzis et al, Studies on the Immunogenicity and Tolerogenicity of T—Independent Atigens, The Journal of Immunology, vol. 131, No. 5, Nov. 1983, pp. 2196-2203.
Fundneberg, H.H., Basic and Clinical Immunology, published 1980, pp. 44-52.

* cited by examiner

*Primary Examiner*—David Saunders
(74) *Attorney, Agent, or Firm*—Pillsbury Winthrop Shaw Pittman LLP

(57) ABSTRACT

The present invention relates to a method of specifically suppressing an undesired immune response in a mammal suffering from such a response. The method comprises:

i) preparing a construct comprising at least one discrete antigenically recognizable moiety corresponding to an antigenic determinant of an antigen causing the undesired immune response bound to a pharmacologically acceptable carrier wherein the number of the moieties bound to the carrier and the spacing of the moieties on the carrier are such that the construct does not elicit an immune response to the moieties but does directly compete with the antigen for receptors on an immunocompetent cell that recognizes the determinant, and thereby the construct specifically suppresses the undesired immune response; and ii) administering the construct to the mammal in an amount such that suppression of the undesired immune response is effected. The invention further relates to constructs suitable for use in the above method and to methods of making same.

21 Claims, 59 Drawing Sheets

+ = PTC-(S-2-(2R,2S-succinyl)-L-Cys
• = PTC-GABA

CONJUGATE PEPUDE SUBSTITUTION DENSITY EQUATION

NO MOLECULES PEPUDE/MOLECULE DEXAMINE $$= \frac{\text{PMOLES PEPTIDE VIA AAA}}{\text{PMOLES DEXAMINE(=BACKBONE) VIA AAA}}$$

- - - - ▶ NON-COVALENTLY LINKED PEPTIDE INCREASES NUMERATOR!

- - - - ▶ LOSS OF DEXAMINE DURING:

- GMBS DERIVITIZATION
- G-25 COLUMN PURIFICATION  ⟶ DECREASES NUMERATOR
- REACTION MIXTURE TRANSFERS

FIG. 12

PENICILLIN

PENICILLOYL

THERAPEUTIC SUPPRESSION OF SPECIFIC IMMUNE RESPONSES BY ADMINISTRATION OF OLIGOMERIC FORMS OF ANTIGEN OF CONTROLLED CHEMISTRY

This application is a continuation of U.S. Patent applications Ser. No. ("U.S. Ser. No.") 08/440,331, filed May 12, 1995, issued as U.S. Pat. No. 6,375,951, on Apr. 23, 2002 and U.S. Ser. No. 08/440,322, filed May 12, 1995, issued as U.S. Pat. No. 6,340,460, on Jan. 22, 2002, which are continuations of U.S. Ser. No. 08/391,267, filed Febr. 21, 1995, issued as U.S. Pat. No. 6,022,544, on Feb. 8, 2000, which is a continuation of U.S. Ser. No. 07/808,797, filed Dec. 17, 1991 (now abandoned) which is a continuation-in-part of U.S. Ser. No. 07/628,858, filed Dec. 17, 1990 (now abandoned), which is a continuation-in-part of U.S. Ser. No. 07/354,710, filed May 22, 1989 (now abandoned), which is a continuation-in-part of U.S. Ser. No. 07/248,293, filed Sep. 21, 1988, issued as U.S. Pat. No. 5,126,131, on Jun. 30, 1992, which is a continuation of U.S. Ser. No. 06/869,808, filed May 29, 1986 (now abandoned), which is a continuation of U.S. Ser. No. 06/460,266, filed Jan. 24, 1983 (now abandoned). Each of the aforementioned applications and patents are explicitly incorporated herein by reference in their entirety and for all purposes.

The invention described herein was made in part in the course of work under a grant or award from the United States Army, No. DAMD 17-86-C-6038.

The present invention relates, in general, to a method of suppressing an undesired immune response and to constructs suitable for use therein.

As a mechanism of self defense, animals have developed a complex set of responses to foreign material, collectively called the immune system. Immune responses are generally advantageous (protective) in nature, however, under certain situations, the animal body produces an immune response that is undesirable. Examples of such undesirable responses include allergic reactions, characterized by the production of IgE antibodies to extrinsic antigens, and autoimmune diseases in which the immune system reacts against self antigens.

During the past few decades, a number of methods have been described for inhibiting, suppressing or "curing" specific immune responses. These methods involve the treatment of animals with different kinds of chemical preparations, the details of which are described below. The immune modification methodology which forms the basis of the present series of applications is based on the premise that the immune system recognizes foreign antigens in the context of physically constrained arrays. In order to stimulate the immune system, arrays must exceed a specific size (or geometry) and have a minimum number of physically accessible epitopes which are identical in nature (minimum valence). Once these two parameters are met or exceeded, the immune system will respond by the production of antibodies (IgM, IgG and/or IgE) by antigen specific B-cells and by the production of T-cell factors and/or activities (T-cell 'help', cytokines, cytoxicity, etc.).

The method to which the present invention relates is based on the finding by Applicants that this system can be manipulated by introducing synthetically derived macromolecular arrays that are "subthreshold" in geometry and/or valence and that are designed to compete with naturally occurring arrays for the suppression of autoimmune and extrinsic allergic responses.

The technology which forms the basis of the invention is derived from the Immunon model of immune response described by Dintzis et al in Proc. Nat'l. Acad. Sci. USA, 73:3671–13675 (1976). That paper discloses the concept of there being a threshold as to the number and spacing of haptens on T-cell independent antigens in order to obtain an immunogenic response. The 1976 paper also discloses that the non-immunogenic polymers are suppressive of the action of immunogenic polymers towards triggering the de novo immune response in non-immunized animals. The suppressive effect of non-immunogenic polymers on the immunogenic response of immunogenic polymers is further described in Proc. Nat'l. Acad. Sci. USA, 79:395, 1982; Proc. Nat'l. Acad. Sci. USA, 79:884, 1982; and J. Immunol., 131:2196, 1983. (See also Dintzis et al, J. Immunol. 135: 423, 1985; Dintzis et al In: Theoretical Immunology, Pt. 1, Vol. II. ed. Perelson, A. S. Addison-Wesley Publishing Co., Reading, Mass. pp 83–103, 1988; Dintzis et al, J. Immunol. 143:1239, 1989; Dintzis et al, Eur. J. Immunol. 70:229, 1990; and Dintzis and Dintzis, Immunol. Reviews No. 115, pp 243–251, 1990).

The earlier applications of the present series include details of studies that were done using experimental paradigms involving T-independent antibody responses which can be assessed by the level of IgM production. The use of size restricted backbones of various types (linear polyacrylamide, dextran, Ficoll, carboxymethyl cellulose, etc.) to suppress IgM antibody production to small molecular weight haptens such as DNP and fluorescein is specifically described. (See Examples 1 to 7 below.) In addition, reference is made in the earlier filings to the use of the present invention to suppress allergies to pollen and auto-immune disease, including multiple sclerosis and myasthemia gravis. The present application includes details of studies relating to T-cell dependent antibody production as well as T-cell responses by themselves. The data presented herein thus further support the applicability of the immune suppression methodology of the earlier filed applications in this series to complex responses involving T-cell dependent antibody production, represented by IgG and IgE. In addition, the present disclosure underscores the desirability of characterizing the suppressive constructs to ensure that they are free from potentially simulatory molecules.

As indicated above, varying chemical preparations reportedly suitable for use in methods of inhibiting immune responses have been the subject of numerous publications. The methods disclosed are apparently based on the "special chemical composition" of the polymeric backbone material used which forms an epitope carrier. The mechanisms by which the observed specific immune suppression occurs, and the specific molecular attributes inferred to bring about the suppression, have been variously ascribed to:

1) chemical composition as determined by the ratios of carbon to hydrogen to oxygen in the carrier material (Dawn et al, J. Immunol. 126:407–413, (1981); Wei et al, Int. Archs. Allergy Appl. Immunol. 85:1–7 (1988)).

2) "unnaturalness" as defined by the use of the "unnatural" D-amino acids, rather than "natural" L-amino acids in synthesizing the polypeptide carrier substance (Katz et al, J. Exp. Med., 134:201–223 (1971); Liu et al, Proc. Natl. Acad. Sci. USA 76:1430–1434 (1979); Liu et al, J. Allergy Clin. Immunol. 66:322–326 (1980));

3) "special" chemical properties, undefined in nature; and 4) ability to increase "specific suppressor cells" in undefined ways. (See specific comments that follow). To the best of Applicants' knowledge, however, no other group has proposed that immune suppression occurs because the suppressive material contains molecules with the proper combination of molecular size and epitope valence and, thus, no other group has taught or even suggested the method to which the present invention relates.

Sehon and coworkers have carried out a number of studies on specific immune suppression, induced by the injection of polymeric molecules composed of epitopes coupled to a polyvinylalcohol (PVA) backbone structure (see, for example, Dawn et al, J. Immunol. 126:407–413 (1981); Wei et al, Int. Archs. Allergy Appl. Immunol. 85:1–7 (1988)). The PVA backbone structure was created by reacting low molecular weight PVA, 14 kDa, with cyanogen bromide to convert some of the hydroxyl groups on the polymer to a reactive form, and coupling those activated hydroxyl groups to amino groups on aliphatic diamine. This reaction was expected by the authors to substitute the PVA polymer molecules with a number of free aliphatic amino groups from the unreacted ends of the diamine adduct. These ends were subsequently substituted with hapten groups to form multiply substituted PVA molecules of molecular weight supposedly almost unchanged from that of the original PVA.

This empirical procedure produced soluble haptenated polymeric material which was suppressive of specific immune responses against the hapten involved. However, in reacting a multiply reactive polymer (cyanogen bromide activated PVA) with an excess of a divalent reactant (ethylenediamine) a very substantial amount of cross-linkage between the polymer molecules occurred with the resulting formation of multiply cross-linked molecules of a wide range of molecular weights. Although Sehon and Lee noted that precipitates formed, and discarded them, they apparently did not take this as an indication that higher molecular weight (and thus potentially stimulatory) polymers were being produced.

When Applicants repeated the published procedures of Sehon et al, they found that a very wide range of cross linked-polymer molecules was produced, with the higher molecular weight material precipitating out of solution. The more soluble amine-substituted PVA which remained in solution, after the precipitated material was discarded, had a molecular weight ranging between approximately 15 kDa and 100 kDa (as shown by analytical ultracentrifuge analysis). This is the range of molecular weights for soluble multivalently hapten substituted polymer molecules which Applicants have defined in the earlier filed applications of this series as suppressive of the immune response, without being stimulatory at any dose.

Since Sehon et al did not consider the possibility of cross-linkage of polymer molecules by the chemistry which they employed, and did not determine the actual molecular weight of the material they produced, it can be inferred that they inadvertently stumbled into the functional range of Applicants' paradigm.

Applicants have, in fact, reported, (Dintzis et al, J. Immunol. 143:1239–1244 (1989)) that higher molecular weight (over 100 kDa) PVA molecules multiply substituted with hapten are immunogenic in vivo and in vitro, giving bell shaped dose response curves. Similar molecules with molecular weights below 100 kDa, however, were found by Applicants to be inhibitory of the immune response, without having stimulatory capacity, as predicted by their paradigm.

Katz and co-workers have described the specific suppression of the immune response to epitopes by treatment with polymer preparations composed of those epitopes coupled to a carrier backbone made of the synthetic polypeptide, poly (D-glutamic acid, D-lysine) or poly(D-Glu,D-Lys) (see, for example, (Katz et al, J. Exp. Med. 134:201–223 (1971); Liu et al, Proc. Natl. Acad. Sci. USA 76:1430–1434 (1979); Liu et al, J. Allergy Clin. Immunol. 66:322–326 (1980)). This polypeptide is a commercially available randomly ordered polymer synthesized from chemically activated forms of the D-amino acids, D-lysine and D-glutamic acid, in the ratio 60:40. Katz has rationalized the findings of immune suppressions caused by the "unnatural" character of the synthetic polypeptide composed of the unusual D-amino acids rather than the usual L-forms of the amino acids, which are found in all protein molecules. This interpretation was apparently supported by the finding that equivalent immune suppression was not observed when the carrier backbone polypeptide was synthesized from the more normal L-amino acids.

The findings of Katz fit well into the Immunon paradigm as illustrated below:

1) The poly(D-Glu,D-Lys) preparation used by Katz as a backbone polymer was obtained from commercial sources, and had average molecular weight of less than 100 kDa (the primary commercial producers, Yeda (in Israel) and Sigma (in St. Louis), have informed Applicants that it is not possible for them to produce such polymers with average molecular weights greater than 70 kDa). Thus, Katz apparently used polymers of molecular weight less than 100 kDa as suppressive backbone material, without realizing the significance of this fortuitous choice of molecular weight.

2) Starting with the highest molecular weight poly(D-Glu, D-Lys) available, approximately 70 kDa from Yeda, Applicants substituted a number of the lysine amino groups with the hapten, fluorescein and found the resulting FLU-poly (D-Glu,D-Lys) to be non-immunogenic, as expected. Examination of the material by HPLC revealed that, as expected, it contained molecules with a wide range of molecular weights, from under 40 kDa to a small amount over 100 kDa. When size fractionated by gel filtration chromatography on Superose CL-6B columns, it was possible to separate out a small amount of material of molecular weight approximately 200 kDa. This higher molecular weight fraction proved to be immunogenic for an immune response against fluorescein in mice. This finding indicates that there is nothing intrinsically suppressive about FLU-poly(D-Glu,D-Lys), but that it can be stimulatory or non-stimulatory, depending on the molecular size.

3) To further test the effect of molecular size, Applicants cross-linked non-immunogenic 70 kDa FLU-poly(D-Glu,D-Lys) molecules with carbodiimide, coupling some carboxyl groups on glutamic acid residues with amino groups on lysine residues to form stable amide bonds. A wide range of molecular weight products resulted. When these were size-fractionated on gel filtration columns, the material with molecular weights well above 100 kDa were immunogenic both in vivo and in vitro, whereas the fractions with molecular weights under 100 kDa was not immunogenic. This again fits the expectations of the Immunon hypothesis, and is not consistent with the interpretations put forth by Katz.

4) Since the mammalian body does not produce enzymes capable of hydrolyzing polypeptides composed solely of D-amino acids, it is to be expected that such polypeptides, whether free or epitope substituted, will not be rapidly degraded in the animal body, and will be long lasting in their effects. However, polypeptides made of the usual L-amino acids can be rapidly hydrolyzed by normal proteolytic enzymes and would not be expected to have sustained effects. This suggests that the properties ascribed by Katz to the "unnatural" nature of the D-amino acid polypeptide are due solely to the resistance to enzymatic breakdown, a characteristic shared by many synthetic and natural polymeric molecules Diener and co-workers have published a number of papers describing the specific suppressive immune effects of epitopes coupled to carboxy-methylcellulose as carrier (see, for example, Diner et al, J. Immunol. 122:1886–1891 (1979)). These have been ascribed by Diener to the special chemical nature of carboxymethyl cellulose, without consideration of the molecular weight of the material. However, Applicants have reported that haptenated preparations of carboxymethyl cellulose of molecular weights under 100 kDa are suppressive for epitopes coupled to them, without being stimulatory at any dose, whereas preparations of molecular weights over 100 kDa are stimulatory at proper doses (Dintzis et al, J. Immunol. 143:1239–1244 (1989)). Apparently, Diener used material of molecular weight predominately under 100 kDa, without realizing the significance that the molecular size of the polymers had on the immune effects of his preparations.

The specific suppressive effect of hapten coupled to polyvinylpyrrolidone (PVP), a material which has been used as a blood substitute has been reported (von Specht et al, Clin. Exp. Immunol. 33:292–297 (1978); Lee et al, Eur. J. Immunol. 11:13–17 (1981)). Other authors have published on similar suppressive effects of haptens coupled to Ficoll (Watanabe et al, J. Immunol. 118:251–255 (1977)), pneumococcal polysaccharides (Borel et al, Nature 261:49–50 (1976); Mitchell et al, Eur. J. Immunol. 2:460–467 (1972)), plant polysaccharides (Moreno et al, Clin. Exp. Immunol. 31:499–511 (1978)); Humphrey, Eur. J. Immunol. 11:212–220 (1981)) or isologous immunoglobulin (Lee et al, J. Immunol. 114:829–842 (1975); Borel et al, Nature 261: 49–50 (1976)). These reports are quite diverse, but do not address the combined effects of the molecular weight of polymer carrier and the epitope valence on the immune response which results from their administration, as Applicants have done. Molecular weight characterization of the epitope-substituted polymer preparations was not done in these published studies. However, the experimental protocols are consistent with the interpretation that the average molecular weights of these preparations was under 100 kDa in all instances.

In general, authors who have reported specific suppressive effects from hapten-coupled polymer preparations have apparently chanced upon preparations which fit Applicants' description of suppressive soluble molecules, namely a substantial number of epitopes coupled to a soluble polymeric carrier of molecular weight less than about 100 kDa. While these conditions may be unwittingly encountered under a variety of circumstances, as noted above, such encounters are not suggestive of the present invention.

BRIEF DESCRIPTION OF THE FIGURES

FIG. 12. Conjugate peptide substitution density equation.

FIG. 52. Suppression of anti-histone antibody titers.

FIGS. 53. Specificity of suppression of anti-histone responses.

DESCRIPTION OF THE INVENTION

Figure 1:
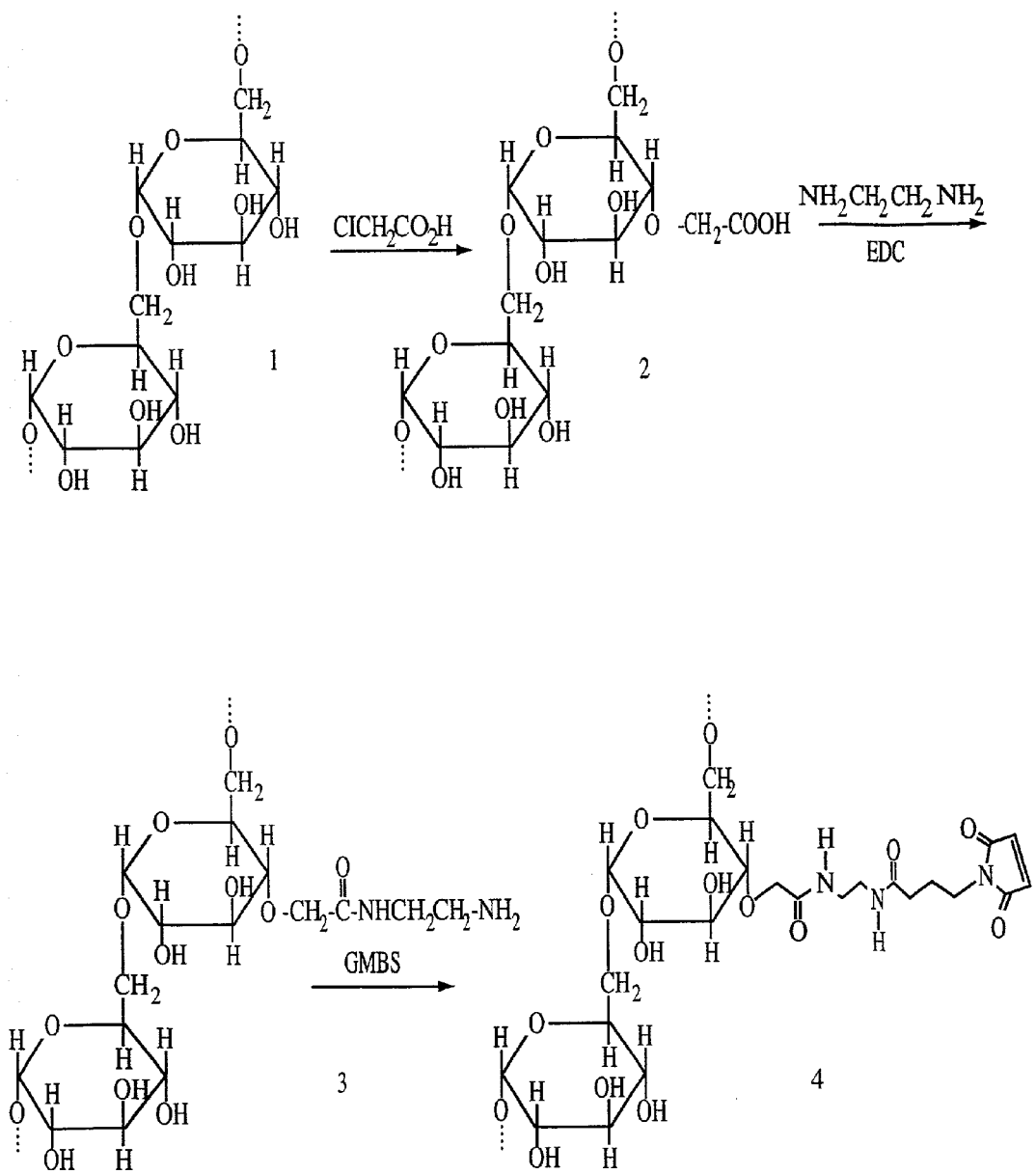
FIG. 1. Conversion of dextran to GMB-dextran.

The method of the invention comprises administering to a subject suffering from an undesired immune response an effective amount of a non-immunogenic material which carries a number of antigenic domains (i.e., "epitopes" or "haptens") which correspond to the antigen, e.g. the allergen or self-antigen which causes the allergy or autoimmune disease responsible for the undesired response. The haptens or epitopes bind to cell antigen receptors specific for the indicated haptens or epitopes and, provided the hapten or epitope number is sufficient and the carrier size is below an ascertainable threshold limit so as to avoid the formation of a stimulatory cluster of antigen receptors, the administered material serves to suppress or abolish the specific immune response. The administered material specifically suppresses the immune response to the allergen or self-antigen, without compromising or damaging the general immune competence of the body.

The disclosure of application Ser. No. 07/248,293, now U.S. Pat. No. 5,126,131, includes a description of constructs comprising size fractionated linear polyacrylamide chemically modified to accept DNP groups as epitopes. These conjugates can be organized into groups based on the size (molecular weight) of the backbone polymer and hapten number (number of DNP groups per average molecular weight polymer for a given group). The combination of these two scalar quantities makes it possible to determine the role of hapten density as a separate variable. Based on the data obtained using these constructs in both in vitro and in vivo models of immune function, certain "rules" governing B-cell activation by antigen have been elucidated and used to control the T-cell independent immune response on an antigen specific basis. These rules and their use in effecting an antigen specific alteration in immune function are included in application Ser. No. 07/248,293, now U.S. Pat. No. 5,126,131.

Application Ser. No. 07/354,710 (now abandoned, from which continuation application Ser. No. 08/049,601, now U.S. Pat. No. 5,370,871, was filed) included further exemplification in support of the application of these rules to include a variety of backbones or scaffolds and haptens, thus further documenting the "universality" of the rules elucidated in the original filing as they apply, particularly, to T-cell independent immune system activities (operationally defined as IgM production). The present disclosure includes specific exemplification which makes clear the applicability of these selfsame rules to a spectrum of immune function, including T-cell dependent antibody production (operationally defined as the production of IgG and IgE) and T-cell activity as well.

The Examples that follow include the exemplification from the parent cases and further exemplification of complex constructs involving antigens of greater diversity than simple small molecular weight haptens such as DNP and fluorescein. The biophysical and biochemical considerations that need to be taken into account when designing these constructs are set forth below. These include the chemistry of synthesis of the constructs and preferred methods of characterizing the final products so as to optimize fidelity to and compliance with the primary principles governing valence and size that constitute the operational underpinnings of the invention as disclosed in this series of applications.

For a construct (conjugate) to be non-stimulatory, and hence "suppressive" or tolerogenic in nature, it must meet one or both of the following criteria:

i) The "valence" of the conjugate (operationally defined as the number of "discrete antigenically recognizable moieties" per final macromolecular construct) must be less than the Immunon model threshold number (generally, less than 20). As noted above, these moieties can be simple haptens or more complex peptides or proteins. It will be appreciated that each of these moieties may have multiple "antigenic facades", but for any given B-cell, capable of recognizing the moiety, it will have one and only one discrete binding region recognized by one immunoglobulin receptor of that particular B-cell even though other B-cells may recognize other regions of the moiety in question. Special cases such as peptides or proteins containing multiple identical peptide sequences (such as some of the sequences found in certain malaria proteins or in proteins such as hemoglobin which has repeated subunits) or carbohydrates with regularly repeating series of sugar residues (such as in bacterial polysaccharides) are considered as containing multiple "discrete antigenically recognized moieties" for purposes of defining valence; and/or ii) The size of the final construct must be smaller than the minimum size necessary for spanning the cluster of receptors defining the "Immunon". It will be appreciated that the effective size will be a function of a number of independent parameters including: geometry of the backbone or scaffold (linear, branched, globular, radial, etc.), the physical nature of the backbone (flexible, rigid, "articulated", etc.), the hydrophilicity or hydrophobicity of the backbone, the electrostatic nature of the conjugate (the sum of charges on both the backbone and the arrayed moiety described above), and the size, geometry and physical make-up of the moiety itself.

It will be appreciated that the optimum number and spacing for a particular hapten or epitope as well as the carrier size can be determined without undue experimentation by simple tests on experimental animals such as mice, rats, rabbits or guinea pigs, using the selected scaffold material and antigenically recognizable moiety (see the above-referenced 1976 paper).

I. Preparation of Immunosuppressive Constructs

Constructs suitable for use in the present invention can be produced using known means. Preferably, the production method used is one which minimizes the possibility of polymerization as well as cross-linking between the individual molecules. In addition, the production method is, preferably, chosen such that only one potential reactive site per arrayed moiety is available so that the orientation of the moiety to the backbone can be controlled. Resulting construct preparations are, advantageously, characterized prior to use to ensure that they are substantially free from high molecular weight, potentially stimulatory molecules. The use of valence restricted scaffolds of defined chemistry is preferred in order to optimize reproducibility of the resulting construct.

Construct Design and Analysis:

A. General Chemistry Considerations

The fundamental concept underlying the technology upon which Applicants' invention is based is that the immune system interacts with its external milieu by the recognition of antigenic arrays of epitopes or haptens. From the biophysical or biochemical perspective, epitopes or haptens are no different from any other receptor ligand, and the soluble immunoglobulin molecules and their membrane bound relatives (such as the T-cell receptor, the B-cell receptor, etc.) are no different than any other protein receptor molecule in other biological systems. The difference lies not with the individual receptor-ligand interaction but with the mechanism of "information transfer" that occurs after the ligand is bound by the receptor. While the individual membrane bound receptors in the immune system can and will bind monovalent ligands, the functional interaction for this type of ligand-receptor interaction is the time stable clustering of receptors into discrete units termed "immunons". This phenomenon differs qualitatively from receptor-ligand interactions in other biological systems wherein each individual binding event has functional importance. (For example: when a single neurotransmitter molecule binds to it receptor on the post-synaptic membrane, a change in membrane potential can be measured.) While immunon formation depends on the binding of individual ligands (epitopes or haptens) with individual receptors, the immunon itself is dependent on the biophysical characteristics of the entire array and not the summation of individual binding events.

A corollary to this discussion of receptor-ligand interaction in the immune system as compared to receptor-ligand interactions in other biological systems is the concept of subthreshold and superthreshold arrays being immunologic "antagonists" and "agonists", respectively. For a classical pharmacologic antagonist to have acceptable potency it must bind to the receptor molecule with approximately the same degree of affinity as an agonist but in a "nonproductive" manner. That is, it must bind but not activate the secondary events caused by agonist binding. Since the functional event in the immune system is immunon formation and not individual receptor-ligand interactions, the corollary to an "antagonist ligand" is the "antagonist array" that can aggregate receptors in nonproductive clusters thereby preventing the formation of an immunon by an "agonist array". Using this concept of productive and nonproductive receptor clustering, immunologic agonists can be viewed as "superthreshold arrays" that can bind with a number of receptors that meets or exceeds the minimum necessary for immunon formation and immunologic antagonists can be viewed as "subthreshold arrays" that cannot induce immunon formation but can still occupy multiple receptors simultaneously with approximately the same degree of aggregate avidity as the superthreshold (agonist) array.

Finally, it should be apparent that if the immunon concept (mechanism) is operationally enabling, the specific chemistry of the array is unimportant as long as the biophysical rules of receptor clustering are met and the ligands being arrayed can be recognized by the intended populations of receptors. For example, the targeted cell populations should not be sensitive to the exact nature of the scaffold used as long as the array is capable of interacting with the requisite number of receptors. The desired outcome can be achieved with a myriad different constructs as long as the principles of valence and/or size are maintained with fidelity. As a result, it is just as important to control the chemistry of the scaffold or backbone upon which the antigenic array is based as it is to identify and synthesize the appropriate ligand. One skilled in the art will appreciate that it is also important to confirm the integrity and composition of the final construct used before it is introduced into a biological system.

For example, if an immunon consists of eight receptors brought into a cluster, subthreshold clusters can be achieved by presenting the immune system with rigorously defined "valence restricted" antagonist arrays wherein the number of ligands is restricted to an integral number less than eight. In a naive animal, such arrays will be non-stimulatory and will prevent an antibody response to the epitope in question from developing. In an animal in which an immune response directed against the same antigen is already established, these constructs will act as competitive inhibitors to that response, i.e. they will be suppressive in nature.

On the other hand, an immunon must have a finite minimum size which is determined by the maximum packing density that the requisite number of antigen receptors can achieve on the surface of the lymphocyte. Arrays that cannot cover this minimum area (size restricted antagonist arrays) can be expected to be both non-stimulatory and suppressive no matter how many binding sites they may have. For small ligands such as DNP, fluorescein, or small peptides, the major determinant for array size is the scaffold, hence the size limit (preferably, less than approximately 150,000 daltons). But, for more complex ligands such as larger polypeptides, nucleic acids, or even proteins, the "ligands" themselves may be the controlling element with regard to the size of the final construct. In this case, even valence restricted constructs may exceed the nominal "size" criteria established for smaller epitopes. In this case, valence considerations will predominate over size considerations with respect to how the immune system will respond. An immunon cannot be expected to form if the array being introduced into the system has a subthreshold number of receptor binding sites no matter how big the array is in absolute terms.

In either case (size restricted or valence restricted antagonist arrays), many different chemistries can achieve the same outcome. Addressed below are three technical points important to the present invention. The first point is the preparation of the backbone scaffold so that the ligands can be covalently attached thereto in a controlled and selective manner. The second point is the preparation of the ligands themselves so that they can be attached to the scaffolds in a specific orientation. The third point is the formation and characterization of the final conjugate prior to its introduction into a biological system.

B. Scaffolds

Many different biologically acceptable carriers or scaffolds can be used to effect the desired outcome with respect to the formation of agonist or antagonist arrays. Some are capable of being used without selective chemical modification. The only significant restriction placed on these scaffolds is that they be freely soluble in physiologically acceptable aqueous buffers when the final constructs are prepared. The scaffold can be used to provide the necessary solubility for the final product even though the ligand being conjugated to the backbone is relatively insoluble. Alternatively, if the ligand in question has undesirable charge characteristics (e.g., cationicity) the scaffold can be used to counterbalance these characteristics so that the final product falls within preferred tolerances.

For general conjugation reactions, introduction of, for example, primary amines onto the scaffold provides a functional group capable of accepting multiple chemical modifications or manipulations that can be achieved using mild conditions in aqueous solutions. One skilled in the art will appreciate, however, that alternative chemistries can also be employed for these types of reactions. Set forth below is a representative sampling of the chemistries that can be employed to provide the necessary scaffolds for conjugation. Table 1 summarizes the different biophysical characteristics of certain scaffolds (see also Example 1) and underscores the generality of the concept.

TABLE 1

Molecular Characteristics of Polymer Molecules

| Polymer | Carrier | Carrier Composition |
|---|---|---|
| Dextran | Bacterial polysaccharide of glucose subunits | Predominantly linear, somewhat branched homopolymer |
| Polyacrylamide | Synthetic polyethylene polymer | Linear homopolymer, uncharged |
| Ficoll | Polysaccharide synthesized from sucrose | Three-dimensional & highly crosslinked |
| Carboxymethyl-cellulose | Carboxy-methylated plant polyglucose | Linear, negatively charged homopolymer |
| Polyvinyl alcohol | Synthetic polyethylene polymer | Linear uncharged homopolymer |
| Poly (D-GLU/D-LYS) | Synthetic polymer of "unnatural" D-amino acids | Linear variably charged random polymer of D-glumatic acid and D-lysine |
| Protein Oligomer | Naturally occurring | Size fractionated |
| Serum Albumin | soluble protein | oligomer of crosslinked |

TABLE 1-continued Molecular Characteristics of Polymer Molecules

| Polymer | Carrier | Carrier Composition |
|---|---|---|
| Chicken Ovalbumin Serum Immunoglobulin | | globular proteins |

Preferably, the materials used are subjected to analytical and, if necessary, preparative sizing techniques (for example, size exclusion gel chromatography or ultrafiltration) to ensure homogeneity and relatively narrow mass distributions both before and after modification. In addition, independent verification of mass (for example, by laser light scattering and/or equilibrium ultracentrifugation) can also be performed on these materials both before and after modification so as to assure that the scaffolds used are within the size tolerances needed for either agonist or antagonist array formation.

C. Epitopes

The chemistry necessary for modifying the desired ligand for attachment to the chosen scaffold is described generally below. Again, the specific chemistry employed can be modified or changed in a variety of ways. One skilled in the art will recognize that the details set forth herein are but examples of the types of chemistry available for producing the constructs to which the present invention relates.

1. Low Molecular Weight Haptens

The low molecular weight haptens specifically described herein were present in a form that could react directly with the available free amines on the scaffolds utilized without modification. For example, the fluorescein derivatives were formed using fluorescein isothiocyanate which rapidly reacts with available amines forming a stable thiourea linkage. Those skilled in the art will recognize that other small molecular weight haptens can also be employed using known chemical protocols.

2. Peptides

Peptides identified for use as a ligand can be modified so that they can be successfully arrayed and yet still be recognized by the immune system in the desired fashion. Naturally occurring peptides or proteins have three types of amino acid side chain moieties that can be readily used as functional groups with which to tether the peptide to the desired scaffold. These groups are: amines, as represented by the epsilon amino group of lysine and the N-terminal alpha amino group; carboxyls, as represented by the side chain carboxyl groups of aspartic or glutamic acid and the C-terminal alpha carboxyl; and the sulfhydryl group of cysteine. As one skilled in the art will appreciate, the side chains of glutamic acid, aspartic acid and lysine are frequently found on the external surface of proteins and, as a result are commonly involved in antigen-immune system interactions. Peptides containing a combination of more than one amino and/or carboxyl group require particular attention in terms of orientation specific and controlled chemistry. In addition, the potential for conjugate polymerization that exists when these residues are used for array formation must be addressed.

Use of the free sulfhydryl group of cysteine has a number of significant advantages. First, in most cases in biology, cysteine does not exist as a free sulfhydryl. As a result, it is rarely involved in antigen-immune system interactions. Second, there is a wealth of chemistry that takes advantage of sulfhydryls to the exclusion of any other reactive group commonly found in biology. Further, cysteine, as a naturally occurring amino acid, can be incorporated into recombinantly synthesized proteins. For these and other reasons discussed in more detail below, sulfhydryl chemistry is the preferred system for conjugating peptides to various scaffolds.

For all of the peptides specifically described herein, standard solid phase peptide synthesis techniques have been employed, the specifics of which are described in Example 9. When the peptide in question is conjugated to a protein, the issue of the ability to unambiguously quantitate the amount of peptide linked to the carrier must be addressed. In order to prevent significant steric factors from interfering with ligand binding, spacers of various kinds can be incorporated into the ligand in question.

Various "unnatural" omega amino carboxylic acids, such as epsilon amino caproic acid or delta amino valeric acid, can be used as spacers between the ligand in question and the cysteine (or cysteamine—see below) used to link the peptide to the scaffold. These amino acids have unique analytical characteristics when subjected to standard amino acid analyses and can be used to quantitate peptide "valence" as well as allow for a flexible linker between the peptide in question and the scaffold.

3. Proteins

Proteins provide for significantly different considerations with respect to the immune response generated to these types of antigens. These include multiple different antigenic epitopes per protein monomer as well as different types of epitopes (sequential, linear conformational, and discontinuous conformational epitopes). In order to deal with these issues, three categorically different approaches to protein antigens, their epitopic representation, their synthesis and their deployment in agonist or antagonist arrays, need to be taken into consideration. The first of these issues is the "mapping" of a protein's antigenic facade with smaller peptide or modified peptide based ligands. The second is the use of oligomeric constructs made up of the whole proteins or domains of larger proteins either crosslinked to themselves or to a scaffold. And, the third is the generation of "mimotopes" which can mimic the antigenic structure of protein epitopes but which bear little or no compositional similarity to the naturally occurring antigen. These approaches are described below in Example 10.

4. Carbohydrates

Set forth below are specific methods of covalently assembling molecules, that is, of coupling polysaccharides, oligosaccharides, sugars, glycoproteins or other materials through their reducing end groups to form larger molecular arrays. Alternatively, the chemistry described below can be used to attach polysaccharides, oligosaccharides, glycolipids or glycoproteins as haptens to a different molecular scaffold.

Reactive end groups, amino or sulfhydryl, suitable for coupling to other molecules can be produced in high yield by the following procedures which make use of the formation and selective reduction of intermediate Schiff bases:

Primary Aliphatic Amino Groups—The saccharide material is reacted (for example, for 18 hours, at pH near 5) with ethylenediamine dihydrochloride (concentration, for example, 0.1–1.0 M) (or other small diamine, $NH_2$-$(CH_2)_n$-$NH_2$, where n is a small number 2 or greater), in the presence of 0.01 M sodium cyanoborohydride (concentration, for example 0.01 M). Upon removal of reagents by dialysis or a desalting column, substantially complete reaction of reducing end groups is obtained, with formation of terminal primary amino groups suitable for subsequent coupling reactions.

Sulfhydryl Groups—The saccharide material is reacted, as above, cysteamine dihydrochloride as the diamine (concentration, for example, with 0.1–1.0 M). Upon completion of reaction, the resulting derivative disulfide can be readily reduced with standard disulfide reducing agents, such as Cleland's reagent, to yield free terminal sulfhydryl groups suitable for subsequent coupling reactions.

5. Nucleic Acids

In at least one application (the treatment of systemic lupus erythematosus), the antigen is known to be a nucleic acid—double stranded DNA. In a series of experiments designed to assess the minimum size of unmodified double stranded DNA needed for successful receptor binding it was found that approximately 40 base pairs were needed for 100% receptor binding. This requirement may be different if the double helix is covalently crosslinked instead of relying solely on the hydrogen bonding of the base pairs for stabilization.

Naturally occurring DNA, synthetic DNA or modified DNA containing phosphorothioates as opposed to naturally occurring phosphate linkages can be used to produce a successful ligand. Example 11 includes a description of the types of chemistries that can be employed to produce the desired epitopes possessing the necessary functional groups for covalent attachment to the appropriate scaffold.

D. Conjugates

The final steps in the preparation of a conjugate suitable for use in the method to which the invention relates is the assembly of the desired array from the appropriate scaffolds and ligands and the confirmation that the final material is, in fact, what it is intended to be. Characterization of the final constructs is an important part of the preparation and use of these materials (see Example 12).

II, Utilization of Constructs to Suppress T-cell Dependent Immune Responses

As indicated above, the earlier filed applications of the present series relate, in large part, to the suppression of T-cell independent responses by constructs comprising size restricted backbones and small molecular weight haptens (such as DNP and fluorescein). Data presented in the Examples that follow demonstrate that the same type of suppression can be obtained with more complex responses involving T-cell dependent antibody production, represented by IgG and IgE.

As will be evident from the Examples that follow, rapid and complete obliteration of a hapten-specific antibody response (represented by IgG production) can be effected by administration to animals of a suppressive construct specific for the hapten, prepared as described herein. The data indicate that suppression occurs at the cellular level. Clinically important antibody responses to extrinsic allergens (both small chemical entities and complex epitopes) represented by IgE production can be completely suppressed by constructs meeting the valence and size criteria set forth above. In addition, constructs of the present invention can be used to suppress autoimmune responses.

It will be appreciated from the results set forth in the Examples that follow that the methodology presented here, as well as in the earlier filed applications, is broadly applicable to T-dependent antibody responses to small molecular weight haptens as well as to complex antigens (peptides, proteins lipoproteins, glycoproteins, nucleic acids, carbohydrates, lipids and glycolipids). The principles involved are not dependent on the use of specific backbones, or scaffolds. Polymers having vastly different chemistry (dextran, polyacrylamide, Ficoll, etc.) can be used. Further, and as indicated above, the technology is applicable to T-dependent antibody responses of all classes to any and all extrinsic (allergic) or intrinsic (autoimmune) antigens that comply with the rules of the Immunon model of antigen recognition.

The following non-limiting Examples describe certain aspects of the invention in greater detail.

EXAMPLES

Example 1

Scaffold Synthesis

A. Dextran

Dextran can be considered a "prototypical" scaffold for a number of reasons: 1) it is freely soluble in aqueous buffers, 2) it can be readily modified using "off the shelf" chemistry, 3) it has been used in humans in gram quantities as a plasma expander with no significant toxicities, 4) it is available in roughly size-fractionated bulk quantities at low cost and 5) there are no known mammalian dextranases. The latter point is particularly important since one of the primary considerations of this technology is that the arrays be metabolically stable so that the desired outcome can be effected in an experimental animal or human.

Representative examples using different chemistries are presented here. One skilled in the art will appreciate that chemistries used to modify dextran can also be extrapolated to other systems.

a. Basic "Dexamine" and GMB-dexamine

The chemistry used to activate dextran such that covalent attachment of a peptide can occur is shown in FIG. 1. Dextran of various molecular weights (1) was first carboxymethylated with chloroacetic acid ($ClCH_2CO_2H$) at glucosyl 2'-, 3'- or 4'-hydroxyl positions to yield the corresponding carboxymethyl-dextran (2). Conversion into dexamine (3) was then accomplished by reaction (of carboxymethyl-dextran) with ethylene diamine ($NH_2CH_2CH_2NH_2$) in a water soluble carbodiimide (EDC=1-ethyl-3-(3-dimethylaminopropyl)carbodiimide hydrochloride)-mediated coupling reaction. The presence of free amino groups in dexamine (3) allows measurement of the "amine substitution density" using standard quantitative analytical chemistry techniques. Expressed as the number of μmoles of amine present per milligram of dexamine (3), the value for amine density represents the theoretical maximum substitution density for any particular peptide. Dexamine (3) used in the Examples described herein was found routinely to contain approximately one primary amino group ($—NH_2$) for every five glucosyl residues (or 1000 g/mole) present in the dexamine (3) sample.

Derivatization of the dexamine (3) amino groups with the heterobifunctional acylating agent: gamma-maleimido n-butyric acid N-hydroxysuccinimide ester (GMBS) then gave the activated or "conjugatable" form of dextran: gamma-maleimido n-butyryl dexamine (GMB-dexamine, 4). It is the maleimide functional group within GMB-dexamine (4) that reacts with (i.e. conjugates with) the sulfhydryl group of a cysteine-containing peptide to generate a peptide-dextran conjugate.

The dextran (1) used in the preparation of the peptide-dextran conjugates was a size-fractionated, average molecular weight polymer. Chloroacetic acid and ethylene diamine were purchased from Aldrich Chemical Co. 1-Ethyl-3-(3-dimethylaminopropyl)carbodiimide hydrochloride (EDC) and gamma-maleimido n-butyric acid N-hydroxysuccinimide ester (GMBS) were purchased from Sigma Chemical Co. Trinitrobenzensulfonic acid (TNBS) was obtained from Pierce Chemical Co. Phosphate-buffered saline (PBS: 150 mM NaCl, 10 mM phosphate pH 7.3–7.4), used in the preparation of GMB-dexamine (4), was prepared fresh (for each day's set of reactions) from an autoclaved 10× PBS stock solution and autoclaved water with subsequent filtering through a 0.2 µm filter. (Preparation of PBS in this manner is important to the production of conjugates that are devoid of undesirable contaminants). Dialysis tubing (6,000–8,000 mwco) was obtained from Spectrum Medical Industries, Inc.

Purification of dextran (1) and molecular weight measurement of dextran (1) or dexamine (3) samples were carried out by size exclusion chromatography followed by equilibrium ultracentrifugation, and/or laser light scattering analysis.

Carboxymethyl-dextran (2) was produced from dextran as follows: Sodium hydroxide (675 mmole, 135 mL of 5 M NaOH) was added to 0.3 L of water and the resulting solution chilled in an ice-water bath (0° C.) with stirring. Chloroacetic acid (64.4 g, 685 mmole) was then added and stirring continued at 0° C until complete dissolution occurred. The resulting solution was allowed to warm to room temperature and the pH was adjusted to ca. 7 by the addition of either NaOH or chloroacetic acid. After being diluted to 0.5 L total volume, 185 mL of the chloroacetate solution was added to the dextran sample (0.143 mmole) and the carboxymethylation reaction initiated by the addition of 50 mL of 10 M NaOH (500 mmole). The reaction mixture was diluted to 250 mL total volume and carboxymethylation allowed to proceed for 20 hours at 37° C. The reaction was then terminated by adjusting the solution pH to ca. 7 with 6 M HCl. After being allowed to cool to room temperature, the reaction mixture was dialyzed for 5 days against water (two water changes per day) and the resulting carboxymethyl-dextran (2) isolated by lyophilization.

Dexamine (3) was produced from carboxymethyl-dextran (2) as follows: (0.143 mmole carboxymethyl-dextran (2) reaction scale): Carboxymethyl-dextran (2) was dissolved in 300 mL of water and ethylene diamine was added (45 g, 750 mmole). The resulting solution was stirred at room temperature and the pH adjusted to ca. 5 with 1 M HCl. 1-Ethyl-3-(3-dimethylaminopropyl)carbodiimide hydrochloride (EDC, 4 g, 20.86 mmole) was then added portionwise over a 10 to 20 minute period with continuous stirring. The pH of the reaction mixture was checked every 15 minutes and maintained near pH 5 (via the addition of 1 M HCl) for 4 hours. Extensive dialysis was then carried out as follows: overnight against 30% AcOH, 24 hours against water (2 water changes), overnight against 30% AcOH, 24 hours against water (2 water changes), overnight against 1 M NaCl and then 48 hours against water (2 water changes per day). The resulting dexamine (3) was isolated by lyophilization.

Measurement of (dex)amine content (i.e. amine substitution density) was carried out as follows: Dexamine (3) was dissolved in 1 mL of 0.1 M sodium tetraborate buffer (pH 9.3) to give a solution concentration of 1–2 mg/mL. Freshly-prepared trinitrobenzenesulfonic acid (TNBS, 25 µL of a 30 mM solution in sodium tetraborate buffer) was added and the resulting (vortexed) reaction mixture stored in the dark for 2 hours at room temperature. The yellow-colored solution was then read against a reagent blank at 366 nm. Standards of 1 mM lysine, 2 mM glycine or 2 mM aminobutyric acid were prepared and a standard curve generated from various aliquots diluted to 1 mL total volume with buffer.

GMB (gamma-maleimido n-butyryl)-dexamine (4) was produced from dexamine (3) as follows: Dexamine (produced as described above) was dissolved in phosphate-buffered saline (PBS, pH 7.5) and stirred at room temperature to give a solution concentration of 5–10 mg/mL. A five-fold molar excess of GMBS (gamma-maleimido n-butyric acid N-hydroxysuccinimide ester) relative to (dex) amine content was then dissolved in dry tetrahydrofuran (THF, stored over 4 Angstrom molecular sieves) such that a GMBS concentration of ca. 50 mg/mL was achieved. The GMBS/THF solution was added dropwise to the stirring dexamine (3) solution and the acylation reaction allowed to proceed for 30 minutes at room temperature with the solution pH being maintained at 7.1–7.5 by the dropwise addition of 1 mM NaOH. GMB-dexamine (4) was then separated from excess GMBS by gel filtration of the reaction mixture on a 15 mm×30 cm Sephadex G-25 column equilibrated in PBS (pH 7.5). The column effluent was monitored at 280 nm with a Pharmacia Dual Path Monitor UV-2. Column fractions containing GMB-dexamine (4) were combined and set aside pending the availability of a reduced cysteine (Cys)-containing peptide.

b. Alternative Neutral, Anionic and Cationic "Dexamines"

As mentioned above, under certain circumstances the scaffold will need to compensate for an undesirable charge profile of the ligand in question. Described below are means by which dextran-based scaffolds can be made to have neutral, anionic or cationic characteristics using a modification of the fundamental dextran chemistry described above.

Figure 2:
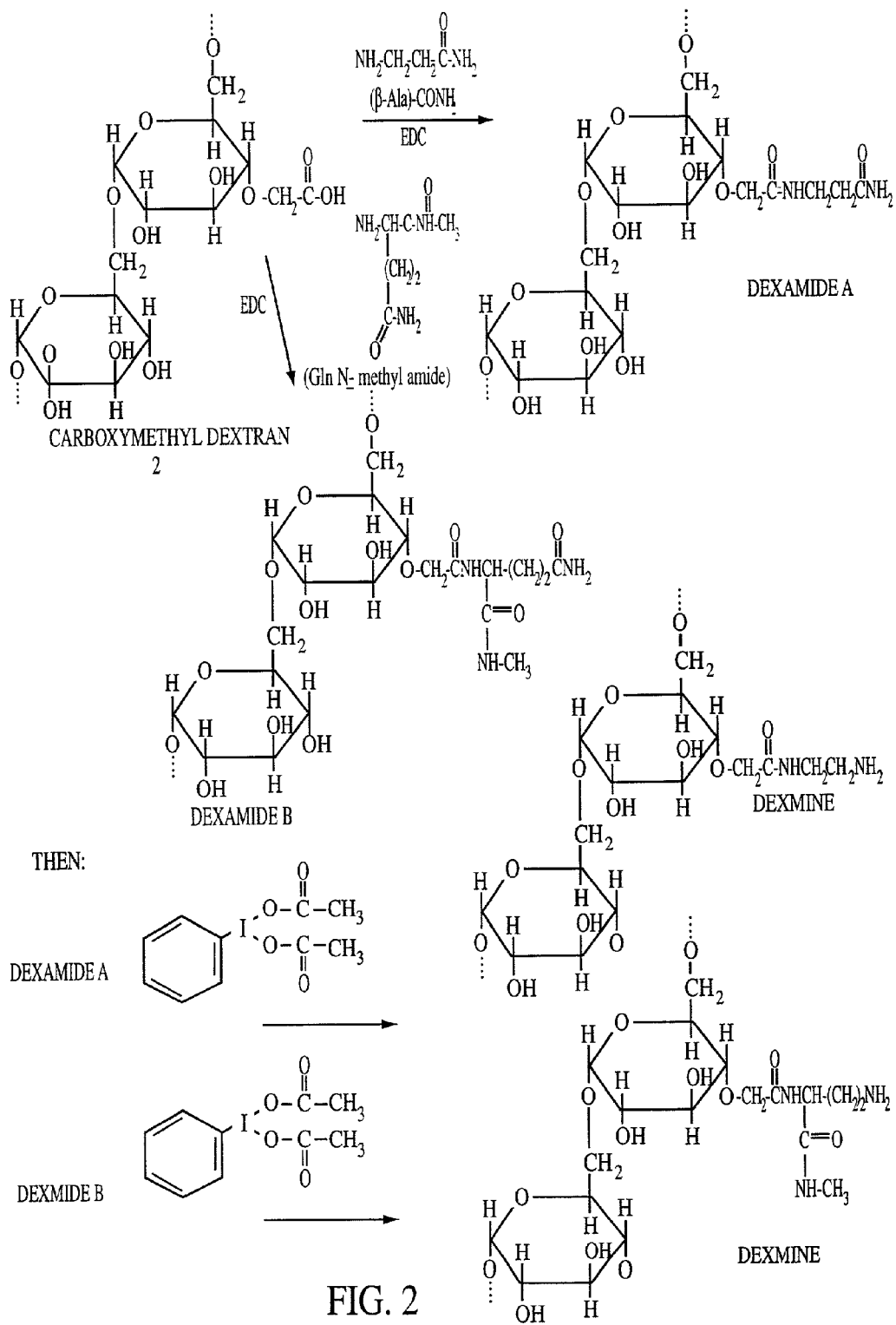
FIG. 2. Conversion of carboxymethyl dextran to dexamine.

For the preparation of neutral scaffolds, the first modification of dextran (1) to carboxymethyldextran (2) is identical to that described above. At this point, however, two different amino amides (β-Ala-CONH$_2$ or L-Gln-CON-HCH$_3$) can be condensed with carboxymethyl dextran to form two different types of "dexamides" which will ultimately be converted into charge neutral dexamines described in FIG. 2.

For the preparation of anionic scaffolds, an alternative precursor dexamide is needed. These can be formed by the condensation of either L-Asn or L-Gln with dextran according to the following protocol:

4-Nitrophenyl chloroformate (685 mg, 3.4 mmole) was added to a solution of 1 g dextran (1) (13.87 µmole) in 60 mL of a dry DMSO-pyridine mixture (1:1, v/v) at 0° C. in an ice-water bath. To this solution was added 76 mg of 4-(N,N-dimethylamino)pyridine (6.22 mmole). The reaction mixture was stirred at 0° C. for 4 hours and then a fifty-fold molar excess of either L-Asn or L-Gln was added. The reaction mixture was allowed to warm slowly to room temperature and then stirring was continued for an additional 48 hours. The dexamide was precipitated with an excess of dry ethanol/ethyl ether (8:2, v/v) and then dried in vacuo. The dried material was dissolved in water, dialyzed for 3 days against water and then lyophilized (1×).

Figure 3:
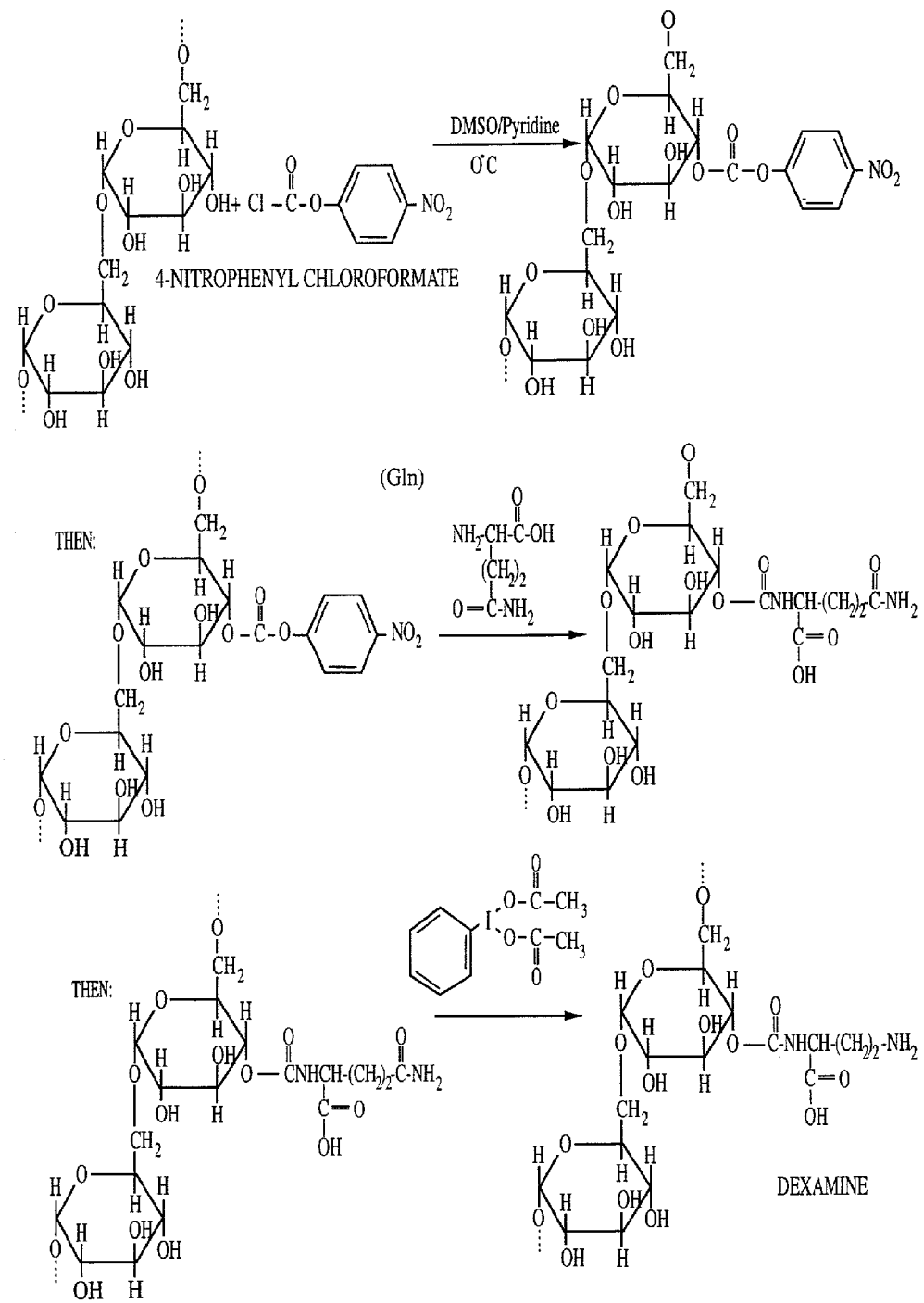
FIG. 3. Conversion of dextran to polyanionic dexamine.

Once the desired dexamide is prepared it can be converted into its corresponding neutral or anionic dexamine by first dissolving the dexamide in 50% aqueous acetonitrile and stirring gently at room temperature. To this solution, a several fold molar excess (relative to the calculated amide content) of iodobenzene diacetate is added and the reaction mixture is stirred overnight. (Iodobenzene diacetate will stoichiometrically convert one equivalent of a primary amide into the corresponding primary amine.) The resulting dexamine can be purified from the other reaction products by size exclusion chromatography, vacuum concentration and then lyophilization from water. FIG. 3 illustrates the complete conversion of dextran to anionically charged dexamine.

Figure 4:
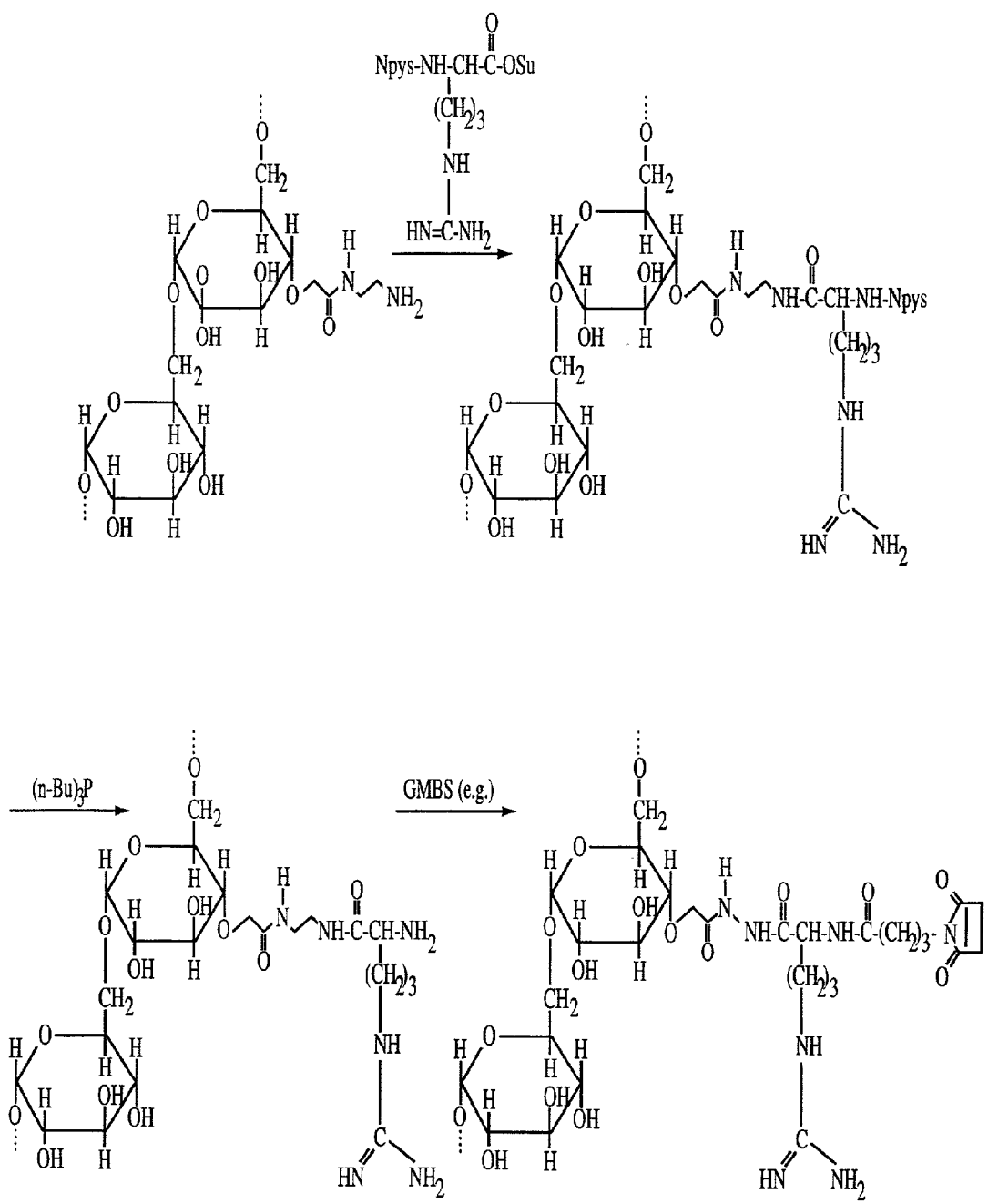
FIG. 4. Conversion of dexamine to polycationic dexamine.

While not as useful as dexamine possessing an anionic character, dexamine with a net positive charge (following conjugation) might be found useful in certain limited cases. Preparation of this material can be carried out with ethylene diamine-containing dexamine as follows: Acylation of the (dex)amine (4) groups with $N^\alpha$-Npys-L-Arg-OSu results in the incorporation of one equivalent of positive charge for every equivalent of acylated (dex)amine (4). Subsequent removal of the $N^\alpha$-Npys group (with (n-Bu)$_3$P) liberates a free α-amino group which can be acylated further with GMBS or converted directly into the maleimide functional group via N-methoxycarbonyl maleimide. Longer and shorter homologs of Arg can be used in an analogous fashion (e.g. Homoarg). (See FIG. 4)

B. Polyacrylamide and Poly(acrylamine-acrylic Acid)

Linear polyacrylamide was synthesized from the monomer is aqueous solution, giving polymer preparations with average molecular masses varying from 20,000 to 500,000 kDa, as determined by the methods of equilibrium ultracentrifugation, high pressure liquid chromatography (HPLC), size-exclusion gel chromatography (SEC) and laser light scattering. Preparations were size fractionated on appropriate gel filtration chromatography columns, Sepharose CL-2B, CL-4B or CL-6B, Pharmacia, to yield center cuts with relatively narrow molecular mass distributions, as measured by HPLC.

Usually, such polyacrylamide preparations were chemically substituted with amino groups to prepare them for later coupling with hapten reagents. This was accomplished by first hydrolyzing carboxamide groups for varying times, in a carbonate-bicarbonate buffer, to produce a series of preparations with differing carboxyl group content. Such carboxylated polymers were then coupled at their carboxyl groups to ethylenediamine by the action of water-soluble carbodiimide, generating an amide bond and a free amino group in place of each carboxyl group undergoing reaction. Hapten was subsequently coupled to the resulting amino-substituted polymer by chemical substitution at the amino groups.

For a detailed description of the methods used see: Dintzis, et al (*Proc. Nat'l. Acad. Sci.*, U.S.A., 73:3671–3675 (1976) and Inman, et al (*Biochemistry* 8, 4074–4082 (1989)).

In order to provide an alternative to neutral linear polyacrylamide and to provide another carrier with anionic characteristics, poly(acrylamine-acrylic acid) was synthesized using a modification of the iodobenzene diacetate reaction described above with commercially available size-fractionated random copolymers of acrylamide acrylic acid. Specifically, I,I-bis(trifluoroacetoxy)iodobenzene is dissolved in DMF to which an equal volume of water is slowly added with continuous stirring. The size fractionated polymer is then added to the reaction mixture and stirred overnight at room temperature. It is then transferred to a separatory funnel, washed with water equivalent to three times the volume of the reaction mixture, and extracted with diethyl ether (4 extractions with 4× volume). The final aqueous layer is then vacuum concentrated and the residue redissolved in water and dialyzed against water for several days. The dialyzed product is then filtered and lyophilized to yield a fluffy, white solid.

Figure 5:
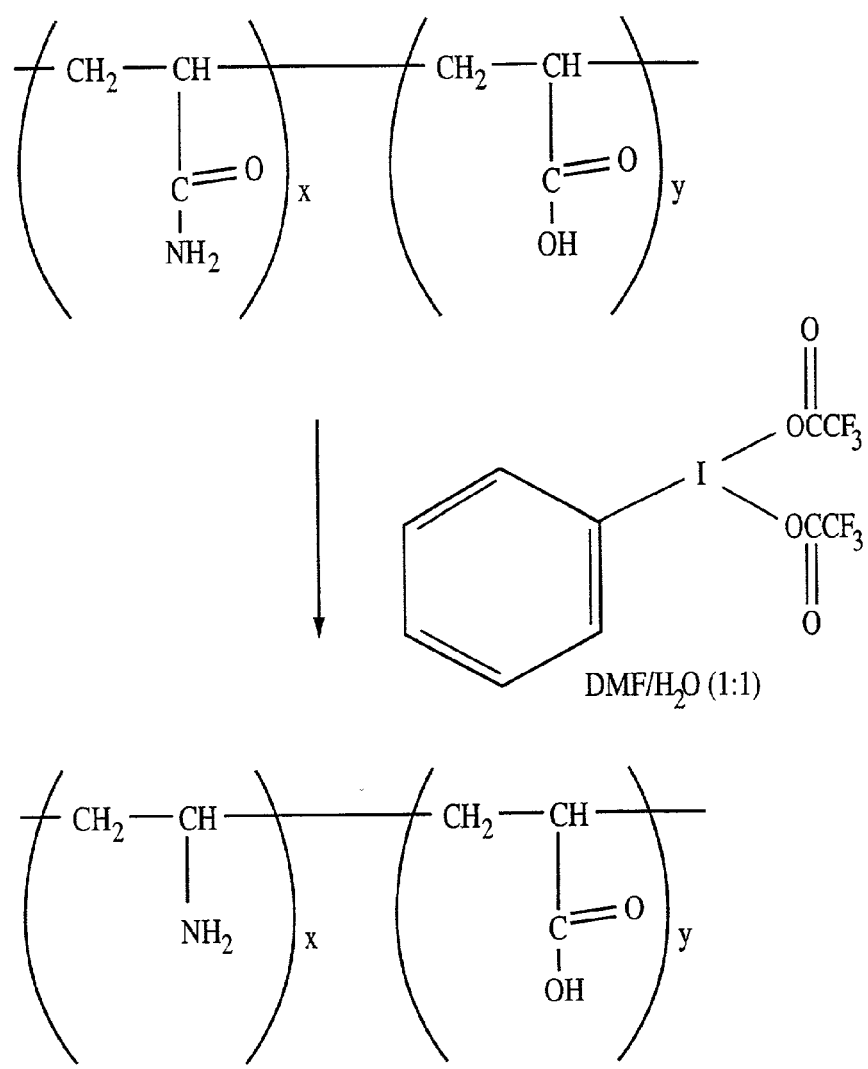
FIG. 5. Conversion of poly(acrylamide, acrylic acid) to primary amine containing poly(acrylamide, acrylic acid).

Because one equivalent of I, I-bis(trifluoroacetoxy)iodobenzene stoichiometrically converts one equivalent of a primary amide into the corresponding primary amine, it is possible to vary the amine substitution density of the final polymer product. Furthermore, one skilled in the art will appreciate that the same procedure can be employed for any acrylamide containing polymer regardless of the acrylic acid content. The conversion of poly (acrylamide-acrylic acid) into the corresponding amine-containing polymer is shown in FIG. 5.

C. Ficoll

Ficolls, like dextrans, are polysaccharide polymers that have free hydroxyls that can be modified using the same chemistry as described for the conversion of dextran to the various dexamines (neutral, anionic, and cationic). In addition, bulk quantities of these materials are available from commercial sources in various molecular weight ranges. The difference between dextran based scaffolds and Ficoll based scaffolds is the fact that Ficolls are more globular or "three dimensional" in nature while dextrans are more linear and branched. As can be se en from the data presented in the Examples that follow, this difference does not seem to carry with it significant functional consequences with respect to the production or use of agonist or antagonist arrays.

D. Carboxymethyl Cellulose

Again, carboxymethyl cellulose is very similar to both Ficoll and dextran from the biochemical perspective. This polymer, however, has a net anionic character from the beginning and, as a result, can be used to produce anionic scaffolds. As will be appreciated, the chemistry needed to modify this polymer is essentially the same as that for dextran once it has been carboxymethylated.

E. Polyvinyl Alcohol

While polyvinyl alcohol is not carbohydrate based, it does possess free hydroxyl moieties that can be modified by the same chemistry as described above for dextran.

F. Poly(D-Glu/D-Lys)

Poly(D-Glu/D-Lys) is a random, linear co-polymer of D-glutamic acid and D-lysine that can be purchases from commercial sources in molecular weight ranges below 100,000 daltons and with an approximate composition of 40% D=lysine and 60% D-glutamic Acid. Higher molecular weight scaffolds can be produced by the introduction of various water soluble crosslinking agents such as water soluble carbodiimides at various concentrations. The resulting crosslinked material can then be subjected to the same type of size exclusion chromatography and molecular mass analysis as that for the other polymers described above. As the polymer already possesses free primary amines derived from the epsilon amino groups of the D-lysine residues, no further modification is necessary for these constructs to accept linking groups such as GMBS. It will be appreciated, however, that the ability to control overall charge is limited with this type of preparation.

G. Proteins

Proteins or other polypeptides behave in many respects like the poly(D-Glu/D-Lys) copolymer with respect to the availability of both carboxyl and amino groups for chemical modification. Important advantages that proteins offer are set forth below.

First, proteins can be crosslinked and fractionated with respect to size in a manner similar to the crosslinking and separation of the poly (D-Glu/D-Lys) described above. The fractions can be effectively segregated into what would be the equivalent to valence restricted oligomers (dimers, trimers, etc.). As a result, these constructs can be used as agonist and/or antagonist arrays without further modification.

Second, recombinant DNA/protein engineering technologies have evolved to the point that fusion proteins made up of a core "scaffold" with recombinantly produced oligomeric representations of other proteins or protein domains can be constructed. Again, the final product can be formulated to represent valence restricted arrays of the desired "epitope or ligand" just as if they had been chemically crosslinked or conjugated to a valence restricted carrier.

Finally, streptavidin has a relatively unique structure that can be used to form tetrameric arrays by the introduction of a biotin moiety onto the desired ligand. Streptavidin has four binding sites for biotin that have such high affinity for this moiety that once bound are essentially the same as a covalent linkage. In addition, streptavidin is freely soluble and has an isoelectric point near neutrality so that undesirable charge characteristics can be avoided.

H. "Point Source" Valence Restricted Scaffolds

The majority of the data disclosed herein has been generated using size-restricted scaffolds. As mentioned above, an alternative approach is to use valence-restricted scaffolds for producing agonist or antagonist arrays. Illustrated below are a number of valence-restricted or "point source" scaffolds that can be utilized for these purposes. One skilled in the art will realize that these scaffolds are only a few of the types of potential valence-restricted scaffolds that can be constructed to meet this need.

Figure 6:
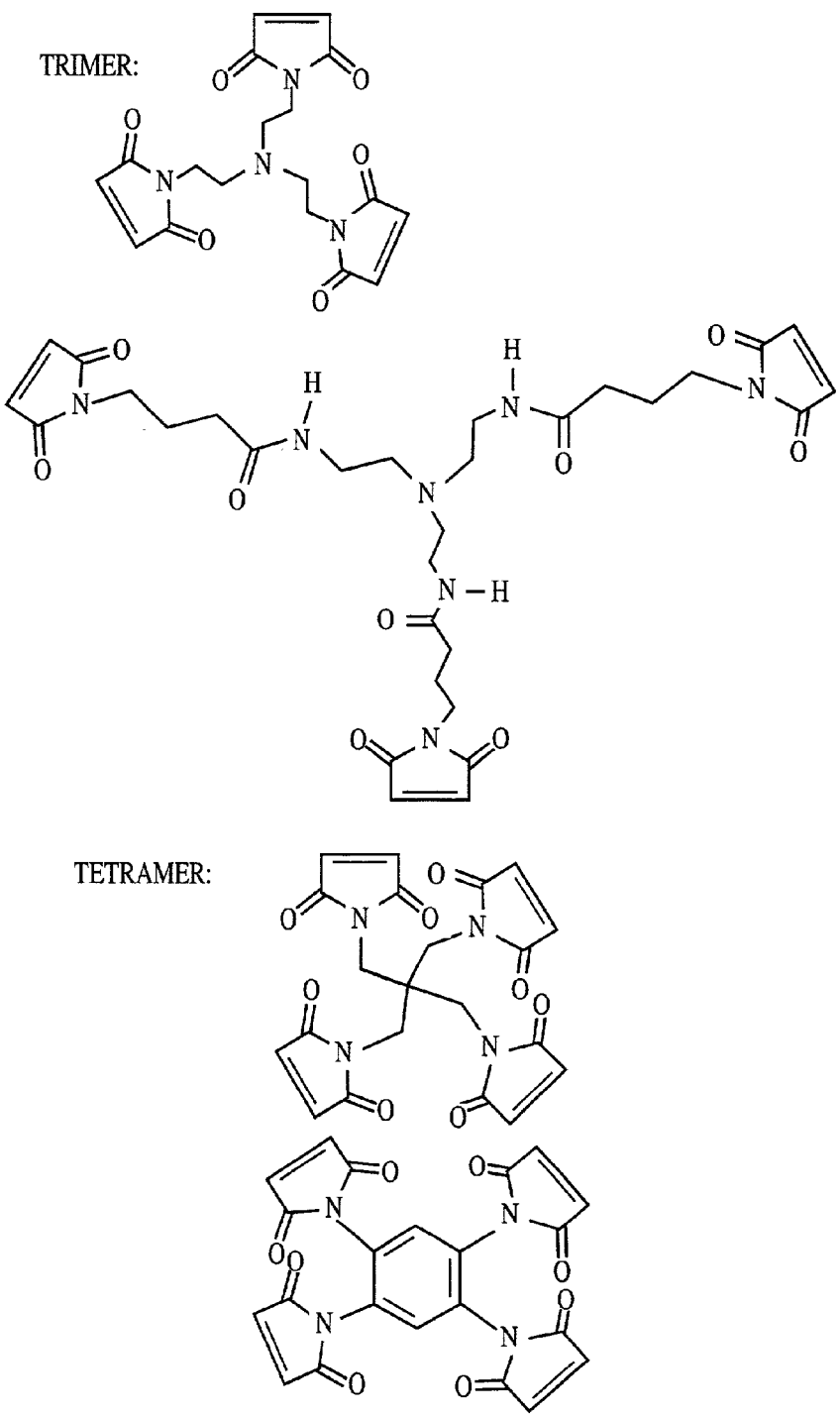
FIG. 6. Examples of trimeric and tetrameric "point source" scaffolds.

Using the maleimide/succinimide moiety as a representative reactive group for this series of scaffolds, several potential compounds can be synthesized from commercially available starting materials. Illustrated in FIG. 6 is a sampling of these types of "point source scaffolds". One skilled in the art will appreciate that the specific compounds described can be modified to produce point source scaffolds that utilize any number of alternative chemistries for conjugation or any size of "arm length" needed.

I. Valence Restricted Scaffolds Based on Cyclodextrins

An alternative type of scaffold can also be made that has the capability of being varied with respect to both the effective size and valence of the final construct. An example of this type of scaffold using beta-cyclodextrin as a template is illustrated below wherein the valence can be controlled with precisely defined chemistry and the arm length using various types of flexible spacers such as polyethylene glycol.

The cyclodextrins (CD) are oligosaccharides made up of glucose units that are linked through α 1–>4 glycosidic bonds. In the resulting torus shaped molecule, the primary and secondary hydroxyls are positioned on opposing faces.

Figure 7:
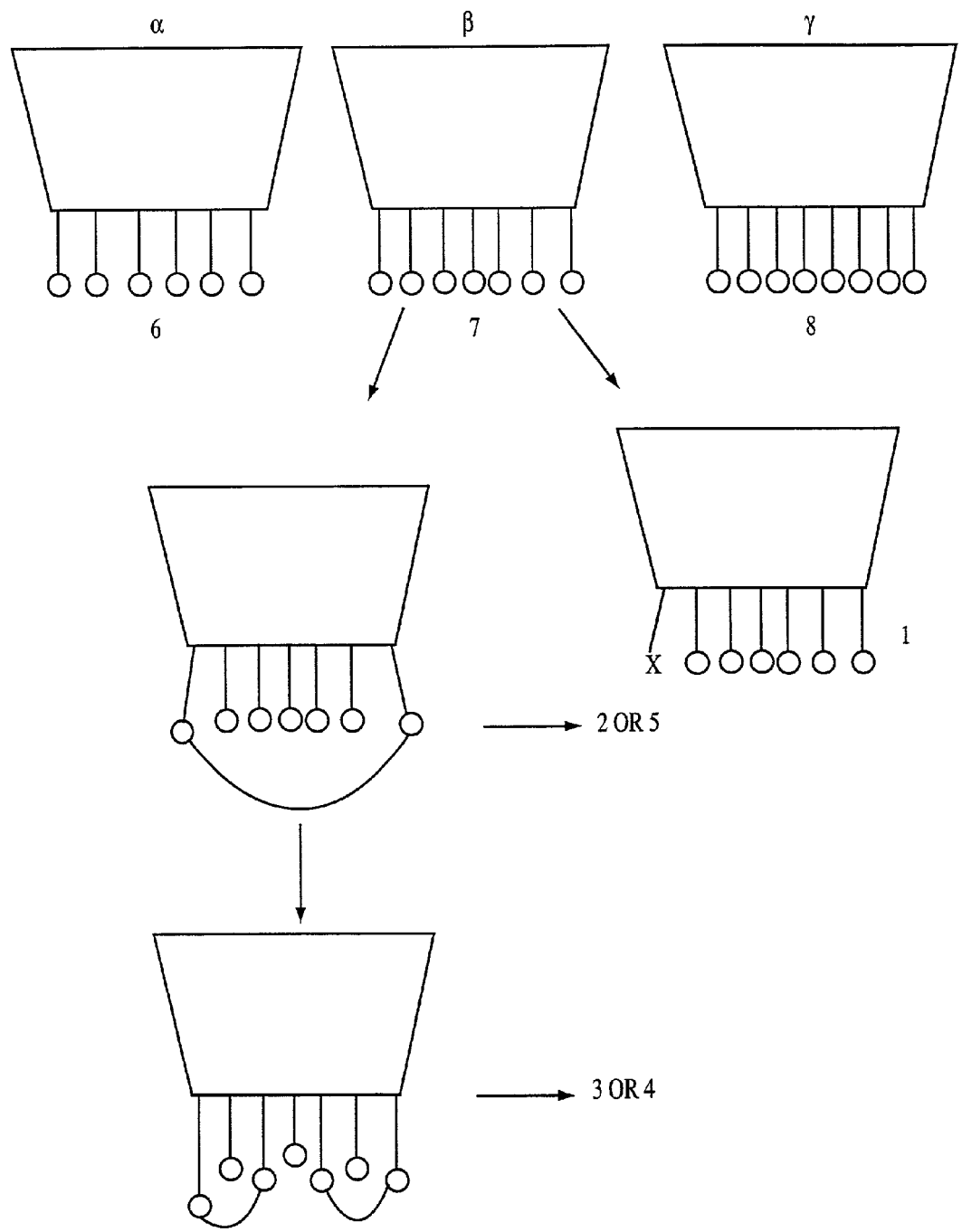
FIG. 7. Cyclodextrins as point source scaffolds.

It is possible to selectively functionalize the primary hydroxyls in the presence of the secondary hydroxyls. In addition, through the use of "linker groups" any combination of polyfunctionalized cyclodextrins can be achieved (FIG. 7).

Perderivitization of α, β or γ CD provides the corresponding 6, 7 and 8 valenced products. Each of these compounds can also be mono-functionalized. Treatment of β-CD, the most readily available substrate, with a bifunctionalized protecting group will lead to the bis protected product. This in turn can provide the 2 or 5 substituted products. Accordingly, reaction with two linker groups leads to products with valences of 3 and 4. Thus it is possible to attach between 1 and 8 epitopes to CD by judicious use of protecting groups.

Using this type of chemistry, valence and "arm length" can be varied to produce what can be considered as a radially disbursed array or "octopus-like" scaffold for ligand presentation. This type of array is optimal for receptor/ligand interactions when the receptor population is relatively free to move in the cell surface membrane. In addition, the chemistry of the "arms" can be varied to produce scaffolds with relatively free range of motion to arms with progressively less flexibility.

Disclosed below are some of the chemistries that can be employed to make these types of constructs for use in suppressing an undesirable antigen specific immune response.

β-Cyclodextrin 1, was transformed into its heptaamino derivative 2, using literature procedures (Boger et al, Helvetica Chimica Acta 1978, 61:2910) (Scheme 1).

Scheme 1

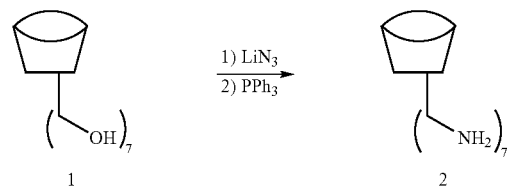

The extended arm product 3, was produced as follows heptaamino β-cyclodextrin (2) (3.0 g, 2.15 mmol) and triethylamine (2.4 mL, 17.2 mmol) were dissolved in 50 mL DMF. EDC (3.78 g, 19.3 mmol) was added followed by Boc-ε-aminocaproic acid (5.53 g, 19.3 mmol). The reaction mixture was stirred overnight, at which time 200 mL water was added and a precipitate formed. The solid product was filtered, washed with water and dried under vacuum to yield 4.78 g (85%) of the Boc protected 3. Deprotection was effected as follows the product was dissolved in 50 mL of HCl saturated dioxane (4N) and stirred for 3 h. Evaporation followed to yield 3, 2.99 g (75%).

Scheme 2

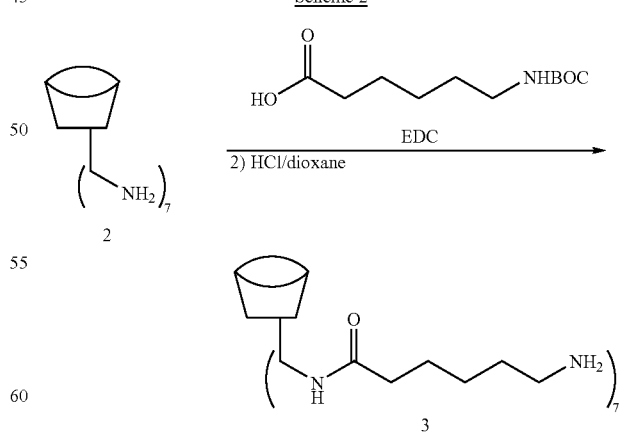

CS-0001 was produced from 3 as follows. The extended arm β-cyclodextrin (3) (500 mg, 0.23 mmol) was dissolved in 60 mL of 0.1M NH$_4$CO$_3$. GMBS (2.25 g, 8.05 mmol) was dissolved in 40 mL THF and added to the reaction mixture, which was stirred overnight. The mixture was evaporated and then purified by RPHPLC to yield 251 mg (36%) of CS-0001.

The fluorescein specific construct CI-374 was produced from 3 as follows. The extended arm β-cyclodextrin (3) (40 mg, 0.019 mmol) was dissolved in 10 mL of 1.1M NaHCO₃. Fluorescein isothiocyanate (200 mg, 0.52 mmol) was added and the resulting mixture was stirred overnight. The orange solution was then ultrafiltered through a YM3 membrane until the filtrate remained uncolored. The remaining orange retentate was purified by RPHPLC to yield CI-374, 20mg (16%).

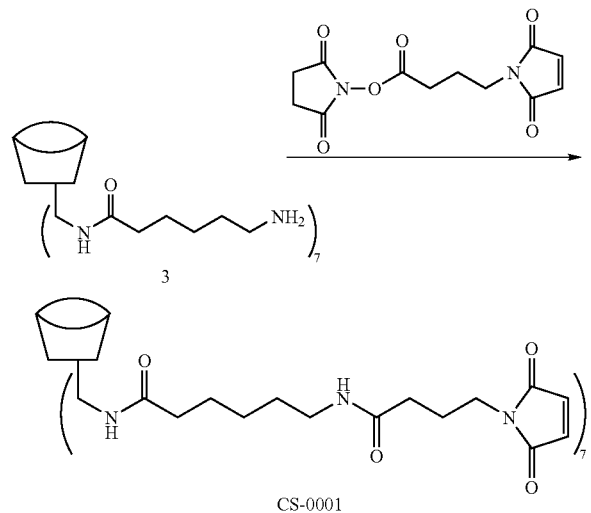

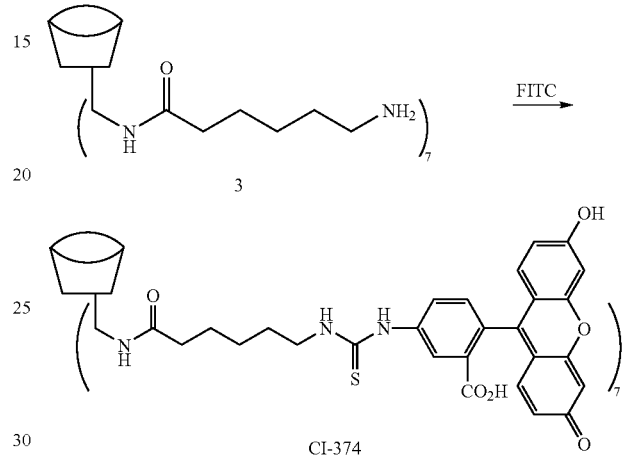

An additional scaffold, CS-0002, was produced under the conditions outlined above; 3 was condensed with Boc-ε-aminocaproic acid followed by removal of the Boc group. The resulting longer armed version of 3 was then reacted with GMBS to provide CS-0002 (Scheme 4).

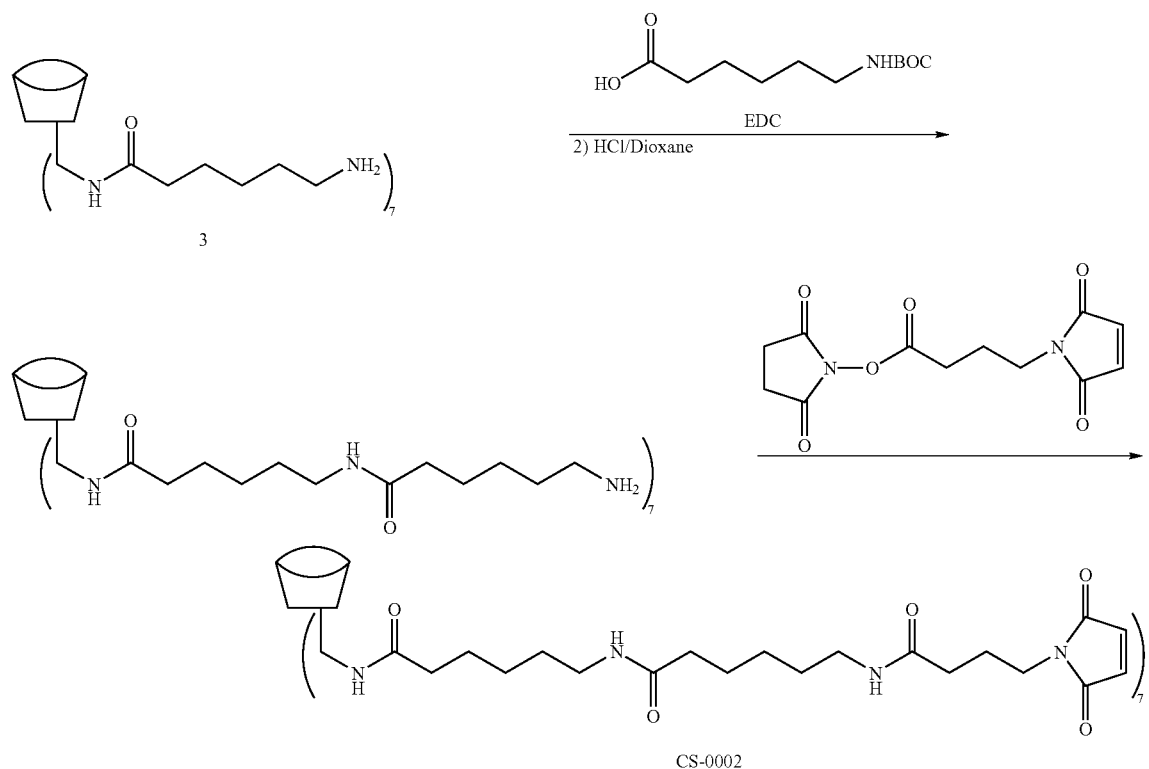

The fourteen armed scaffold (6) was produced as follows. Heptaamino β-cyclodextrin (2) (500 mg, 0.36 mmol) was dissolved in 4 mL DMF. Nα-t-Boc-Nα-t-Boc-L-lysine-N-hydroxysuccinimide ester (4.56 mg, 10.1 mmol) was added followed by N-methylmorpholine (320 µL, 2.88 mmol). The reaction mixture was stirred overnight at which time 25 mL of water was added and a precipitate formed. The solid product was filtered, washed with water and dried. The resulting solid was dissolved in HCl saturated dioxane and stirred 3 h. Evaporation produced 575 mg (63%) of 5.

This fourteen armed product-5 (400 mg, 0.16 mmol) was dissolved in 4 mL DMF. Boc-ε-aminocaproic-N-hydroxysuccinimide ester (2.89 g, 8.85 mmol) was added followed by N-methylmorpholine (485 µL, 4.42 mmol). The resulting mixture was stirred overnight, at which time 25 mL of water was added to effect precipitation of the product. The fourteen armed scaffold was isolated upon filtration, washed with water, and dried. The resulting solid was immediately dissolved in HCl saturated dioxane and stired 3 h. Evaporation yielded 96 mg (60%) of 6.

These compounds have all exhibited satisfactory $^1$H NMR, mass spectral analysis and amino acid analysis.

Scheme 6

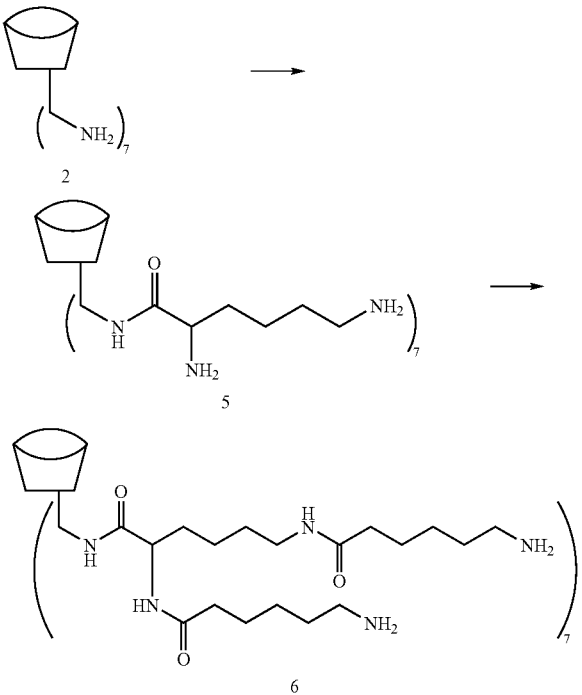

Other arms can consist of polyethylene glycol units or some other hydrophillic polymeric subunit. Spacers of this sort would permit exploration of distances between receptors. A heterobifunctional linker with amine and hydroxyl termini can be functionalized such that an activating group can be fashioned at the hydroxyl terminus. This can in turn be displaced by the amines of compounds 2 or 3. Upon removal of the N-terminal protecting groups, a scaffold such as the ones previously described, containing longer spacer arms, will result.

Example 2

Synthesis and Analysis Procedures for Peptides used in Conjugate Preparation a. Solid Phase Peptide Synthesis The peptides destined for incorporation into peptide-dextran conjugates were generated by solid phase peptide synthesis using a standard stepwise elongation of the peptide chain. In brief, solid phase peptide synthesis begins with $\underline{N}^{60}$-deprotection of the amino acid residue attached to the synthesis resin. This step is followed by neutralization and washing of the deprotected amino acid-containing resin which prepares it to receive (i.e. react with) the next amino acid, itself activated to facilitate the formation of the first peptide bond (—NH—CO—). A subsequent washing of the now (di)peptide-containing resin is then followed by the same series of events which are continued until the desired peptide has been produced. The finished peptide is then cleaved off of the resin under conditions which simultaneously remove some or all of the individual amino acid side-chain protecting groups. Specific protecting groups designed to be removed under different conditions than that used for resin cleavage are frequently employed so as to render subsequent conjugation to backbone more controllable.

All reagents used in the studies described herein were obtained from standard commercial sources.

Solid phase peptide synthesis was carried out on either an Applied Biosystems (ABI) 430A or Biosearch 9600 automated peptide synthesizer using $\underline{N}^\alpha$-tert-butyloxycarbonyl (N-t-BOC) protection. Trifunctional amino acids other than Cys were protected with (protecting) groups compatible with standard N-t-BOC solid phase peptide synthesis. N-t-BOC-L-Cys was S-protected with the p-methylbenzyl (Meb, HF labile), acetamidomethyl (Acm, HF stable) or nitropyridinesulfenyl (Npys, HF stable) group depending on the need for HF labile or HF stable sulfhydryl protection. The addition of a Cys residue to either the N- or C-terminus of a peptide destined for incorporation into a conjugate provided the peptide with a nucleophilic moiety in the form of the Cys sulfhydryl (—SH) group. Alternatively, other —SH containing residues (ex: cysteamine or homocysteine) can be substituted for cysteine in order to provide an alternative conjugation moiety. The advantages of these modifications will be discussed below.

Finished peptidyl-resins were dried in vacuo and then placed in the reactors of a Biosearch HF cleavage apparatus or a Peninsula Laboratories Type I HF apparatus. Peptides were cleaved from the resin using standard HF procedures. After HF removal in vacuo, the resin was washed well with diethyl ether and the peptide then extracted from the resin with trifluoracetic acid (with subsequent precipitation of the peptide via the addition of diethyl ether) or with 10–30% aqueous acetic acid (with subsequent lyophilization).

Synthetic peptides purified by reverse phase high performance liquid chromatography (HPLC) were processed on a Waters Delta-Prep 3000 preparative chromatography system (47 mm×30 cm Delta-Pak radial compression cartidge containing 300 Angstrom, 15 µm $C_{18}$) equipped with a variable wavelength detector. Typically, peptides were eluted over a 40 minute period with a linear acetonitrile gradient (0%–100%) containing a constant concentration of trifluoroacetic acid (0.1% v/v). The purification was monitored at 215 nm and the homogeneity of purified material was established by analytical HPLC on a Waters Delta-Pak $C_{18}$ column (300 Angstrom, 15 µm $C_{18}$; column dimensions: 3.9 mm ×30 cm) using the same gradient.

Amino acid analyses of synthetic peptides were obtained using the Waters PICO-TAG Chemistry (Bidlingmeyer, B.

A., et. al., *J. Chrom.*, 336, 93–104 (1984)) which involves vapor-phase hydrolysis of peptides with constant boiling 6 M HCl, derivatization of the liberated amino acids with phenylisothiocyanate (PITC) and separation/quantitation of the resulting phenylthiocarbamyl (PTC)-amino acids by reverse phase chromatography on a Waters PICO-TAG $C_{18}$ column (5 μm $C_{18}$; column dimensions: 3.9 mm×15 cm). The amino acid analysis of any purified peptide was consistent with its proposed sequence (accuracy of integrations: ±5%).

Example 3

Epitopes—Proteins a. Epitope Mapping

Epitope mapping relates to the characterization of specific regions of a protein that are being recognized by the immune system. It is unlikely that peptide residues in the "core" of a globular protein are being recognized by the immune system at least as far as the development of a humoral response is concerned. As a result, the surface map of a protein with respect to the different epitopes can be used to design and synthesize peptides that can be incorporated into the desired array. An example of this type of epitope mapping is illustrated by the identification of the histone antigen recognized by the NZB/NZW mouse.

In order to suppress the autoimmune response to histone H2B that occurs in the (NZBxNZW) $F_1$ murine model of systemic lupus erythematosus (SLE), the antibody binding domain(s) of histone H2B had to be identified. This identification process, referred to herein as "epitope mapping", involves the synthesis of various overlapping peptide fragments which are subsequently analyzed to establish regions of antigenicity. Clearly, the study of the entire H2B structure (125 amino acids) would require a very large amount of peptide synthesis. However, it is known from studies of SLE patients and mice with lupus-like disease that removal of the H2B N-terminal region with trypsin results in a loss of antigenicity (Portanova, J. P., et. al., *J. Immunol.* 38, 446–457, (1987)). Attention was, therefore, focussed on the synthesis of peptides derived from this region of histone H2B. The peptides synthesized together with their respective designations are shown in Table 2 below.

Sera obtained from (NZBxNZW) $F_1$ mice that were reactive to the N-terminal 30-mer (=Lupus 7') of H2B were also found to bind strongly to the peptide consisting of the first 15 amino acid residues (=Lupus 2') but not to peptides consisting of more internal regions (i.e. Lupus 3', 4' or 5'). Further characterization of the autoantigenic region of H2B involving peptides truncated from the N-terminus (= N-Ac-[Lupus 2'(6-15, 5-15, 4-15, 3-15 and 2-15]-CONH$_2$) and from the C-terminus (=N-Ac-[Lupus 2'(2-12, 2-10 and 2-8]—COHN$_2$) resulted in it being possible to assign the antigen recognized by (NZBxNZW) $F_1$ mice as being within H2B residues 3–12.

TABLE 2

Histone H28 Peptides
Synthesized for Epitope Mapping

Pro-Glu-Pro-Ala-Lys-Ser-Ala-Pro-Ala-Pro-Lys-Lys-
Gly-Ser-Lys-Lys-Ala-Val-Thr-Lys-Ala-Gln-Lys-Lys-
Asp-Gly-Lys-Lys-Arg-Lys-Ala-Tyr-Cys-CONH$_2$ =
Lupus 7'.

TABLE 2-continued

Histone H28 Peptides
Synthesized for Epitope Mapping

Pro-Glu-Pro-Ala-Lys-Ser-Ala-Pro-Ala-Pro-Lys-Lys-
Gly-Ser-Lys-Gys-CONH$_2$ = Lupus 2'.

N-Acetyl-Cys-Ala-Pro-Lys-Lys-Gly-Ser-Lys-Lys-Ala-
Val-Thr-Lys-Ala-Gln-Lys-CONH$_2$ = Lupus 3'.

N-Acetyl-Ala-Pro-Lys-Lys-Gly-Ser-Lys-Lys-Ala-Val-
Thr-Lys-Ala-Gln-Lys-Cys-CONH$_2$ = Lupus 4'.

N-Acetyl-Cys-Lys-Ala-Val-Thr-Lys-Ala-Gln-Lys-Lys-
Asp-Gly-Lys-Lys-Arg-Lys-CONH$_2$ = Lupus 5'.

N-Acetyl-Ser-Ala-Pro-Ala-Pro-Lys-Lys-Gly-Ser-Lys-
CONH$_1$ = N-Ac-[Lupus 2'(6–15)]-CONH$_2$ N-Acetyl-Lys-Ser-Ala-Pro-Ala-Pro-Lys-Lys-Gly-Ser-
Lys-CONH$_1$ = N-Ac-[Lupus 2'(5–15)]-CONH$_1$ N-Acetyl-Ala-Lys-Ser-Ala-Pro-Ala-Pro-Lys-Lys-Gly-
Ser-Lys-CONH$_2$ = N-Ac-[Lupus 2' (4–15)]-CONH$_1$ N-Acetyl-Pro-Ala-Lys-Ser-Ala-Pro-Ala-Pro-Lys-Lys-
Gly-Ser-Lys-CONH$_2$ = N-Ac-[Lupus 2' (3–15)]-CONH$_1$ N-Acetyl-Glu-Pro-Ala-Lys-Ser-Ala-Pro-Ala-Pro-Lys-
Lys-Gly-Ser-Lys-CONH$_2$ = N-Ac-[Lupus 2'(2–15)]-CONH$_2$ N-Acetyl-Glu-Pro-Ala-Lys-Ser-Ala-Pro-CONH$_1$ =
N-Ac-[Lupus 2'(2–8)]-CONH$_2$ N-Acetyl-Glu-Pro-Ala-Lys-Ser-Ala-Pro-Ala-Pro-
CONH$_2$ = N-Ac-[Lupus 2'(2–10)]-CONH$_2$ N-Acetyl-Glu-Pro-Ala-Lys-Ser-Ala-Pro-Ala-Pro-Lys-
Lys-CONH$_2$ = N-Ac-[Lupus 2'
(2–12)]-CONH$_2$ N-Acetyl-Glu-Pro-Ala-Lys-Ser-Ala-Pro-Ala-Pro-Lys-
Lys-Gly-Glu-Cys(Acm)-COOH,
N-Ac-[Lupus 2'(2–13)]-Glu-Cys(Acm)-COOH N-Acetyl-Glu-Pro-Ala-Lys-Ser-Ala-Pro-Ala-Pro-Lys-
Lys-Gly-Glu-Glu-Cys(Acm)-CONH$_2$,
N-Ac-[Lupus 2'(2–13)]-Glu-Glu-Cys(Acm)-CONH$_1$ The peptide chosen to be incorporated into a suppressive conjugate obviously had to include enough immunological "information" to be recognized by the murine immune system but also had to address the net positive (charge) character of residues 3–12. In order to accomplish this, N-Ac-Glu$^2$, which is not required immunologically, was included as were two non-histone C-terminal glutamic acid (Glu) residues. To the now "charge-balanced" peptide was added glycine, a residue also not required immunologically but which provided space between those elements included purely for charge-balancing purposes (i.e. -Glu-Glu) and those required for immunological recognition (i.e. residues 3–12). The final target peptide, designated N-Ac-[Lupus 2'(2-13)]-Glu-Glu-Cys-CONH$_2$ (see Table 2), was then used for conjugation.

As mentioned above, highly cationic epitopes may need to be compensated for, particularly when they are arrayed in a multivalent way. In this case, such compensation was effected by adding additional anionic amino acids to the defined epitope. As an alternative, an anionic scaffold could have been used. In either case, the desired outcome is to have an overall charge neutral or slightly anionic construct so as to avoid non-specific adherence of these compounds to anionic surfaces such as cell membranes.

The antigenic facade of the H2B histone protein consists of a single continuous peptide sequence that was capable of accommodating the entire population of antibodies generated by a population of mice. And, while each individual mouse recognized a discrete region within the entire epitope, the entire population of mice could be dealt with using a single peptide ligand. This is unlikely to be the rule for other proteins such as Ragweed antigen E where multiple discrete epitopes are more likely to be encountered. Again, a certain amount of microheterogeneity within a population with respect to a given epitope is likely; no single epitope can be expected to predominate over all the others for the entire population.

In view of the above, one of at least two alternatives can be employed. Either multiple ligands can be synthesized and presented either as a mixture of arrays each with a specific ligand or an array of a mixture of ligands (an artificial protein from an antigenic perspective) wherein each array contains a valence-restricted representation of the relevant ligands. Another alternative is to produce valence-restricted arrays of the protein in question. Where these types of constructs are determined to be the most appropriate means for manipulating the immune response for a specific antigenic protein, the following synthetic approaches can be used.

b. Protein Oligomers as Oligovalent Heterogenous Epitope Arrays

An alternative to mapping the antigenic facade of a protein is to produce oligomeric (valence restricted) arrays of the protein in question made up of either the protein crosslinked to itself or arrayed on a different type of scaffold. This type of construct is desirable if there are a large number of discrete epitopes that are being recognized by the immune system or if some of the epitopes are formed by discontinuous conformationally constrained regions of the molecule. Two of these types of constructs have been made and have been used to verify that protein oligomers behave in accordance with the immunon paradigm. The preparation of these oligomers is described below.

(1) Polymerization of BSA and OVA

Conditions were established that allowed the polymerization of either BSA or of OVA to give polymers, in substantial yields, ranging from dimers to very high polymers, all of which were water soluble and time stable. The properties of water solubility and time stability were particularly important because of the prolonged subsequent fractionation of the polymers on gel filtration columns, a procedure which produced narrow fractions of definable degrees of polymerization. BSA was polymerized to itself through the use of a water soluble carbodiimide, 1-ethyl-3-(3-dimethylaminopropyl)carbodiimide, a reagent which links a free carboxyl group on one molecule to a free amino group on a neighboring molecule through an amide bond. OVA was polymerized to itself by the use of glutaraldehyde, a reagent which links a free amino group on one molecule to a free group on a neighboring molecule.

(2) Fractionation Procedure

The protein monomers, oligomers and polymers, which were produced during the chemical cross-linking steps described above, were subjected to fractionation and repeated re-fractionation on a series of gel filtration columns until they demonstrated narrow molecular weight distributions, as measured by HPLC analysis. The molecular weight for each fraction was then determined by the use of the Model E analytical ultracentrifuge under equilibrium conditions. During this prolonged series of slow fractionation steps, molecules which were unstable to any of the many steps involved in processing, handling, or storage were fractionated away from the samples, yielding a series of preparations, each of which contained a relatively narrow range of molecular sizes of substantial time stability. These water soluble preparations were then injected into mice intra-peritoneally, without the use of any adjuvant, in order to determine their relative immunogenicity. The level of immune response was determined by measuring serum IgM or IgG antibody levels against BSA or OVA by standard solid state ELISA technique.

Alternatively, the desired protein can be biotinylated in such a manner that only one biotin moiety is incorporated per protein monomer. This can be accomplished by reacting a significant molar excess of the protein monomer in dilute solution with a modified biotin molecule capable of reacting with either free amines or carboxyl groups on the protein. These conditions yield a predominance of "mono-functionalized" protein molecules with a minimum of multiply derivatized protein monomers. These biotinylated proteins can then be arrayed in a rigorously tetravalent fashion with streptavidin with any polymeric constructs removed by size exclusion chromatography.

Similar "mono-functionalization" of a protein ligand can be achieved using many different chemistries with the functionalized protein then being arrayed on a valence restricted scaffold to achieve the same endpoint. These valence restricted arrays can then be used to manipulate the immune system in the desired fashion.

Finally, as previously mentioned, epitopes represented by well defined protein domains or whole proteins can be incorporated into genetically engineered constructs having the desired valence for use as either a portion of or as a completely independent valence restricted array.

C. Mimotopes

Immunoglobulins and their related surface bound receptors are predominantly concerned with the physical structure (shape, hydrophobicity or hydrophilicity, hydrogen bond donor or acceptor groups, etc) and charge of the antigen in question. The specific "content" of the antigen with respect to peptide sequence, carbohydrate content, etc. is only significant as it contributes to the "fit" of the ligand to the receptor. As a result, there has been a considerable amount of work at a number of different laboratories directed at developing methodologies that allow one to generate a multitude of randomly synthesized ligands that can be screened for their ability to "fit" a desired receptor. The relationship of a ligand identified in this manner to the "natural" ligand to which the immune system's response is directed is limited solely to their structural similarity. Such a ligand has been given the term "mimotope" to represent the ability of this type of ligand to mimic a naturally occurring epitope.

One skilled in the art will appreciate that mimotopes can be modified to enhance their binding to the targeted receptor population using standard chemical modification techniques and substitutions. Mimotopes generated by a random process may require modification prior to their being conjugated to a scaffold to yield an agonist or antagonist array.

Example 4

Epitopes—nucleic Acids a. Size-fractionated Naturally Occurring DNA

Salmon testes DNA (Sigma) was digested with *Aspergilus oryzae* S1 nuclease (Pharmacia) in order to eliminate "nicked" DNA. The product of this reaction was then subjected to partial digestion with bovine pancreatic Deoxyribonuclease I (BRL Gibco) in the presence of manganese ions. In the presence of manganese ions, bovine pancreatic DNase I cleaves both strands of a DNA duplex at approximately the same site to yield fragments of DNA that are blunt-ended or have protruding termini only one or two nucleotides in length (Melgar and Goldthwaite, 1968). After cleavage with DNase I, the 5' ends of the DNA retain the phosphate groups. The product of the DNase I reaction was then size-fractionated on a 5 cm×92 cm Biogel A-1.5 m (fine mesh, Bio-Rad) column. The column was eluted with 150 mM NaCl, 50 mM Tris HCl pH 7.2, 1 mM EDTA. Fractions were collected and aliquots of the fractions analyzed by polyacrylamide gel electrophoresis. Fractions that contained DNA of approximately 60 to 120 nucleotides in length were pooled and the DNA recovered by ethanol precipitation. The concentration of the DNA was determined by measuring the $OD_{260}$, where 1 $OD_{260}$ equals 50 μg/ml double-stranded DNA. This DNA was then modified for conjugation in the following manner.

Provided as the bis-5'-phosphate, the DNA (0.64 μmole) was converted into the bis-5'-(1-methyl)phosphorimidazolide with EDC (0.15 M) in 1-methylimidazole buffer (0.1 M pH 6). Subsequent coupling to (S-3-nitro-2-pyridinesulfenyl)-cysteamine ((S-Npys)-Cmn, 0.2 M) then afforded the bis-phosphoramidate; i.e. the conjugatable (following deprotection) form of the DNA. Removal of excess (S-Npys)-Cmn and isolation of the derivatized DNA was accomplished by repetitive precipitation from absolute EtOH.

b. Synthetic DNA

Alternative synthetic efforts designed to provide "conjugatable" synthetic DNA have focused on the 5'-length derivatization and eventual conjugation of synthetic DNA 40 nucleotides in length. DNA was synthesized using β-cyanoethyl phosphoramidite chemistry on an Applied Biosystems model 381A DNA synthesizer using the manufacturer's chemicals and protocols. Some of the oligonucleotides were synthesized with an amino group at the 5' end. This amino group was derived from a commercial DNA synthesis reagent, Aminolink 2 (Applied Biosystems). The Aminolink 2 reagent was used according to the manufacturer's recommended protocols. After removal from the solid support and deprotection according to the manufacturer's protocols, the DNA was purified by gel filtration on a 1.6 cm×16 cm column of Sephadex G-50 (fine mesh, Pharmacia). The column was eluted with 0.5 M $NH_4OH$. Fractions were collected and those fractions containing the DNA were pooled and lyophilized. The DNA was resuspended in water and the concentration determined by measuring the $OD_{260}$. For single-stranded DNA, 1 $OD_{260}$ equals 40 μg/ml DNA. Derivatization is carried out with one of two activated S-containing amino acids: N-acetyl-S-Npys-L-cysteine-N-hydroxysuccinimide ester or N-(succinyl-N-hydroxysuccinimide ester)-S-Npys-cysteamine.

A reactive primary amino group can also be incorporated at the 5'-end of the synthetic DNA 40-mer via coupling of a modified nucleotide available from Glen Research. This nucleotide, a modified thymidine, contains a trifluoroacetylated primary amine attached to the base moiety by a 10 atom spacer group. As an alternative to the Aminolink approach, this method (of amine incorporation) has the advantage of verification of-incorporation of the nucleotide bearing the protected amino group (via standard DNA calorimetric coupling assays). Chemical 5'-phosphorylation of synthetic DNA is also possible and yields DNA that is functionally identical to the size-fractionated DNA described above except that the resulting DNA is monofunctionalized. Preparing this type of synthetic DNA for conjugation, i.e. coupling of (S-Npys)-Cmn and subsequent disulfide reduction, is accomplished as described in section a. above. Those skilled in the art will realize that phosphorothioate-containing DNA, and endo- and exonuclease resistant form of DNA, is equally accessible via solid phase DNA chemistry and can be modified by the same techniques (described above) to generate conjugatable nucleic acid.

In all cases, the DNA intended for conjugation is derivatized with a protected thiol-containing moiety that when deprotected and reacted with maleimide containing scaffolds will conjugate to the scaffold in a manner analogous to the thiol-containing peptides described above. In addition, these modified DNA analogues now contain a residue that can be used to unambiguously confirm and quantitate covalent attachment of the DNA to the desired scaffold.

Example 5

Conjugates

A. Conjugate Synthesis

While the use of various types of sulfur based chemistries are specifically described herein, these chemistries are but a small sampling of the types that can be used for linking ligands and scaffolds. The types of chemistries that can be employed for providing "spacer arms" to reduce any steric interactions between the scaffold and ligand or alternative conjugation chemistries for any particular application can be extrapolated from the foregoing disclosure. As long as the fundamental rules of valence and/or size are maintained and the ligand can interact with the targeted receptor, any chemistry or geometry of scaffold and ligand is acceptable. Some of the chemistries that have been employed to extend the immunon paradigm to the full range of immune responses are described below.

a. Small Molecular Weight Haptens

As mentioned below, the small molecular weight haptens chosen for investigation all included reactive groups that allowed for easy covalent attachment to the desired scaffolds. All of the conjugations were done in aqueous solution and the unconjugated small molecular weight haptens removed by dialysis, ultrafiltration or size exclusion chromatography.

b. Peptides

Figure 8:
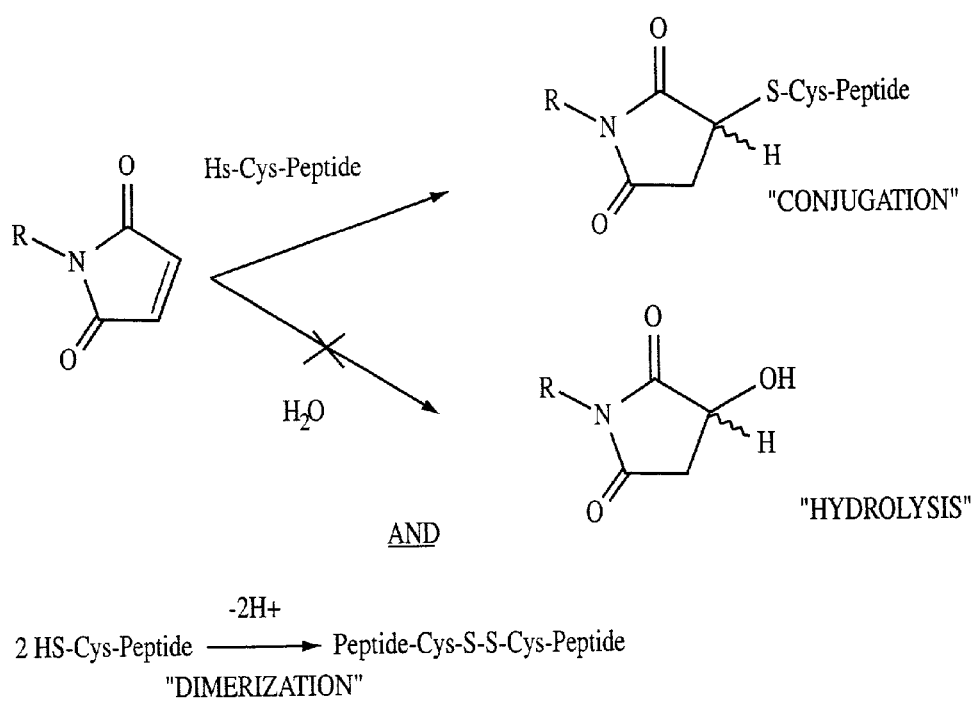
FIG. 8. Conjugation of peptides to GMB-dextran.

The reaction between a cysteine (Cys)-containing peptide and GMB-dexamine (4) is but one example of the well-known tendency of thiol (—SH) nucleophiles to react with α, β-unsaturated carbonyl systems. This reaction is referred to as conjugate- or 1,4-addition and is used for the covalent attachment of peptides to dextran (FIG. 8). Those skilled in the art will recognize that alternative conjugation chemistries can be employed to accommodate any particular set of combinations of backbone or hapten. Alternative chemistries that take advantage of a reactive thiol include reactions with haloalkanes or haloacetamides. All such reactions involve a freshly-reduced buffered solution of a peptide bearing an N- or C-terminal Cys residue and freshly-prepared GMB-dexamine (4). C-Terminal Cys-containing peptides used in conjugation reactions were routinely purified to analytical purity by preparative HPLC prior to conjugation. Although N-terminal Cys-containing peptides may not need to be purified prior to their conjugation and can, in fact, be used after only standard post HF cleavage extraction steps have been carried out, these peptides were also purified prior to their conjugation.

While the reaction of a Cys-containing peptide with GMB-dexamine (4) is an extremely rapid process ($t_{1/2}$<5 minutes for peptides conjugated at pH 5–7 in PBS, $t_{1/2}$=0.7 sec for the reaction of cysteine and N-ethylmaleimide at pH 7 in acetate buffer), there is one distinct competing reaction that occurs whenever a free sulfhydryl (Cys)-containing peptide and GMB-dexamine (4) are mixed together (in PBS, for example), i.e. the dimerization of the peptide to yield an unreactive disulfide. These two processes: conjugation and dimerization occurring simultaneously effect the ultimate conjugation yield and, hence, the density of conjugated peptide as well. The maleimide functional group has been observed to be extremely stable over the pH range of the conjugation reaction (pH 5–7). Specifically, the succinimido-form of dexamine produced by hydrolysis of the maleimide double bond could not be detected after 2 days of exposure of GMB-dexamine (4) to typical conjugation reaction conditions. Therefore, the hydrolysis of GMB-dexamine (4) does not appear to be a factor (i.e. a side reaction) influencing conjugation yield.

Cysteine (Cys)-containing peptides and GMB-dexamine (4) were prepared as described above. Reductacryl resin (immobilized Cleland's reagent=dithiothreitol (DTT)) was obtained from CALBIOCHEM Corp. with a reduction capacity of ca. 0.5 meq/g. Phosphate-buffered saline (PBS) used in reduction of Cys-containing peptides and in conjugation reactions was prepared as described above.

Purified peptides bearing N- or C-terminal Cys residues were dissolved in PBS at concentrations up to 3 mg/mL. The peptide solution was then added to a 50-fold molar excess of reductacryl resin (DTT equivalents) in a glass reaction vessel equipped with a cinder glass bottom and a nitrogen (gas) inlet. Reduction of the peptide was carried out for 30–45 minutes at room temperature with gentle mixing of the reaction mixture promoted by nitrogen bubbling. The fully-reduced Cys-containing peptide was then added slowly to a freshly-prepared solution of GMB-dexamine (4) in PBS and the resulting conjugation reaction allowed to proceed for 2 hours at room temperature (reaction pH 5–7). Since many conjugation reactions were carried out with sub-maximal levels of peptide, all were routinely quenched for 24 hours with a ten-fold molar excess of mercaptoethanol (ME) relative to (dex)amine content. This precaution prevents the addition of unwanted peptides/proteins to the conjugate during its in vivo lifetime or crosslinking of conjugate to each other or to other macromolecules during purification, storage or use. Depending on the need for greater anionic character in the final conjugate, mercaptoethanol can be replaced with either mercaptoacetic acid (MAA) or mercaptosuccinic acid (MSA) which introduce one or two equivalents of negative charge, respectively, for each maleimide group. Purification of peptide-dextran conjugates:

Peptide-dextran conjugates present in the quenched reaction mixtures were purified/isolated by either extensive dialysis or ultrafiltration against PBS. Such treatment effectively removes mercaptoethanol or other quenching reagent and unconjugated peptide from the finished conjugate. With regard to the latter type of reaction "contaminant", the hypothesis that noncovalently-associated peptide should not contribute significantly to either the immunogenicity or to the immunosuppressive nature of a conjugate is reasonable when one considers what is expected of a conjugate in the context of the Immunon model of immune response. In the absence of some type of covalent attachment "indicator", however, noncovalently-associated peptide can result in significant overestimation of the conjugate peptide substitution density, a quantity of great practical significance. An "unambiguous" indicator of covalently-bound conjugate peptide has been found (S-2-(2R,2S-succinyl)-L-Cys) and is discussed in greater detail below. Not addressed by either dialysis or ultrafiltration is the removal of high molecular weight (i.e. significantly greater than that of the desired conjugate) material from a finished peptide-dextran conjugate. Preliminary data indicate that, when present, high molecular weight material is often only a very slight contaminant, i.e. the conjugates are largely monomeric. (Because the observation of high molecular weight material was made by laser light scattering analysis, it is not possible to establish the exact extent of the contamination).

Quenched conjugation reaction mixtures were transferred in toto to 12,000–14,000 mwco dialysis tubing and then dialyzed against PBS according to the following schedule: 24 hours against PBS containing ca. 0.02% (w/v) $NaN_3$ (2 PBS changes), 24 hours against PBS (3 PBS changes) and then 24 hours against one-tenth strength (i.e. 15 mM NaCl and 1 mM phosphate, pH 7.3–7.4) PBS (3 PBS changes). Ultrafiltration was carried out in an Amicon 8200 ultrafiltration vessel equipped with either a 5,000 or 10,000 mwco filter as follows: The conjugation reaction mixture was diluted to 200 mL total volume with PBS that contained ca. 0.02% (w/v) $NaN_3$ and then concentrated down to a volume$\leq$30 mL at 55 psi (nitrogen pressure). The process was then repeated two times with PBS and two times with one-tenth strength PBS. Following the completion of dialysis or ultrafiltration, purified peptide-dextran conjugate was aliquotted into polypropylene-polyethylene vials, frozen and lyophilized. Finished conjugates were stored at –20° C. in lyophilized form.

c. Nucleic Acids

As discussed above, the DNA used for conjugation is modified in such a manner that it will behave similarly to peptides when conjugated. Discussed below are some of the methods by which either the size fractionated DNA or the synthetic DNA is attached to the desired scaffold.

(1) Natural DNA

Deprotection of the DNA, i.e. removal of the S-Npys group, is carried out via exposure to Reductacryl resin for 1 hour in 1 mM EDTA/1 M NaCl-containing 1-methylimidazole buffer (0.16 M, pH 6). The (now) thiol-containing DNA was then added directly into a solution of GMB-Dex (5 mg) to generate a DNA/Dex conjugate. Following quenching with L-Cys and reduction of the reaction volume by ultrafiltration, the conjugate is purified by preparative gel filtration on Sephacryl S-400 HR. Size-exclusion HPLC chromatography of the purified conjugate on a TSK 5000 (Toso Haas) column indicated that complete removal of uncoupled DNA had been achieved by the gel filtration step. The use of bis-thiol functionalized DNA made the production of oligomers (dextran molecules cross-linked with DNA) a likely possibility, and the presence of oligomer in the concentrated conjugation reaction mixture was apparent during preparative gel filtration. Although not completely resolved from the DNA/Dex "monomer" peak, this "contaminant" can be removed from the desired conjugate if fractions were combined conservatively.

For valence calculation purposes, if it is assumed that bis-functionalization of the DNA with reactive thiol (—SH) groups resulted in the production of "looped" DNA structures on the dextran surface, then the quantitated amount of succinyl-cysteamine (Succ-Cmn) established by amino acid analysis will indicate one-half the amount of covalently-attached DNA. The conjugation chemistry described above appears to result in ca. 6–8 moles of "looped" DNA per mole of $Dex_{70K}$.

In the course of preparing the size-fractionated DNA-dextran conjugate, care was taken (in the form of excess Cys addition) to remove any trace of unreacted maleimide present on the GMB-dexamine. Furthermore, as mentioned above, the high molecular weight species present (i.e. oligomer) during preparative gel filtration was removed via conservative fraction combining. It was found, however, that upon standing at 4° C. the purified conjugate converted almost completely to the higher molecular weight oligomer. Since disulfide (—S—S—) dimers are likely to accompany any reaction process involving bis-thiol-functionalized molecules and are the presumed source of the oligomer removed during the preparative gel filtration, the most likely explanation for the observed molecular weight shift is a continuation of the (presumed) disulfide formation process. Consistent with this hypothesis was the finding that purified conjugate responded to exogenously added DTT in the predicted manner, i.e. essentially a complete regeneration of the desired lower molecular weight conjugate.

Furthermore, size-fractionated DNA-dextran conjugate that had been prepared months earlier and stored continuously at 4° C. responded to DTT but the rate of the reaction was much slower than that associated with freshly-prepared conjugate. These results are consistent with a more highly cross-linked (via disulfide bonds) preparation of conjugate developing as a result of long storage. In order to prevent the reformation of disulfide bonds (inter-dextran), DTT reduction was accompanied by S-alkylation with excess maleimide.

Clearly, the tendency of this type of conjugate (or any type for that matter) to undergo a shift in molecular weight could significantly confound efforts to preare and administer an immunosuppressive agent. This example underscores the importance of completely characterizing conjugate material prior to its administration.

(2) Synthetic DNA

Following the isolation of modified (i.e. SH-containing) DNA, deprotection and conjugation is carried out as described above for size-fractionated DNA. Single stranded DNA-containing (dextran) conjugate is then exposed to the complimentary DNA strand (also 40 nucleotides in length) to afford the double stranded DNA-containing (dextran) conjugate. It is at this point that efforts to stabilize the resulting DNA duplex can be undertaken. Both the highly specific reagents: mitomycin C and the less specific psoralen can be used to cross-link the individual strands of the dextran-bound DNA duplex in an attempt to decrease the rate of exonuclease and (perhaps) endonuclease digestion. Such a decrease would presumably result in a longer duration of action of the DNA-Dex conjugate and could, therefore, also result in lower doses of the conjugate being required for therapeutic intervention.

Alternatively, chemically modified DNA analogues such as phosphorothioates can be utilized. These nucleic acid analogues are known to be resistant to endonuclease and exonuclease digestion.

B. Analysis

In all cases the resulting conjugates are subjected to rigorous analysis with respect to both content and overall structure so as to assure the final product meets the criteria established for agonist or antagonist arrays as desired. Described below are representative analytical procedures for conjugates in general (haptens, peptides and nucleic acids) and the specific peptide containing conjugates used in the Examples set forth herein.

(a) Fractionation and Characterization of Haptenated Polymers:

All of the procedures utilized for the preparation of hapten- or epitope-arrayed conjugates described above generated predominately haptenated polymers of the desired molecular mass and degree of hapten substitution. However, there was invariably present a substantial amount of material of higher molecular mass, which had been generated by a small degree of unavoidable cross-linkage occurring between polymer molecules, due to side reactions. It was therefore necessary to purify the haptenated or epitope-substituted polymer preparations further, by repeated size fractionation on gel filtration chromatography columns as described above, before they were homogeneous enough in molecular size (mass) for further chemical or physical characterization, and for use in immunological studies.

Compositional Analysis of Haptenated Polymers:

i) Dry Weight Analysis

The primary analytical reference standard for each type of polymeric material was a dry weight analysis for the actual amount of polymer mass present in a given type of polymer preparation. Dry weight was determined after the thorough vacuum drying of polymer samples and appropriate dialysate samples.

ii) Spectral Analysis

The haptens used in these studies were chosen, in part, so that they had identifiable spectral absorption bands at wavelengths in the visible or near ultraviolet regions. The amount of hapten chemically coupled to polymer molecules in a preparation was usually determined from the comparison of the optical absorption due to the hapten groups and the total mass of the polymer preparation, as determined by dry weight analysis or refractive index increment analysis.

iii) Chemical Analysis

It was sometimes possible to measure the quantity of a certain type of chemical group present on polymer molecules by direct chemical analysis. Amino groups were often measured by reaction with trinitrobenzenesulfonic acid, yielding a colored product which could then be measured by spectrophotometric analysis. Carbohydrate could be determined by reaction with sulfuric acid and phenol, to give colored products having measurable optical absorption. The benzyl penicillin hapten could be measured by reaction with a mercurial compound to give colored products. Peptide and/or protein containing conjugates can be characterized by amino acid analysis (see below).

iv) Refractive Increment Analysis

By the careful calibration of the refractive index increment due to the polymer against the dry weight measurement for each type of polymer molecule, it was possible to substitute refractive index increment measurement for dry weight measurement. This procedure has greatly increased the accuracy of measurement of polymer mass by permitting sensitive and accurate measurement of the mass of the polymeric materials during HPLC measurements on size exclusion columns.

v) Titration Analysis

Chemical groups with ionization constants near the neutral range, such as carboxyl, amino and phenolic groups, could be measured directly by means of acid-base titration. This procedure was especially important for the measurement of carboxyl group content, since the carboxyl group is very difficult to measure by spectrophotometric means in aqueous solutions of polymers. Such measurement of ionizable chemical groups is especially important in determining the net electrical charge on large polymer molecules, a parameter which affects the interaction of the polymer molecules with electrically charged cell surfaces.

(b) Determinations of the Molecular Mass and Size of Haptenated Polymer Preparations:

i) Size Exclusion Chromatography (SEC)

Use of SEC methods permit the convenient determination of relative molecular mass by comparison of the chromatographic column retention times of unknown samples and homogeneous standard, samples using standard HPLC techniques. The standardization polymer materials have to be relatively homogeneous and independently calibrated for molecular mass by some absolute experimental procedure, such as equilibrium ultracentrifugation or low angle laser light scattering. Because the SEC method is very sensitive to any physical interactions between the column support and the polymer molecule, the column retention times must be calibrated for each and every type of haptenated polymer molecule. Such calibration is sensitive to the physical and chemical nature of the polymer molecule, the chemical nature and number of haptens, the net electrical charge on the molecule, etc.

ii) Equilibrium Analytical Ultracentrifugation

Figure 9:
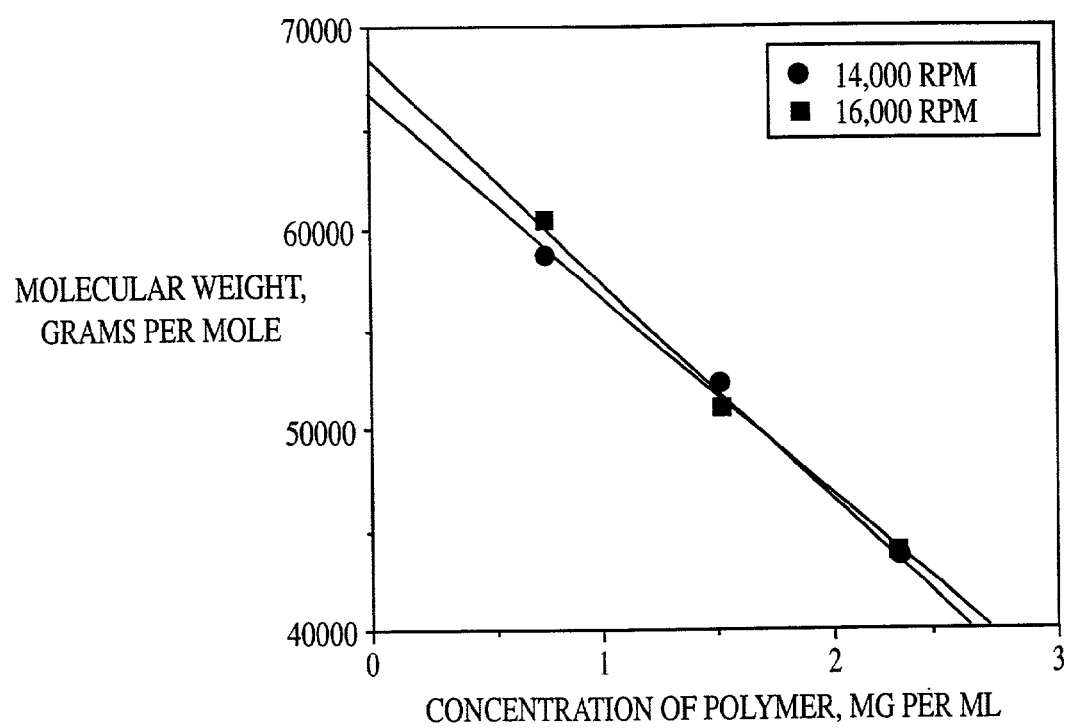
FIG. 9. Analytical equilibrium ultracentrifugation of fluoresceinated dextrans.

When appropriately combined with another experimentally measurable quantity—the partial specific volume, short column equilibrium analytical ultracentrifuge measurements yielded the absolute weight-average molecular weight of a substantially homogeneous polymer preparation. The experimental method requires a series of measurements at several polymer concentrations followed by the extrapolation of the results to zero polymer concentration. Equilibrium measurements are made at different centrifuge speeds of rotation, in order to demonstrate the relative independence of the extrapolated molecular weight on rotor speed. FIG. 9 illustrates for a particular fluorescein-dextran sample the determination of molecular weight as determined at two different rotor speeds, (14,000 and 16,000 RPM) and by extrapolation to zero polymer concentration. In this case the weight average molecular weight of the haptenated polymer was approximately 68 kDa.

iii) Low Angle Laser Light Scattering

When appropriately combined with an experimentally determined refractive index increment, low angle light scattering methods yield a value for the absolute weight average molecular weight of a polymer preparation. For large molecules, the method requires measurements at a number of concentrations and angles, followed by extrapolation both to zero polymer concentration and to zero angle of measurement.

If combined with the separation of molecules of different molecular sizes using SEC, this light scattering method yields a dependable determination both of the molecular mass and physical size distributions in a very small quantity of polymer preparation. Measurements of this type were routinely carried out using a high pressure liquid chromatography apparatus, Hewlett-Packard HP1090M, and a low angle laser light scattering device, Wyatt Technology Dawn. Size exclusion columns were Toyo Soda TSK GMPW gel columns or Pharmacia Superose 6 or 12 columns or combinations thereof, appropriately chosen to separate the molecular sizes present in the particular sample. When low molecular weight samples were inadequately separated from salt a column of Sephadex G15 was added to increase resolution. When polymers were substituted with high amounts of haptens having appreciable hydrophobic character, such as dinitrophenyl or fluorescein, there was significant interaction between the hapten and the column material, causing interference with the size exclusion based separation. When this effect occurred, it was minimized by using 20% acetonitrile in the column buffer.

Examples of the results obtained with peptide-dextran conjugates analyzed by the low angle laser light scattering method are shown in Table 3. The data show the results obtained in different runs, using different combinations of size exclusion columns. Aside from a few instances where obvious technical problems were present, the data show substantial consistency and are in general agreement with expectations for the particular samples.

TABLE 3

| Sample | Columns | Mn | Mw | Mw/Mn |
|---|---|---|---|---|
| 10 K Dexamine | SUP-6 + 12 | 12 8 K | 13 5 K | 1 05 |
| COR-3253 | GMPW + G-15 | 13 5 K | 16 1 K | 1 19 |
| | G-15 + GMPW | 10 0 K | 11 0 K | 1 10 |
| 40 K Dexamine | SUP-6 + 12 | 48 0 K | 51 2 K | 1 07 |
| COR-3254 | GMPW + G-15 | 64 4 K | 74 6 K | 1 16 |
| | G-15 + GMPW | 45 5 K | 48 2 K | 1 06 |
| 70 K Dexamine | SUP-6 + 12 | 66 1 K | 88 1 K | 1 33 |
| COR-3255 | GMPW + 2 5 K | 68 7 K | 82 6 K | 1 20 |
| | G-15 + GMPW | 62 6 K | 72 8 K | 1 16 |
| 500 K Dexamine | SUP-6 + 12 | 307 K | 440 K | 1 43 |
| COR-3256 | GMPW + 2 5 K | 403 K | 460 K | 1 14 |
| | G-15 + GMPW | 317 K | 341 K | 1 39 |
| A | GMPW + 2 5 K | 23 4 K | 30 8 K | 1 32 |
| COR-3257 | G-15 + GMPW | 22 8 K | 23 7 K | 1 13 |
| B | SUP-6 + 12 | 99 1 K | 223 K | 2 25 |
| COR-3258 | GMPW + 2 5 K | 96 1 K | 147 K | 1 53 |
| | G-15 + GMPW | 99 1 K | 141 K | 1 42 |
| C | SUP-6 + 12 | 685 K | 1 38 M | 2 01 |
| COR-3259 | GMPW + 2 5 K | 397 K | 1 04 M | 2 62 |
| | G-15 + GMPW | 586 K | 1 08 M | 1 84 |
| D | SUP-6 + 12 | 48 2 K | 59 9 K | 1 16 |
| COR-3260 | GMPW + 2 5 K | 34 1 K | 40 1 K | 1 18 |
| | G-15 + GMPW | 28 4 K | 31 0 K | 1 09 |
| E | SUP-6 + 12 | 676 M | 1 45 M | 2 14 |
| COR-3261 | GMPW + 2 5 K | 408 K | 1 05 M | 2 57 |
| | G-15 + GMPW | 557 K | 1 02 M | 1 83 |
| F | SUP-6 + 12 | 113 K | 130 K | 1 15 |
| COR-3262 | GMPW + 2 5 K | 78 4 K | 92 5 K | 1 18 |
| | G-15 + GMPW | 83 9 K | 93 2 K | 1 11 |

(c) Analysis of Peptide-dextran Conjugates:

The importance of analyzing peptide-dextran conjugates relates ultimately to the expectation that different immunological behavior will be elicited by conjugates having different peptide substitution densities. Amino acid analysis via the Waters PICO-TAG chemistry following the complete acid (HCl) hydrolysis of a peptide-dextran conjugate has been found to be a very effective method for measuring both (conjugate) peptide and carbohydrate content. Although acid hydrolysis does not permit recovery of the peptide or carbohydrate portions as intact entities, such recovery is not necessary for the evaluation of conjugate peptide substitution density. That is, simply by recovering and quantitating the amino acids derived from the conjugated peptide and GMB-dexamine it is possible to assess the moles of bound peptide and the moles of recovered dexamine, respectively.

Figure 10:
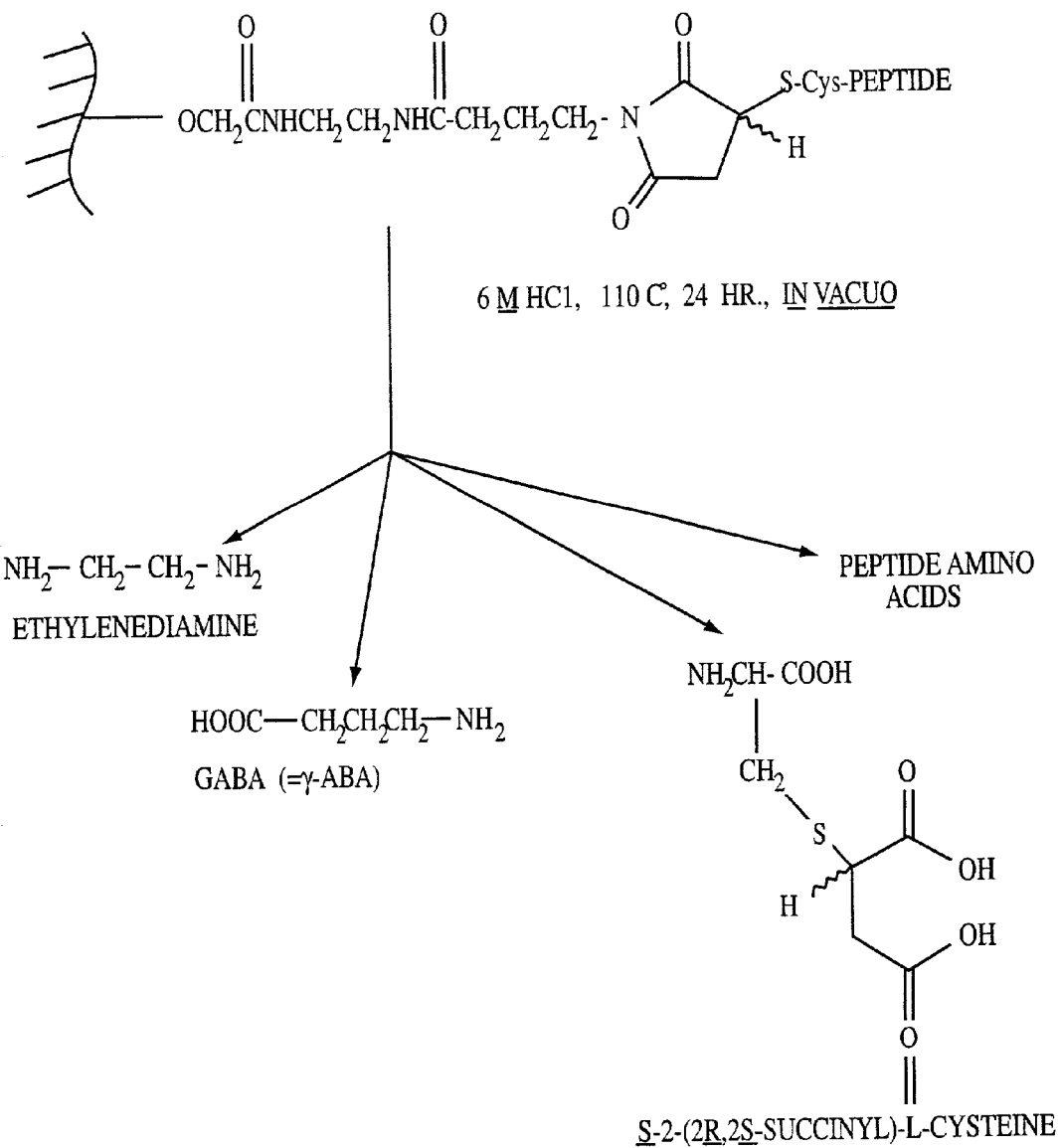
FIG. 10. Amino acid analysis of a peptide-dextran conjugate.
Figure 11:
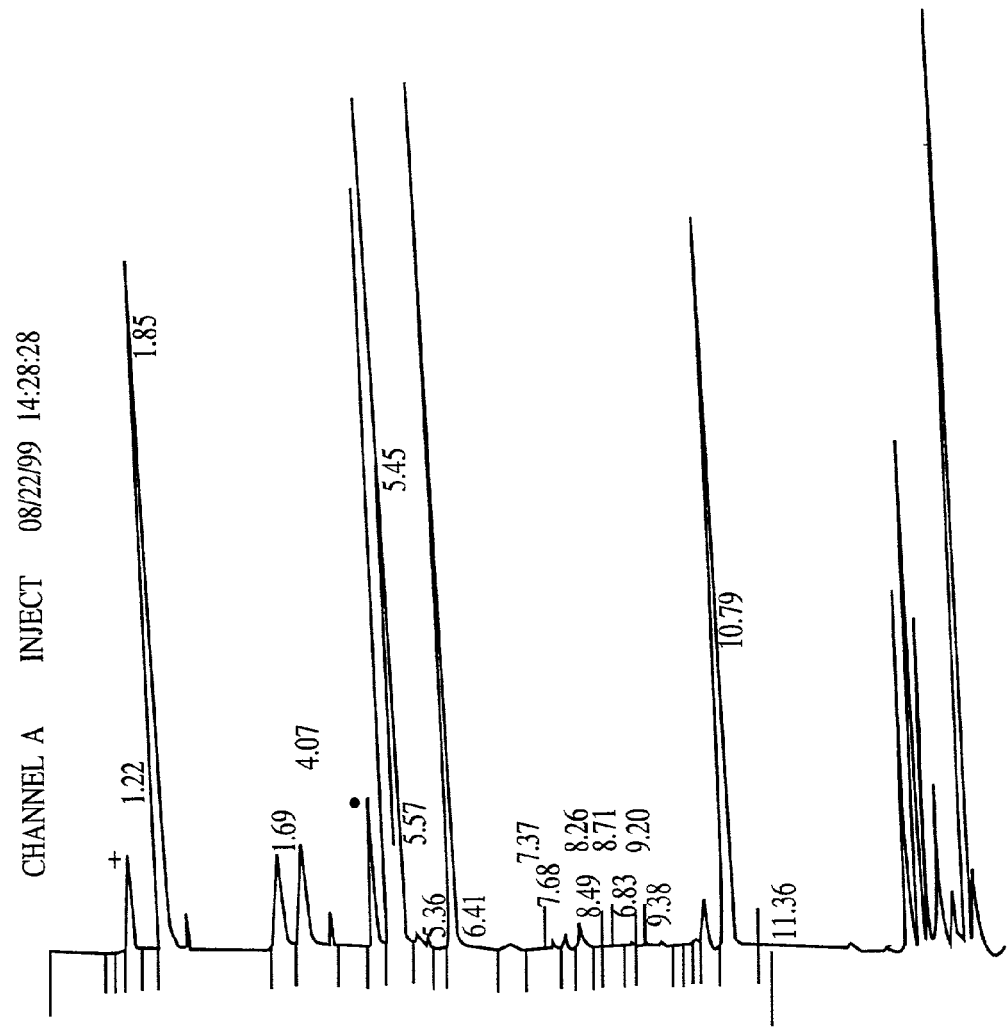
FIG. 11. Lupus histone peptide-dextran conjugate analysis.

The typical products derived from the acid hydrolysis of a peptide-dextran conjugate are shown in FIG. 10. The three components of interest are: gamma-aminobutyric acid (GABA); which indicates the maximum amount of peptide that can be conjugated covalently and which also provides a direct measure of the amount of recovered dexamine backbone, $\underline{S}$-2-($2\underline{R}$, $2\underline{S}$-succinyl)-L-Cys; which distinguishes covalently-bound from noncovalently-bound conjugate peptide (because only covalently-bound peptide is $\underline{S}$-succinylated) and the amino acids derived from the conjugated peptide. The phenylthiocarbamyl (PTC)-derivative of $\underline{S}$-2-($2\underline{R}$,$2\underline{S}$-succinyl)-L-Cys, having a retention time of 1.33 minutes on the PICO-TAG HPLC column, is well separated from any other PTC-derivative. The PTC-derivative of gamma-aminobutyric acid (PTC-GABA), however, coelutes with that of arginine (Arg). While this is inconvenient when Arg-containing peptide-dextran conjugates are being analyzed, difference analysis (i.e. pmoles @ GABA=total pmoles in peak—pmoles @ Arg) can be used to measure GABA recoveries when integral pmole values of other conjugate peptide amino acids are known. An example of the type of analytical data obtained from PICO-TAG conjugate analysis is shown in FIG. 11 which displays the HPLC chromatogram of the PTC-amino acids derived from a (lupus) histone peptide-dextran conjugate.

The importance of attending to the problem of differentiating between covalently- vs. noncovalently-bound conjugate peptide as well as to potential losses of conjugate that may occur throughout the production process is exemplified in FIG. 12. The ultimate goal of the conjugate analysis process is to measure as accurately as possible the number of peptide molecules bound per average molecule of dextran. Although the equation which yields this information is simple enough (FIG. 12), several variables effect the numerator and the denominator of this equation. Quantitation of the PTC-derivatives of S-2-(2R, 2S-succinyl)-L-Cys and GABA, however, significantly increases the accuracy of conjugate peptide substitution density measurements.

Figure 13:
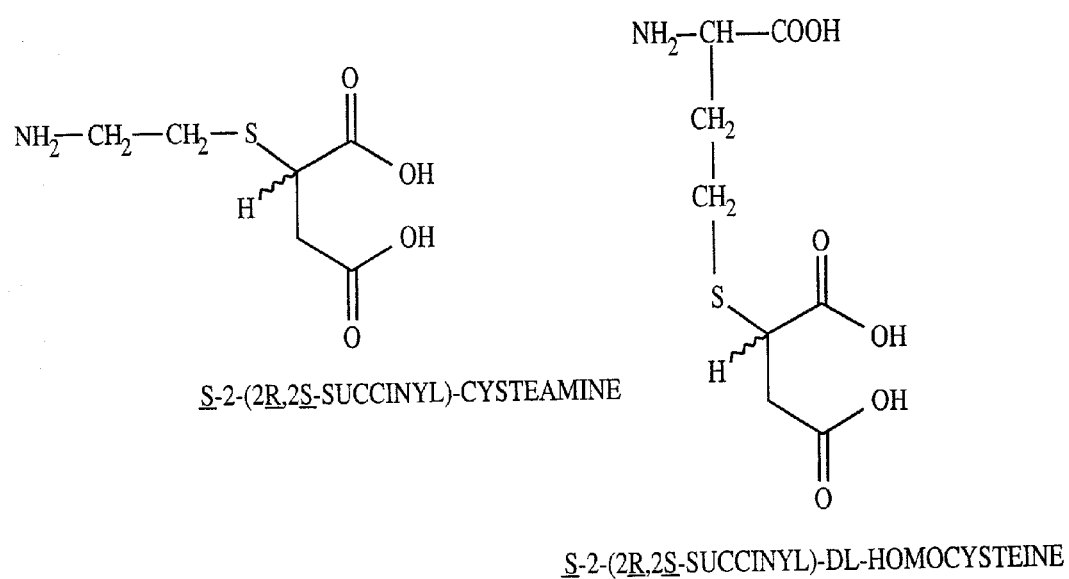
FIG. 13. Alternative marker amino acids derived from acid hydrolysis of peptide-dextran conjugates.

Although the importance of the PTC-derivative of S-2-(2R,2S-succinyl)-L-Cys cannot be overemphasized, other sulfur (S)-containing amino acids have been found which can also provide an unambiguous assessment of covalently-attached conjugate peptide. Specifically, the PTC-derivatives of S-2-(2R,2S-succinyl)-cysteamine (retention time=3.38 minutes) and S-2-(2R,2S-succinyl)-DL-homoCys (retention time=1.50 minutes) (see FIG. 13), derived from the corresponding cysteamine- or homoCys-containing peptide/GMB-dexamine conjugate, can substitute effectively for PTC-(S-2-(2R,2S-succinyl)-L-Cys. The ability to generate and quantitate three different sulfur (S)-containing "marker" amino acids can be of value when different peptides are conjugated to the same sample of GMB-dexamine (4).

Provided that purification of a peptide-dextran conjugate is complete, non-sulfur containing amino acids may function in a similar context (i.e. as marker amino acids). In particular, amino acids not nor-ally found in the biologically relevant portion of peptides to be conjugated such as δ-aminovaleric acid (δ-AVA), ε-aminocaproic acid (ε-ACA), β-alanine (β-Ala), norleucine (Nle), norvaline (Nva) and α-aminobutyric acid (α-ABA), can be regarded as "markers" that specify the amount of a particular covalently-attached peptide. When located penultimately to a reactive Cys, cysteamine or DL-homoCys residue, these amino acids may also be thought of as "spacer" elements that provide distance between the chemically reactive (i.e. S-containing) and biologically relevant portions of a peptide destined for incorporation into a peptide-dextran conjugate.

It is advantageous to purify C-terminal Cys-containing peptides completely by reverse phase HPLC before using this type of peptide in a conjugation reaction. The reason for the rigorous purification of these peptides prior to their use relates directly to the manner in which peptides are synthesized by solid chase techniques, i.e. from the C-terminus. All deletion peptides or failure sequences associated with a C-terminal Cys-containing peptide will also possess the reactive (i.e. —SH-containing) Cys residue. As a result, these unwanted peptides could be expected to conjugate to GMB-dexamine (4) in the same way that the completed or desired peptide would. Such a "series" of reactions would lead to a conjugate that is really a composite of all possible deletion peptides derived from the full-length peptide of interest. In this regard, attention is directed to data shown in Tables 4 and 5.

TABLE 4

SAMPLE NAME:
CI-0060/1420K Dex (1:1) Pure Peptide

| AA  | Conc.  | Mole% | Moles  | Int. |
|-----|--------|-------|--------|------|
| ASP | 0.00   | 0.000 | 0.00   | 0    |
| GLU | 46.50  | 0.071 | 1.06*  | 1    |
| SER | 84.64  | 0.129 | 1.94   | 2    |
| GLY | 45.65  | 0.070 | 1.04*  | 1    |
| HIS | 0.00   | 0.000 | 0.00   | 0    |
| ARG | 0.00   | 0.000 | 0.00   | 0    |
| THR | 0.00   | 0.000 | 0.00   | 0    |
| ALA | 140.33 | 0.214 | 3.21   | 3    |
| PRO | 172.25 | 0.263 | 3.94   | 4    |
| TYR | 0.00   | 0.000 | 0.00   | 0    |
| VAL | 0.00   | 0.000 | 0.00   | 0    |
| MET | 0.00   | 0.000 | 0.00   | 0    |
| ILE | 0.00   | 0.000 | 0.00   | 0    |
| LEU | 0.00   | 0.000 | 0.00   | 0    |
| PHE | 0.00   | 0.000 | 0.00   | 0    |
| LYS | 165.89 | 0.253 | 3.80   | 4    |

CI-0060 = Lupus 2': Pro-Glu-Pro-Ala-Lys-Ser-Ala-Pro-Ala-Pro-Lys-Lys-Gly-Ser-Lys-Cys-CONH$_2$ 378 molecules peptide/molecule Dexamine (Max:~1024)
-ABA Recovery: 68%
* = Glu/Gly = 1.02

TABLE 5

SAMPLE NAME:
CI-0060/1420K Dex (1:1) Impure Peptide

| AA  | Conc.  | Mole% | Moles  | Int. |
|-----|--------|-------|--------|------|
| ASP | 0.00   | 0.000 | 0.00   | 0    |
| GLU | 30.39  | 0.062 | 0.93*  | 1    |
| SER | 64.77  | 0.133 | 1.99   | 2    |
| GLY | 41.84  | 0.086 | 1.29*  | 1    |
| HIS | 0.00   | 0.000 | 0.00   | 0    |
| ARG | 0.00   | 0.000 | 0.00   | 0    |
| THR | 0.00   | 0.000 | 0.00   | 0    |
| ALA | 98.69  | 0.202 | 3.03   | 3    |
| PRO | 118.85 | 0.243 | 3.65   | 4    |
| TYR | 0.00   | 0.000 | 0.00   | 0    |
| VAL | 0.00   | 0.000 | 0.00   | 0    |
| MET | 0.00   | 0.000 | 0.00   | 0    |
| ILE | 0.00   | 0.000 | 0.00   | 0    |
| LEU | 0.00   | 0.000 | 0.00   | 0    |
| PHE | 0.00   | 0.000 | 0.00   | 0    |
| LYS | 133.82 | 0.274 | 4.11   | 4    |

CI-0060 = Lupus 2': Pro-Glu-Pro-Ala-Lys-Ser-Ala-Pro-Ala-Pro-Lys-Lys-Gly-Ser-Lys-Cys-CONH$_2$ 247 molecules peptide/molecule Dexamine (Max:~1024)
-ABA Recovery: 74%
* = Glu/Gly = 0.72

The pmole ratio of an amino acid near the N-terminus (Glu) to an amino acid near the C-terminus (Gly) should be equal to one for the lupus peptide (CI-0060)/1420K dextran conjugate prepared for this experiment. The fact that this ratio is significantly less than one in the case where the impure C-terminal Cys-containing peptide was conjugated (Table 5) is consistent with a mixture of peptides actually participating in the conjugation process.

Conversely, even though an N-terminal Cys-containing peptide is also contaminated with deletion peptides after it is cleaved from the resin, none of these peptides should possess the reactive Cys residue. That is, only the peptide of interest (which is the finished peptide) should be able to undergo a conjugation reaction. That this is indeed the case is demonstrated by the data in Tables 6 and 7. Again, the pmole ratio of an amino acid near the N-terminus (epsilon-aminocaproic acid=ε-ACA) to an amino acid near the C-terminus (Pro) should be approximately equal to one for the peptide (CI-0134)/65K dextran conjugate prepared for this experiment.

TABLE 6

SAMPLE NAME:
CI-0134/65K Dex (1:1) Pure Peptide

| AA | Conc. | Mole% | Moles | Int. |
|---|---|---|---|---|
| ASP | 27.58 | 0.091 | 2.09 | 2 |
| GLU | 26.72 | 0.088 | 2.03 | 2 |
| SER | 12.15 | 0.040 | 0.92 | 1 |
| GLY | 79.88 | 0.263 | 6.06 | 6 |
| HIS | 0.00 | 0.000 | 0.00 | 0 |
| ARG | 27.00 | 0.089 | 2.05 | 2 |
| THR | 0.00 | 0.000 | 0.00 | 0 |
| ALA | 27.12 | 0.089 | 2.06 | 2 |
| PRO | 13.83 | 0.046 | 1.05* | 1 |
| TYR | 11.40 | 0.038 | 0.86 | 1 |
| VAL | 38.42 | 0.127 | 2.91 | 3 |
| MET | 0.00 | 0.000 | 0.00 | 0 |
| ILE | 0.00 | 0.000 | 0.00 | 0 |
| LEU | 13.71 | 0.045 | 1.04 | 1 |
| PHE | 13.97 | 0.046 | 1.06 | 1 |
| LYS | 0.00 | 0.000 | 0.00 | 0 |
| ACA | 11.43 | 0.038 | 0.87* | 1 |

CI-0134 = Ac-Cys-(ε-ACA)-Ala-Asp-Ser-Gly-Glu-Gly-Asp-Phe-Leu-Ala-Glu-Gly-Gly-Gly-Val-Arg-Gly-Pro-Arg-Val-Val-Val-(d)Tyr-CO$_2$H 9 molecules peptide/molecule Dexamine (Max:~54)
*ε-ACA/Pro = 0.83

TABLE 7

SAMPLE NAME:
CT-0134/65K Dex (1:1) Impure Peptide

| AA | Conc. | Mole% | Moles | Int. |
|---|---|---|---|---|
| ASP | 23.28 | 0.093 | 2.14 | 2 |
| GLU | 22.42 | 0.089 | 2.06 | 2 |
| SER | 11.00 | 0.044 | 1.01 | 1 |
| GLY | 66.75 | 0.266 | 6.13 | 6 |
| HIS | 0.00 | 0.000 | 0.00 | 0 |
| ARG | 22.00 | 0.088 | 2.02 | 2 |
| THR | 0.00 | 0.000 | 0.00 | 0 |
| ALA | 22.57 | 0.090 | 2.07 | 2 |
| PRO | 10.85 | 0.043 | 1.00* | 1 |
| TYR | 8.13 | 0.032 | 0.75 | 1 |
| VAL | 31.13 | 0.124 | 2.86 | 3 |
| MET | 0.00 | 0.000 | 0.00 | 0 |
| ILE | 0.00 | 0.000 | 0.00 | 0 |
| LEU | 11.44 | 0.046 | 1.05 | 1 |
| PHE | 11.58 | 0.046 | 1.06 | 1 |
| LYS | 0.00 | 0.000 | 0.00 | 0 |
| ACA | 9.36 | 0.037 | 0.86* | 1 |

CI-0134 = Ac-Cys-(ε-ACA)-Ala-Asp-Ser-Gly-Glu-Gly-Asp-Phe-Leu-Ala-Glu-Gly-Gly-Gly-Val-Arg-Gly-Pro-Arg-Val-Val-Val-(d)Tyr-CO$_2$H 8 molecules peptide/molecule Dexamine (Max ~54)
*ε-ACA/Pro = 0.86

The fact that the ratio is essentially the same when either a pure or an impure N-terminal Cys-containing peptide is used to generate the conjugate suggests that the impure peptide undergoes a "purification of sorts" as a result of its participation in the conjugation process. In order to obtain the highest possible purity of conjugate, all peptides are purified to analytical purity prior to conjugation.

All reagents used in the studies described herein were obtained from standard commercial sources.

Purified peptide-dextran conjugates were routinely dissolved in HPLC-grade water at a concentration of ca. 1 mg/mL. An appropriate aliquot was removed, dried in vacuo and then subjected to the Waters PICO-TAG chemistry (see above) for amino acid analysis.

Proton ($^1$H) nuclear magnetic resonance (NMR) spectra were recorded on a Varian Associates Gemini-300 300 MHz spectrometer in deuterated dimethylsulfoxide (DMSO). Chemical shift values are relative to added tetramethylsilane (TMS) as the internal standard. All peaks are expressed as ppm downfield from TMS.

Thin layer chromatography (TLC) was performed on Merck (#5715) Silica gel plates. Products were visualized by Cl$_2$/starch-KI stain and/or ninhydrin reactivity.

N$^α$-Acetyl-S-3-(3R,3S-succinimido)-L-Cys was prepared as follows: To a stirred solution of N-Ac-L-Cys (0.082 g, 0.50 mmole) in 10 mL of H$_2$O was added NMM (0.101 g, 1 mmole) and maleimide (0.0485 g, 0.50 mmole). The reaction mixture was stirred overnight at room temperature and then transferred in toto to a 25 mm×22 cm Dowex AG50W-X$_4$ column. The column was eluted with H$_2$O and fractions (25×8 mL) were collected and analyzed by TLC. The desired Cys derivative was found in fractions 8–14. These fractions were combined and lyophilized to give a fluffy, white solid. Yield: 0.074 g (0.285 mmole, 57%) mp 76–81° C. TLC (n-butanol: acetic acid: H$_2$O (4:1:1)): R$_1$=0.43. NMR: δ1.86 (s, 3H), δ2.43 (m, 1H), δ2.90 (dd, 1H), δ3.00–3.30 (m, 2H), δ3.95 (m, 1H), δ4.23 (m, 1H), δ8.31 (d, J=7.8 Hz)+δ8.34 J=7.3 Hz)=1H, δ 11.39 (s, 1H).

Hydrolysis of N$^α$-acetyl-S-3-(3R,3S-succinimido)-L-Cys with (vapor phase) 6 M HCl in preparation for PICO-TAG analysis gave the amino acid standard: S-2-(2R,2 S-succinyl)-L-Cys in quantitative yield.

A dialytic or ultrafiltrative purification has proven very satisfactory in the initial stages of the preparation of peptide-dextran conjugates. Certain applications may, however, require conjugate preparations that are completely devoid of high or low molecular weight impurities. Molecular exclusion chromatography of dextran samples on Superose 12 or Superose 6 can be very effective as a means of sample purification. A commercially available analytical Superose 12 column (Pharmacia) attached to an in house fast protein liquid chromatography (FPLC) system will separate fluoresceinated dextran (Fl-Dex) samples reasonably well. A preparative Superose 12 column (separation range: 1,000–3×10$^5$ g/mole) could be used to purify large-scale reaction mixtures of peptide-dextran conjugates. Separation results obtained from the preparative Superose 12 column using Fl-Dex standards suggest that this type of chromatography may be useful both as a means of conjugate purification and (expensive) peptide recovery.

Using these techniques, the conjugates used in the anti-histone, anti-OVA and anti-EALA studies described herein were characterized as follows:

Histone Peptide Conjugates:
1) 65K Dextran 0.2:1 molar reaction→8 mole peptide/mole dex.
(=CI-0125)
(=CI-0084/Dex$_{65K}$ (0.2:1)).

2) 65K Dextran 2:1 molar reaction→35 mole peptide/ mole dex.
   (=CI-0126)
   (=CI-0084/Dex$_{65K}$ (2:1)).
CI-0034=
N-Ac-Glu-Pro-Ala-Lys-Ser-Ala-Pro-Ala-Pro-Lys-Lys-Gly-Glu-Glu-Cys-CONH$_2$ SEQ ID NO:17

Ova Peptide Conjugates:

Analysis of the purified suppressive conjugates gave the following results:

1) 40K Dextran 0.3:1 molar reaction→2 mole peptide/ mole dex.
   (=CI-0252)
   (=CI-0159/Dex$_{40K}$ (0.3:1)).
2) 40K Dextran 1:1 molar reaction→10 mole peptide/ mole dex.
   (=CI-0253)
   (=CI-0159/Dex$_{40K}$ (1:1)).
CI-0159=
N-Ac-Cys-(ε-ACA)-Glu-Ala-His$^{331}$-Ala-Glu-Ile-Asn-Glu-Ala-Gly-Arg$_{339}$-CONH$_2$ SEQ ID NO:18.

EALA Peptide Conjugates 1) 84K Dextran 1:1 molar reaction→57 mole peptide/ mole dex.
   (=CI-0218)
   (=CI-0010/Dex$_{84}$K (1:1)).
CC-0010=Cys-Gly-Ala-Gly-(Glu-Ala-Leu-Ala)$_6$-Gly-Ala-Gly-Arg-Gly-Asp-Ser-Pro-Ala-CONH$_2$ SEQ ID NO:19.

Figure 14:
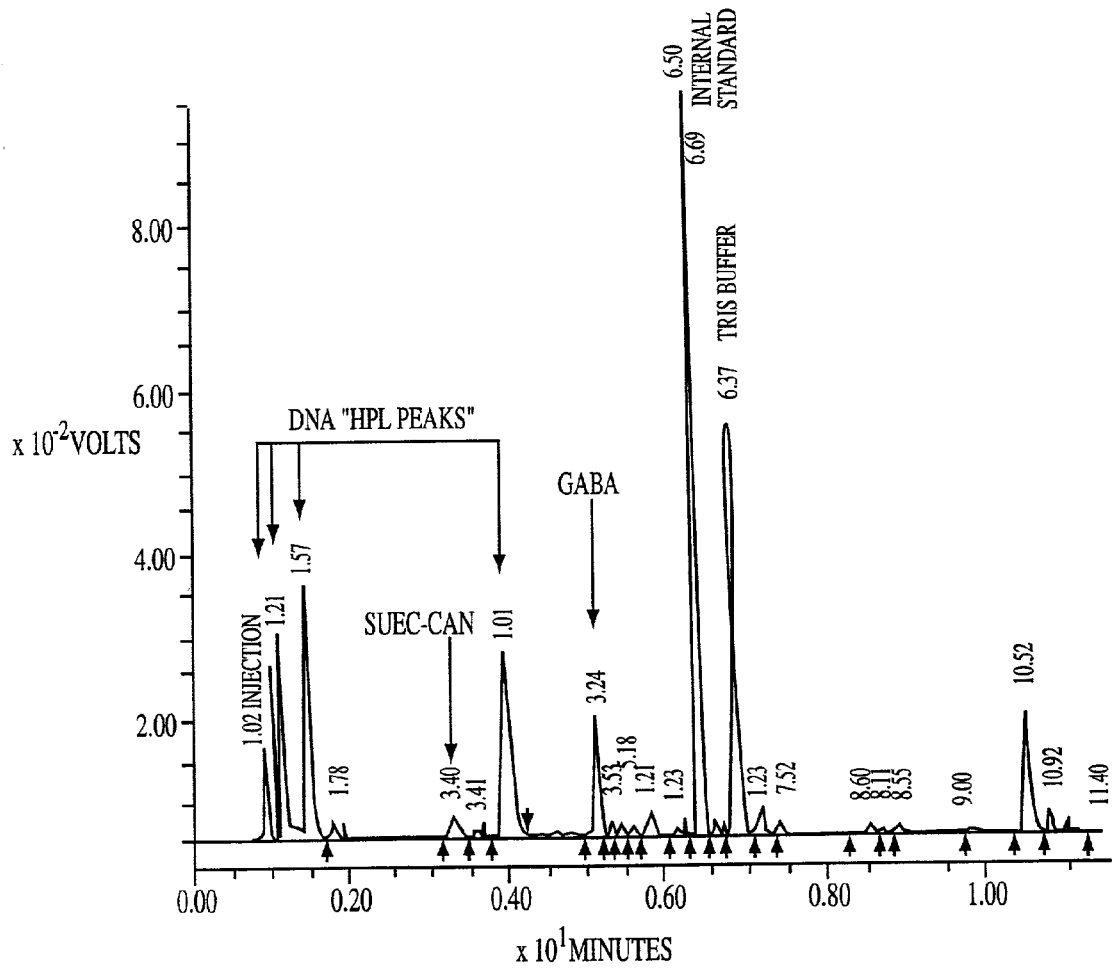
FIG. 14. Size-fractionated $DNA/Dex_{70K}$ conjugate hydrolysis peaks produced as a result of acid (HCL) hydrolysis and subsequent derivatization with phenyl-isothiocyanate (PITC).
Figure 15:
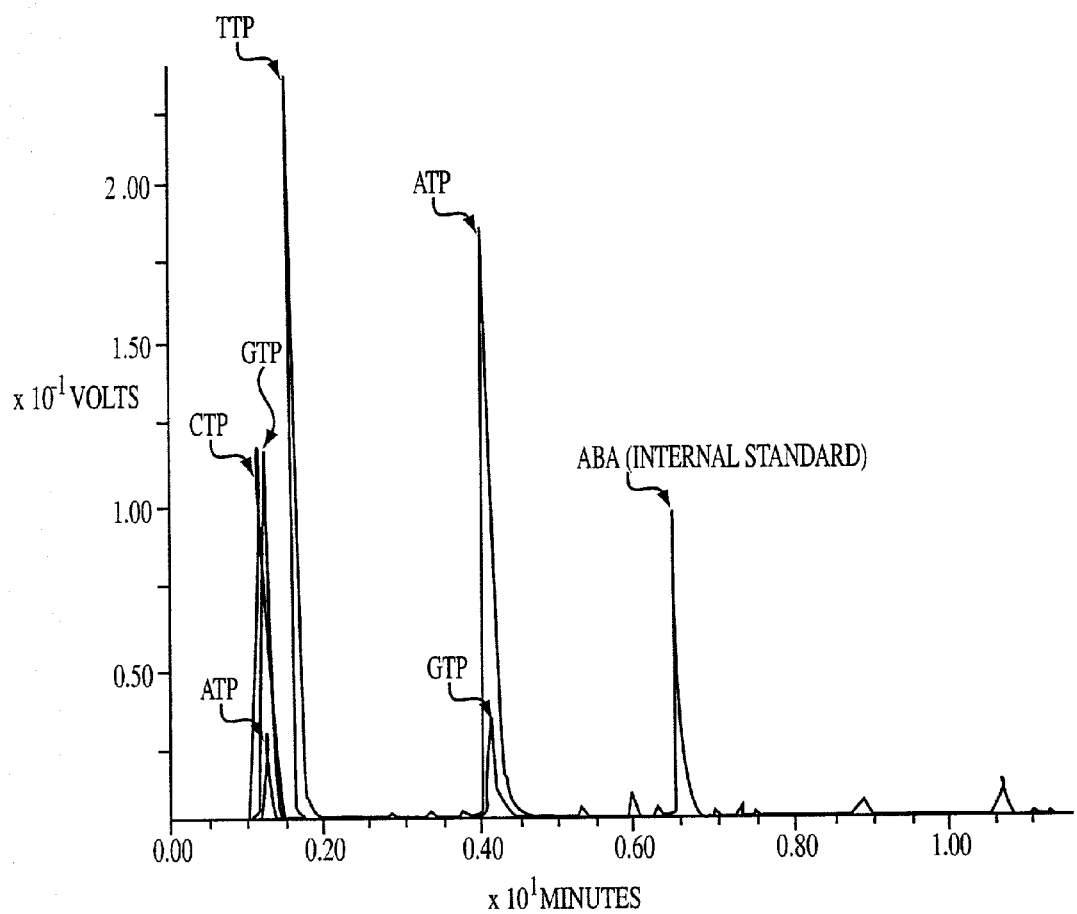
FIG. 15. DNA hydrolysis peaks produced as a result of acid hydrolysis and subsequent derivatization with phenyl-isothiocyanate (PITC).

Characterization of DNA-dextran conjugates by amino acid analysis involves the same type of manipulations as those that accompany the analysis of peptide-dextran conjugates. As a result of acid hydrolysis (6 M HCl, 110° C., 22–24 hours), the conjugate is degraded to yield: DNA nucleotide hydrolysis peaks, succinyl-Cys (Succ-Cys) on succinyl-cysteamine (Succ-Cmn), and aminobutyric acid (GABA, see FIG. 14). (The carbohydrate derived from dextran is not recovered in a quantitatable form). As is true of peptide-dextran conjugates, the importance of the liberated S-containing amino acid (Succ-Cys or Succ-Cmn) cannot be overemphasized because it ultimately provides unambiguous assessment of the level of covalent attachment of the DNA to the dextran polymer. This measure of conjugation combined with that provided by quantitation of the DNA nucleotide hydrolysis products (see FIG. 15) and direct absorbance measurement at 260 nm will result in three independently generated assessments of the amount of conjugated DNA. Taken together with the recovered GABA value, which is used to quantitate dextran recovery, conjugate DNA substitution density can be established.

Example 6

Linear polyacrylamide substituted with Dnp hapten groups was prepared as described above. Thus, linear polyacrylamide (Gelamide 250-American Cyanamid) with average molecular weight 5×10$^6$ was substituted with ethylene diamine in a manner analogous to that previously used for polyacrylamide beads (Inman et al, Biochemistry 8, 4074–4082 (1969)). Dnp derivatives were obtained by shaking the ethylene diamine substituted derivatives with excess fluorodinitrobenzene followed by extensive dialysis. The degree of substitution was determined from measurement of dry weight and optical absorbance at 360 nm. Preparations were labeled with $^{125}$I substitution levels of approximately one per 2500 monomer units were obtained, corresponding to less than one $^{125}$I per molecule labeled.

Dnp-substituted polymers were fractionated by gel filtration through 1 m long columns of Bio-Gel A-0.5 M agarose beads. These original fractions were further fractionated three more times to obtain relatively homogeneous preparations, as determined by sedimentation equilibrium measurement in the analytical ultracentrifuge.

Two Dnp-substituted polymer preparations were obtained having the following characteristics:

|  | Polymer B | Polymer D |
|---|---|---|
| Molecular weight, × 10$^{-5}$ | 0.8 | 1.8 |
| Acrylamide monomer subunits/molecule | 1050 | 2350 |
| Extended length of polymer chain, A | 2600 | 6000 |
| Acrylamide monomer subunits/Dnp | 42 | 36 |
| Average distance between Dnp groups, A | 105 | 90 |
| Total Dnp groups/molecule | 25 | 66 |
| "Effective" Dnp groups/molecule | 8–12 | 22–33 |

Polymer B was not immunogenic while Polymer D was (see Table 1, 1976 paper noted above).

Polymers B and D were subjected to further column fractionation on Sepharose Cl-4B. Two preparations (N and S) were separated for further testing. Preparation N was a central subfraction of polymer B and preparation S was a central subfraction of polymer D. Measurement of partial specific volume (0.690 ml/g) and extrapolation of sedimentation equilibrium molecular weight to zero concentration gave values of 60,000 for N and 130,000 for S. These values together with dry weight and absorbance at 360 nm show N to contain 19 Dnp groups per molecule [7–9 "effective" or appropriately spaced] whereas S contains 43 Dnp groups per molecule (14–21 "effective"). Polymers N and B had almost identical "epitope densities" or degrees of substitution by hapten per molecular size unit.

Antibody Response Polymer preparations were injected intraperitoneally in BALB/c mice in 0.5 ml of isotonic saline. After 6 days, blood was collected by bleeding from the tail, and the serum was stored at −30° C. until analysis. The concentration in serum of IgM antibody against Dnp was determined by a solid-phase binding assay. Surfaces covalently coated with Dnp-substituted gelatin served to bind the anti-Dnp mouse antibody, whose presence was then measured by a second incubation with I$^{125}$-labeled rabbit antibody against mouse IgM antibody.

In Vitro Culture and Assay. Mice were killed by cervical dislocation, and their spleens were minced in RPMI-1640 medium and pressed through a stainless steel mesh (60×60 mesh; 0.019-cm diameter). Cellular debris was allowed to settle, and the supernatant containing a dispersed-cell suspension was decanted, freed of erythrocytes by osmotic shock, and washed. Suspensions of nucleated spleen cells were then incubated with or without appropriate polymer in 60×15 mm tissue culture dishes containing 5×10$^7$ viable cells in a final volume of 7.5 ml. The incubation was carried out in 5% CO$_2$/95% water-saturated air at 37.0° C. The incubation medium consisted of RPMI 1640 medium enriched with 5% (vol/vol) heat-inactivated fetal calf serum, 2% (vol/vol) heat-inactivated horse serum, 4 mM glutamine, 100 units of penicillin and 100 µg of streptomycin per ml, and 50 µM 2-mercaptoethanol.

After 3 days of incubation, cells were harvested and washed. Assay for direct (IgM) anti-Dnp plaque-forming cells was performed.

Figure 16:
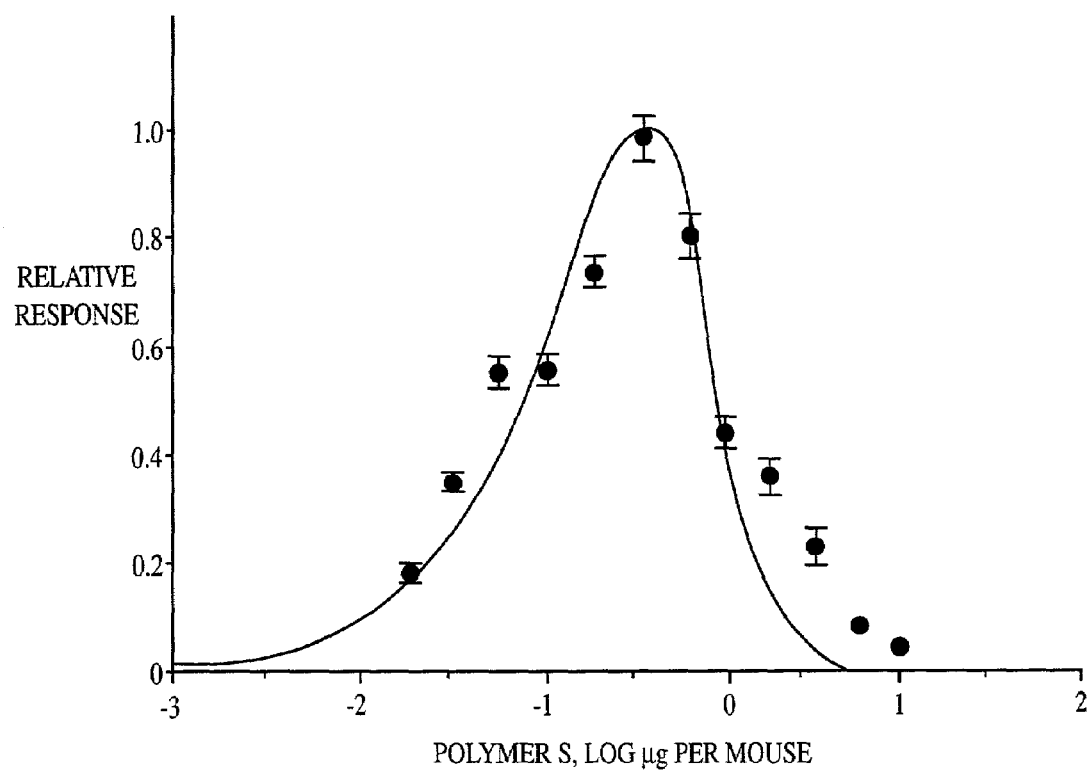
FIG. 16. Dose-response measurements showing the mean of the relative concentration, in serum from individual mice, of IgM antibody against Dnp at 6 days after injection of a stimulatory polymer (polymer S) in amounts shown (10 BALB/c mice per point). Error bars indicate SEM when it is larger than the circle. The solid curve gives the theoretical response expected from Eq. 1 (see page 96) for a peak response occurring at a dose of 0.3 μg per mouse and an immunon size, q, of 10. The theoretical response is not sensitive to the value of q if q is greater than five. The peak of the response curve corresponds to approximately 30 μg of anti-Dnp IgM per ml of serum.

The immunological response in BALB/c mice 6 days after injection of various doses of immunogenic polymer preparation S, as measured by the concentration of serum IgM molecules reactive toward Dnp groups, is shown in FIG. 16. The mice in this experiment came in a single shipment of uniform age from the supplier and were divided into groups of 10. Members of each group were injected with the same dose, and all groups were handled as uniformly as possible. The solid curve in FIG. 16 is the theoretical response curve expected from Eq 1

$$r = \frac{D_s}{D'_s}\left[\frac{(q-1)D_s^{max} + D'_s + D'_N}{(q-1)D_s^{max} + D_s + D_N}\right]^q \quad [1]$$

as visually fitted to the experimentally determined points by adjustment of the numerical value of $D_S^{max}$ to 0.3 µg. It has been shown by Dintzis et al (see Proc. Natl. Acad. Sci. USA 79:395 (1982)) that if doses $D_S$ of immunogen and $D_N$ of nonimmunogen are injected into one animal and doses $D'_S$ and $D'_N$ are injected into a second animal, then the ratio r of immune response in the first animal relative to that in the second animal should be given by Eq. 1 where $D_S^{max}$ corresponds to the dose of immunogen giving maximum response in an animal—i.e., the peak of the dose-response curve.

In view of the simplicity of the assumptions involved in the derivation of Eq. 1 and the known variability of response of individual mice, the agreement between theory and experiment is surprisingly good. However, when the experiment was repeated by using different groups of mice supplied by the same breeder, the variability of biological responses in whole animals became more evident.

Figure 17:
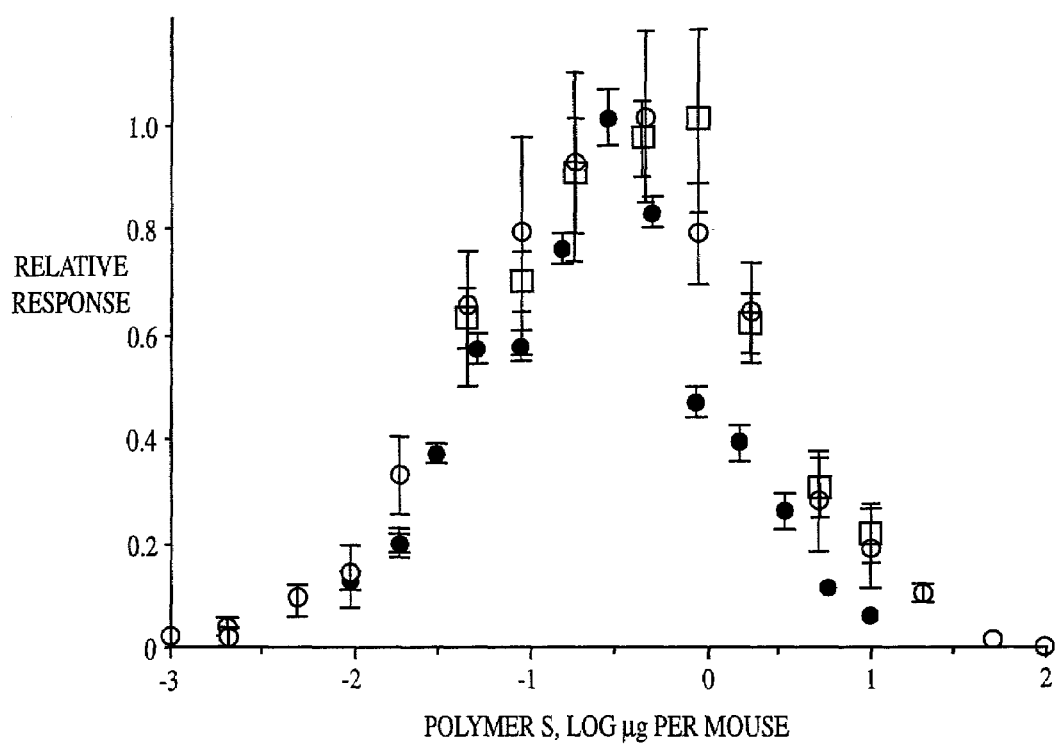
FIG. 17. Dose-response measurements for different lots of BALB/c mice. Measurements were made on serum from Individual mice. The mean of measurements on each croup at each dose is shown, together with the SEM when it is larger than the symbol. Of the symbols used, the solid black dot represents ten mice per point (these points being the same as in FIG. 16); the open circle "○" represents five mice per point; and the symbol ■ represents six mice per point.

FIG. 17 compares the dose-response curves of three separate shipments of BALB/c mice and illustrates both group-dependent variability of response of individual mice at each dose and some change of shape of the dose-response curve from group to group. The variable immunological response given by different groups of mice is a well-known phenomenon, having been observed both in studies using whole animals and in those using cell cultures. It probably is dependent on factors in the previous history and handling of the animals, such as exposure to bacteria, viruses, and parasites, which might influence the "antigenic naivete" of the animals, as well as exposure to environmental shocks such as heat and cold during shipment.

By comparing the observed dose-response curves shown in FIGS. 16 and 17 with the theoretical curve shown in FIG. 16, it is clear that although the agreement between curves is good, the observed responses are quite variable from one batch of mice to another and, in general, show a wider dose-response curve than expected from the simple model that generated the curve shown in FIG. 16.

The wider experimental curve may be explained in the following way:

The theoretical curve in FIG. 16 is based on the assumption that all cells responding to the immunogen have receptor molecules with the same binding constant for Dnp groups. This assumption of complete homogeneity is unlikely to be true. If cells that bind immunogen and respond to it have protein receptors with differing binding constants for Dnp, then the predicted response should be the sum of a number of individual cellular response curves. Each curve would be like that in FIG. 16, but those with lower binding constants would be displaced to the right by an amount proportional to the ratios between their binding constants for Dnp. Inspection of FIGS. 16 and 17 from this point of view indicates that the observed width of the experimental dose-response curves may be understood as resulting from the summation of responses from individual populations of cells having receptors differing in binding constants by 1–1.5 log units—i.e., 10 to 30-fold. The dose-response measurements can be fit within experimental error by summing the theoretical responses of three or four such populations.

Figure 18:
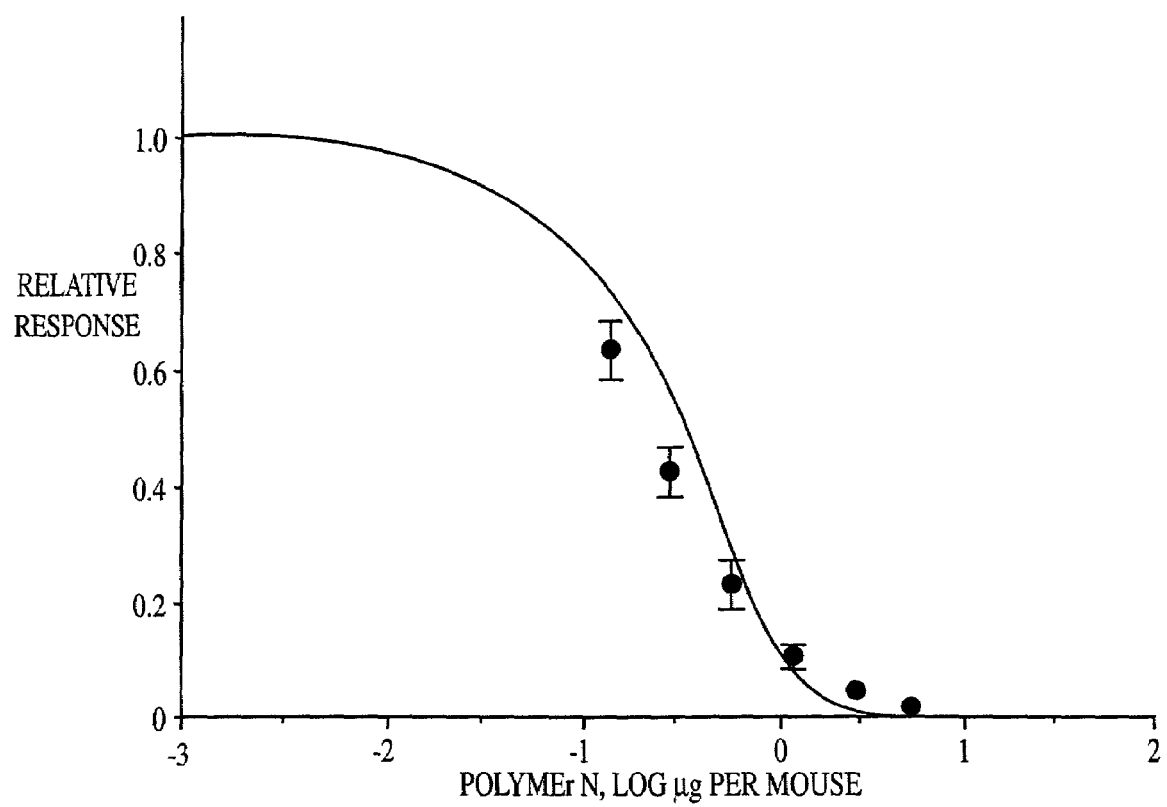
FIG. 18. Response-reduction measurements for increasing doses of nonimmunogenic polymer preparation N injected simultaneously with a constant dose of immunogenic polymer preparation S. Measurements were made on serum from individual mice. The mean of each group is shown together with the SEM when it is larger than the symbol. BALB/c mice, 10 mice per point; 0.31 μg of polymer S given to each mouse. The solid curve gives the theoretical response expected from Eq. 1 for an immunon size, q, of 10 and $D_s^{max}$ set equal to 0.5 μg per mouse as derived from FIG. 17. The theoretical response is quite insensitive to the value of q but is shifted left or right according to the value of $D_s^{max}$, with no change in shape.

For a constant dose of immunogenic polymer, Eq. 1 also can be used to predict the extent of reduction of response that will be obtained with doses of increasing amounts of nonimmunogenic polymer N. Measurements of this type are shown in FIG. 18 for BALB/c mice. The solid line in FIG. 18 is not fitted to the data but is calculated directly from Eq. 1 by using the estimated value of the maximum-response dose $D_S^{max}$ 0.5 µg per mouse obtained from FIG. 17. The agreement between the experimental points and the calculated theoretical curve in FIG. 18 is remarkable, if one considers the absence of arbitrarily adjusted parameters in this calculation.

Figure 19:
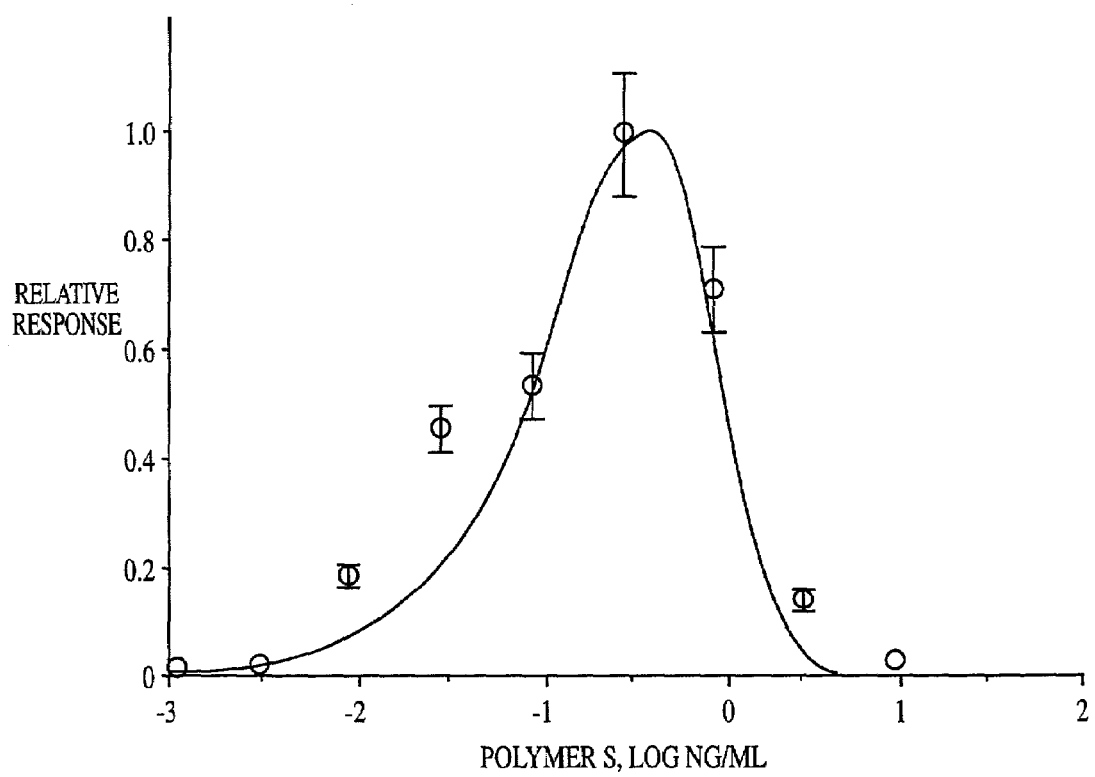
FIG. 19. Dose-response measurements regarding the relative number of direct anti-Dnp plaques produced from spleen cell cultures 3 days after the start of incubation in the presence of various concentrations of immunogenic polymer S. The data represent the mean of duplicate cultures with triplicate assays per culture; and SD is indicated when it is larger than the circle. The experimental peak response corresponds to ≈300 plaques per $10^6$ spleen cells with a blank (without polymer) of ≈20 plaques per $10^6$ spleen cells. The curve gives the theoretical response expected from Eq. 1 for a peak response occurring at a polymer concentration of 0.4 ng/ml and an immunon size, q, of 10.

In addition to experiments in living animals shown in FIGS. 16, 17, and 18, dose-response curves were measured in vitro with isolated mouse spleen cells. FIG. 19 shows the results of such an in vitro experiment as compared with a visually fitted theoretical curve calculated from Eq. 1. This agreement between experiment and theory for the in vitro experiment with cultured spleen cells (FIG. 19) is approximately as good as it was for the in vivo experiment with whole mice (FIG. 16). In both cases, the measured response curve is somewhat broader than that predicted from a model based on a homogeneous hapten binding constant in the responding cells.

Figure 20:
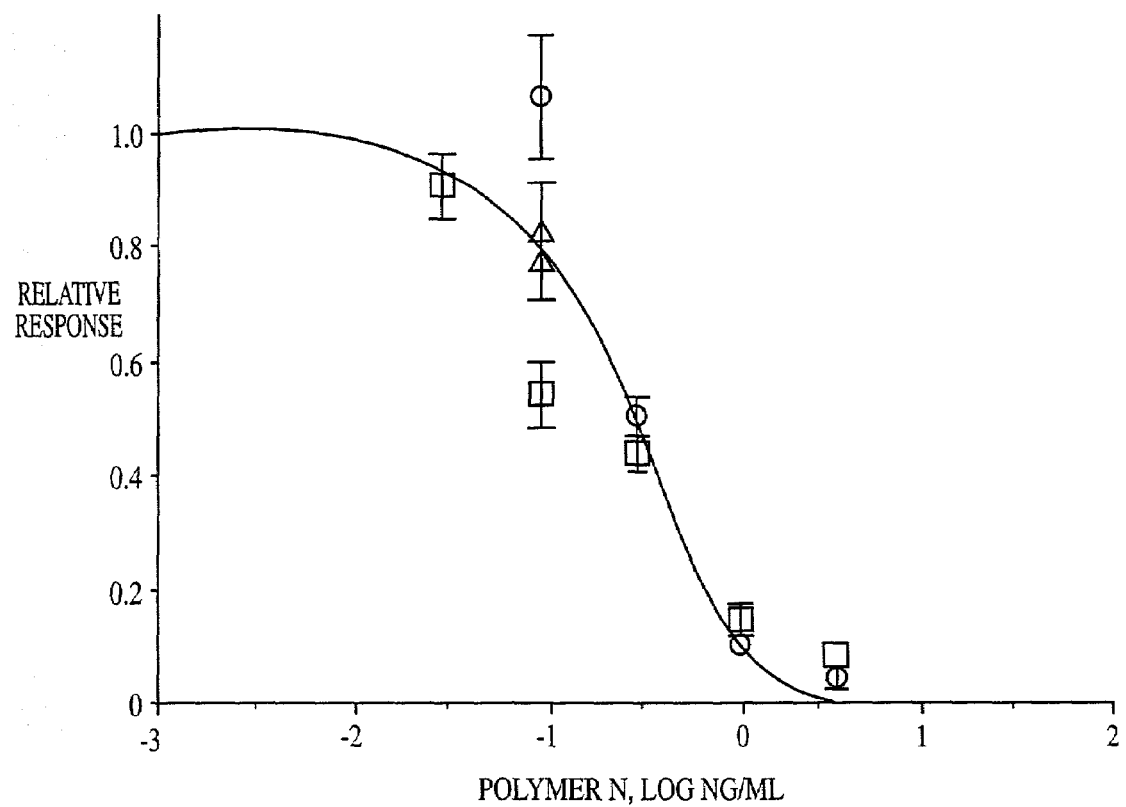
FIG. 20. Dose-reduction measurements for increasing doses of nonimmunogenic polymer preparation N incubated in spleen cell culture with a constant dose (0.3 ng/ml) of immunogenic polymer preparation S. Procedures and data treatment were as in FIG. 19. The different symbols show data obtained in separate experiments. The solid curve gives the theoretical response expected from Eq. 1 for an immunon size, q, of 10 and $D_s^{max}$ equal to 0.4 ng/ml as derived from FIG. 19.

Of particular significance to the present invention are measurements of the inhibition of immune response in vitro with increasing amounts of nonimmunogenic polymer which are shown in FIG. 20. The solid line is not fitted to the data but is calculated directly from Eq. 1 by using the value of the maximum-response dose, $D_S^{max}$, 0.4 ng/ml from FIG. 19. There is substantial agreement between the experimental points and the calculated theoretical curve.

The blood volume and extracellular fluid volume of a mouse are each ≈1 ml, so the optimal immunogenic polymer does in vivo is ≈1 µg/ml. There is a large apparent discrepancy between this in vivo dose and that which is optimally immunogenic in vitro (≈1 ng/ml). The almost 1000-fold sensitivity difference is largely explained by rapid removal in vivo of polymer molecules by phagocytes located throughout the body. Studies with $^{125}$I-labeled preparations of the polymers, as described in the above-noted 1976 paper, showed that the bulk of the injected polymer is quickly removed from the circulation by Kupffer cells in the liver and phagocytic cells in other tissues. The resulting rapid fall in free polymer concentration, coupled with uncertainties concerning the rate of equilibration of polymer between different body fluid compartments makes difficult any quantitative comparison of relative optimum concentrations in vivo and in vitro. In spite of these difficulties, there remains the fact that the shapes of the dose-response and dose suppression curves measured in vivo are remarkable similar to those measured in vitro, implying strongly that the same limiting process is being probed in both cases. Furthermore, in both cases, the measured responses as a function of dose are in excellent agreement with values obtainable from Eq. 1.

Although polymer N fails to stimulate at any dose, it inhibits polymer S at the same dose where polymer S is maximally stimulatory. This indicates a competition for surface receptors. Because both polymer preparations have almost identical "epitope densities" with a common carrier chemistry, this finding is in disagreement with theories that explain immunogenicity by invoking epitope density or polyclonal (i.e., nonspecific) activation by the "carrier."

Discussion of Example 6

The data presented above indicate the following with regard to a specific T cell-independent stimulus: (i) a specific immunogenic signal is generated by the formation of immunons on the surface of a responsive cell, (ii) an immunon will form only after a sufficient number of surface receptors are clustered, and (iii) specific clustering of surface receptors occurs as a consequence of their being bound to linked haptens. This binding is specific for the hapten-receptor interaction and does not primarily depend on the "scaffolding" to which the haptens are attached. The underlying physical scaffold that links the haptens may be molecular in nature or may consist of a surface on which small hapten-containing structures are aggregated, as on the surface of an "antigen-presenting cell."

Nonspecific stimuli, such as mitogens, lectins, antibodies against cell surface proteins, and activating or inhibiting factors from other cells, may well influence the level of "irritability" of the responding cell, making it more or less likely to respond to a given amount of immunogenic signal or even to respond in the absence of specific signals. Factors from T cells and macrophages have previously been shown to enhance antibody responses nonspecifically. Mitogens are known to stimulate cells nonspecifically to secrete antibodies. Whether or not they do this directly or indirectly by a mechanism involving specific receptor aggregation is not known. However, in contrast to these nonspecific stimuli, the data herein indicates that specific stimulation occurs by means of the linkage of receptors by their specific binding sites into immunons; thus, cells displaying those receptors are stimulated to divide and differentiate into cells that will secrete specific antibodies.

It has been demonstrated above (and in the above-referenced 1976, 1982 and 1983 papers) that molecules consisting of haptens linked to a flexible linear polymer are immunogenic only if they have a sufficient number of adequately spaced haptens. This finding with a T cell-independent antigen might at first seem contradictory to the fact that many protein molecules that are T cell-dependent antigens and which do not contain multiple identical antigenic sites are nevertheless antigenic. However, several studies have shown that the antigenicity of proteins in vivo depends on their state of aggregation. It is well-known that experimentally induced aggregation of protein molecules by physical methods (heat, adsorption to bentonite, emulsification with Freund's adjuvant) or by chemical methods (cross-linking with glutaraldehyde, or alum) greatly enhances their antigenicity. Nonaggregated protein molecules centrifuged free of aggregates or collected from the sera of injected animals have been shown to be not immunogenic but tolerogenic, whereas aggregated material with presumed multiple antigenic sites produces an immune response. Therefore, it is possible that the minimum requirements for antigenicity as determined with simple T cell-independent polymer may have applicability to immune responses to a large variety of molecules, including T cell-dependent ones. It is in any case evident that the suppressive effect of the nonimmunogenic polymer, on the immunogenic polymer, as illustrated above, can be used to control undesired immune response. The amount of nonimmunogenic polymer so used will necessarily vary depending on the specific immune response which is involved, the polymer carrier, the effective number of epitopes involved, body weight and other factors. It is believed, however, that the administration of from 0.5 to 50 mg/kg body weight would be effective in controlling undesired immune response. The administration may be effected by, for example, injection using a sterile solution of the non-immunogenic polymer.

Example 7

Extension of Immunon Model to Alternative Haptens and Carriers

As is evident from the introduction and discussions above, the invention is not dependent on the nature of the hapten or carrier but on the molecular mass of the carrier and the hapten density, these physical characteristics (molecular mass, hapten density) determining whether or not the matter is immunogenic or non-immunogenic or suppressive. This is further illustrated by the following additional disclosure and exemplification of tests done using fluoresceinated carriers. In this further work, the molecular characteristics of five chemically different fluoresceinated (Fl)-polymers were systematically varied, and their ability to stimulate an anti-hapten immune response was measured. The polymers used as carriers were carefully size-fractionated and consisted of one natural polymer (dextran), one modified natural polymer (carboxymethyl cellulose), and three synthetic polymers (Ficoll, polyvinyl alcohol, and polyacrylamide). The carriers varied in physical structure from the highly cross-linked Ficoll, to the somewhat branched dextran to the linear polyacrylamide, carboxymethyl cellulose and polyvinyl alcohol. Polymers were haptenated with Fl and size-fractionated so as to yield a panel of molecules with varying molecular mass, hapten valence and hapten density. Anti-Fl response to these haptenated polymers was measured in vivo after i.p. injection of the Fl-polymer in saline, and measured in vitro following culture with unfractionated spleen cells from naive mice.

In agreement with the foregoing exemplification involving Dnp-polyacrylamide, it was found that to be immunogenic, each of the Fl-polymers had to exceed a comparable threshold value of molecular mass and of hapten valence. Optimal immunogenicity occurred when the Fl-polymers had values of mass and hapten density lying within a predictable range. Immunogenicity decreased when these optimal parameters were substantially increased or decreased. Accordingly, it can be concluded that the immunogenicity of soluble haptenated polymers depends on predictable physical molecular characteristics, and is relatively independent of the chemical composition and conformation of the carrier polymer.

Polymer carriers selected to be haptenated were dextran (T2000, T500 and T70—Pharmacia); Ficoll (400 and 70—P*harmacia*); carboxymethyl cellulose (*medium viscosity*—S*igma*); polyvinyl alcohol (*average* molecular weight 115,000—Aldrich); and linear polyacrylamide (synthesized in aqueous solution from crystalline acrylamide).

The polymer carriers were conjugated with fluorescein by the following procedures: Reactive carboxyl groups were generated in polyacrylamide by partial hydrolysis in 0.05M $Na_2CO_3$-0.05M $NaHCO_3$, pH 10.1, at 20° C. (3). Amino groups were introduced into such deamidated polyacrylamide and also into dextran, Ficoll, polyvinyl alcohol and carboxymethyl cellulose according to the procedures disclosed by Inman, J. Immunol. 114:7044. Subsequently, the amino groups on the polymers were conjugated to excess fluorescein isothiocyanate at pH 9.2 in 0.1M $Na_2B_4O_7$. The polymers were then dialyzed exhaustively against the buffer used for subsequent gel filtration (0.1M NaCl, 0.001M EDTA, 0.02% NaN$_3$, 0.01M KPO$_4$, pH 7.4).

Fl-polymers were then repeatedly fractionated over 95 cm columns of Sepharose CL-2B, CL-4B and/or CL-6B; center cuts were taken repeatedly to give preparations of relatively narrow molecular weight distributions. Fl content was determined by measuring optical density at 496 nm in 0.01 M Na$_2$B$_4$O$_7$ using a molar extinction coefficient of 72,000 for Fl. This measurement together with polymer dry weight measurement permitted calculation of epitope density. Molecular mass was determined by sedimentation equilibrium analysis in the analytical ultracentrifuge as known in the art (Proc. Natl. Acad. Sci 73:3671 1976). Measurements were performed at several polymer concentrations by using the short column method, and molecular mass was obtained by extrapolation to zero polymer concentration. Polymers used in experiments were dialyzed against PBS and were sterilized by filtration with the use of 0.22-μm Nucleopore filters.

For in vitro studies, suspensions of 2×10$^7$ nucleated spleen cells from naive mice (CAF./J female mice, mostly 8–10 weeks old) were cultured in a final volume of 2 ml with or without appropriate polymer in 15 ml sterile polystyrene centrifuge tubes placed at an angle of 3 degrees from the horizontal. After 3 days of incubation, cells were harvested and washed. Assay for direct (IgM) anti-hapten plaque-forming cells (PFC) was performed using a modification of the procedure described in Trans. Rev. 18:130 (1974). All cultures were done in triplicate and PFC assays were performed on each culture in duplicate. Immune response was expressed as PFC per 106 spleen cells. Responses of control cultures without added antigen were subtracted from those of experimental cultures. Typically, this control measured 5+/−2 PFC per 106 cells.

Indicator cells in the plaque assay were hapten substituted at low density in order to minimize assay response to low affinity (i.e., non-specific) antibody. Substituted indicator cells were prepared by mixing 1 ml of packed burro red blood cells (BRBC) with a solution of 1 mg of fluorescein isothiocyanate dissolved in 9 ml of borate buffered saline (BBS; 0.9% NaCl containing 10 mM sodium borate, pH 9.2). The mixture was then stirred for 1 hour at room temperature in the dark. The cells were centrifugally washed first in BBS and then 3 or 4 times in PBS. They were stored in PBS containing 0.11% glycylglycine for no longer than one week. They were washed in PBS before use. Fl-substituted BRBC were found to be as effective as Fl-polymer substituted BRBC in detecting anti-Fl plaque forming spleen cells in this system. Trinitrophenyl (Tnp) substituted indicator cells were prepared as described in J. Immunol. 131:2196 (1983).

In vitro studies were conducted in parallel with whole animal measurements in order to rule out possible differences in immunogenic behavior due to differential body excretion rates or organ and tissue distribution. Conversely, confirmation of in vitro findings by in vivo results eliminated concern that in vitro findings merely reflected artifacts of cell culture. Culture of unfractionated spleen cells was the in vitro assay of choice in order to mimic as closely as possible the cellular milieu to which these molecules might be exposed in the living animal.

For in vivo antibody response, polymer preparations were injected into mice intraperitoneally in 0.5 ml isotonic saline. Adjuvants were not used in any antigen administration because they could change the physical state of the antigen in such a way as to make interpretation of actual molecular mass of the administered antigen impossible. After 4 days, mice were sacrificed and their spleens removed for PFC assay. Responses of control mice injected only with saline were subtracted from those of experimental mice. Typically, this control measured 10+/−5 PFC per 10$^6$ cells.

For the doses of Fl-polymers used to generate anti-hapten responses, no more than 1% of the observed anti-Fl response could be generated when unsubstituted carrier was used as immunogen. When tested for non-specific polyclonal antibody generation, unhaptenated carrier molecules were found to generate no plaques against unsubstituted burro red blood cells (BRBC) or against BRBC substituted with either pneumoccoccal polysaccharide type 3 or with dinitrophenyl groups (data not shown). These observations indicated that, in the doses used to generate anti-Fl responses, Fl-polymers did not significantly stimulate B cells having epitope specificity distinct from fluorescein.

The composition and characteristics of the haptenated polymers used herein are listed in Table 1 (see page 31).

All of these polymer carriers were essentially uncharged with the exception of the CMC which is negatively charged. Haptenation with fluorescein resulted in substituted polymers which were hydrophilic and negatively charged.

Figure 21:
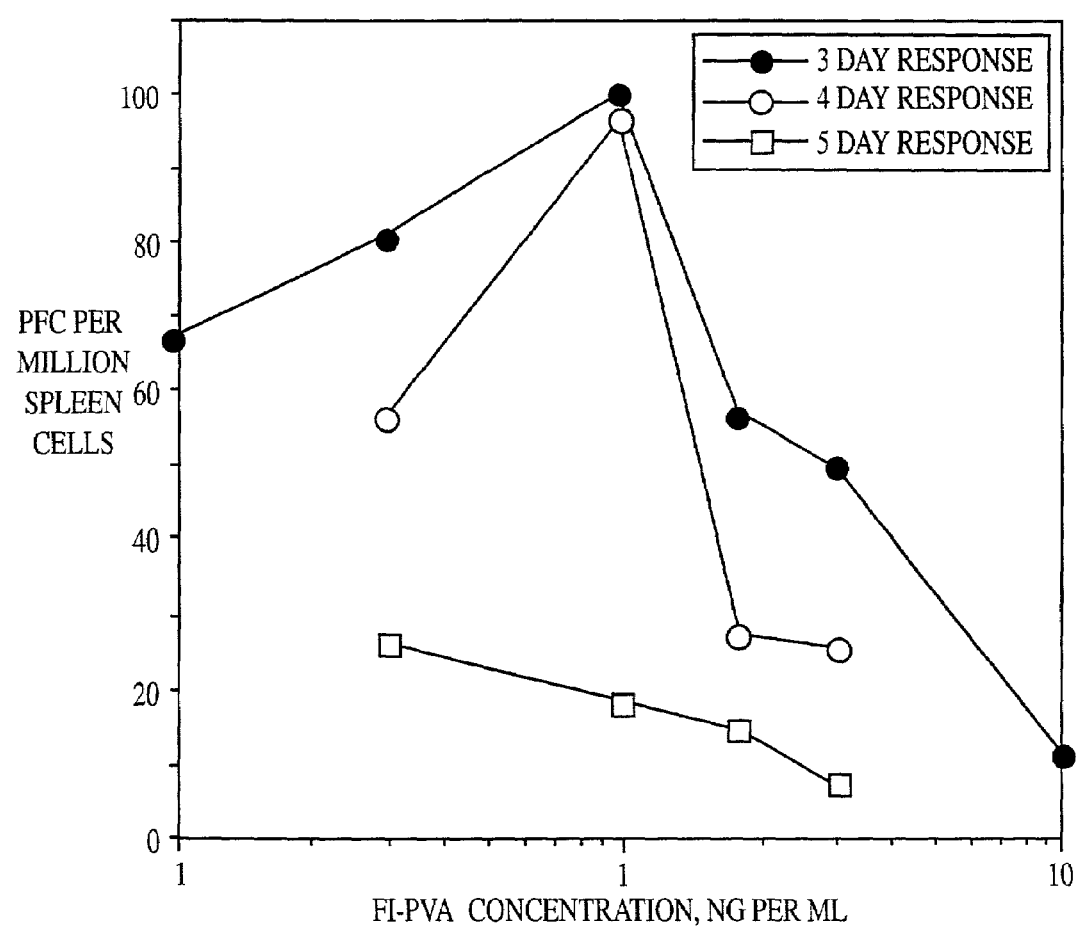
FIG. 21. In vitro response kinetics. The direct (IgM) anti-Fl response of naive spleen cells to increasing doses of $Fl_{110}PVA400$ was measured after 3,4, or 5 days of culture. All the S.D. were less than 10%.
Figure 22:
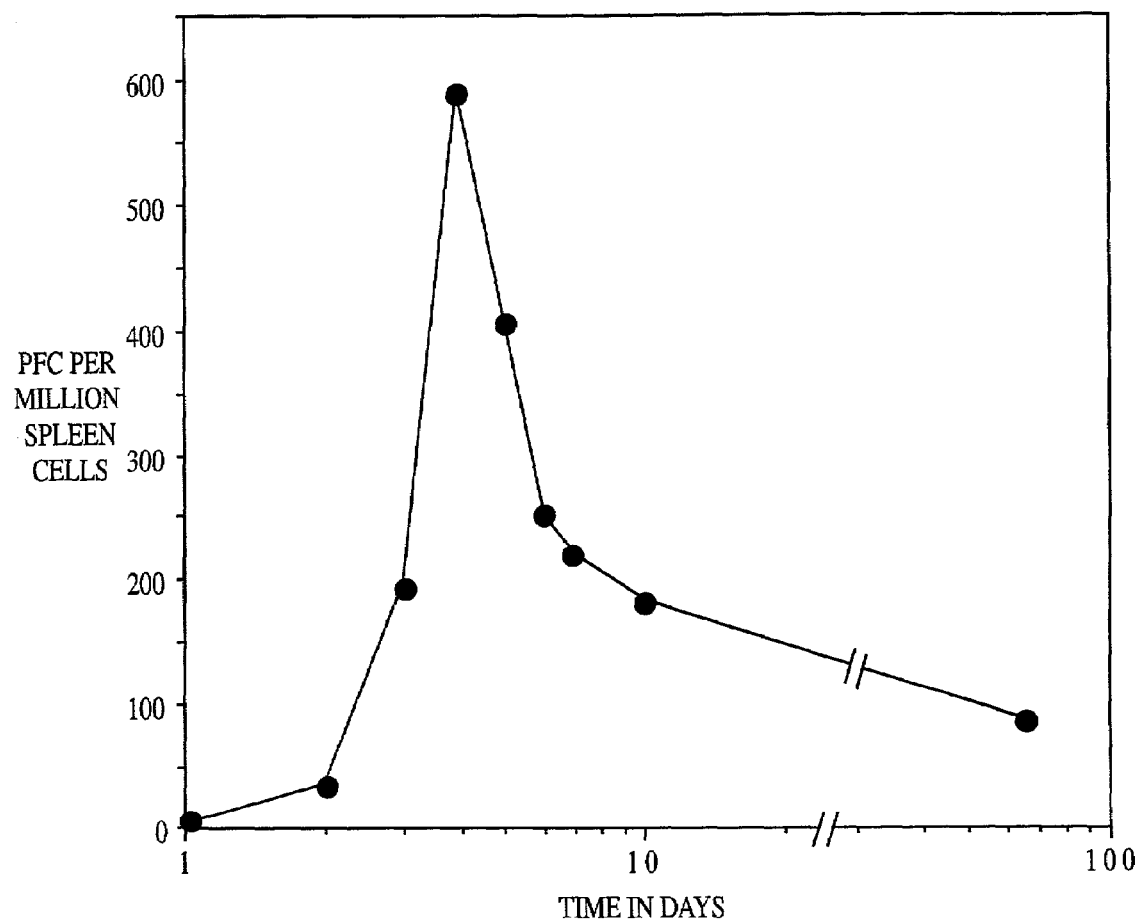
FIG. 22. in vivo response kinetics. An optimal dose of $Fl_{55}PVA200$ (10 ug/mouse) was injected i.p. in 0.5 ml saline, and direct (IgM) anti-Fl response was measured at times from 0 to 66 days. Each point represents 3 mice and is the mean of triplicate assays. The S.D. was less than 10%.

It was found that the kinetics of response to this series of Fl-polymers closely resembled those observed for Dnp-polyacrylamide. As an example, FIG. 21 shows dose-response curves of the primary in vitro anti-hapten response of naive spleen cells to Fl-PVA after various times of incubation. The peak in vitro response occurred after three days of incubation. The kinetics of the primary in vivo anti-hapten response to the optimal dose of the same polymer are pictured in FIG. 22. Spleen PFC peaked at about 4 days.

Figure 23:
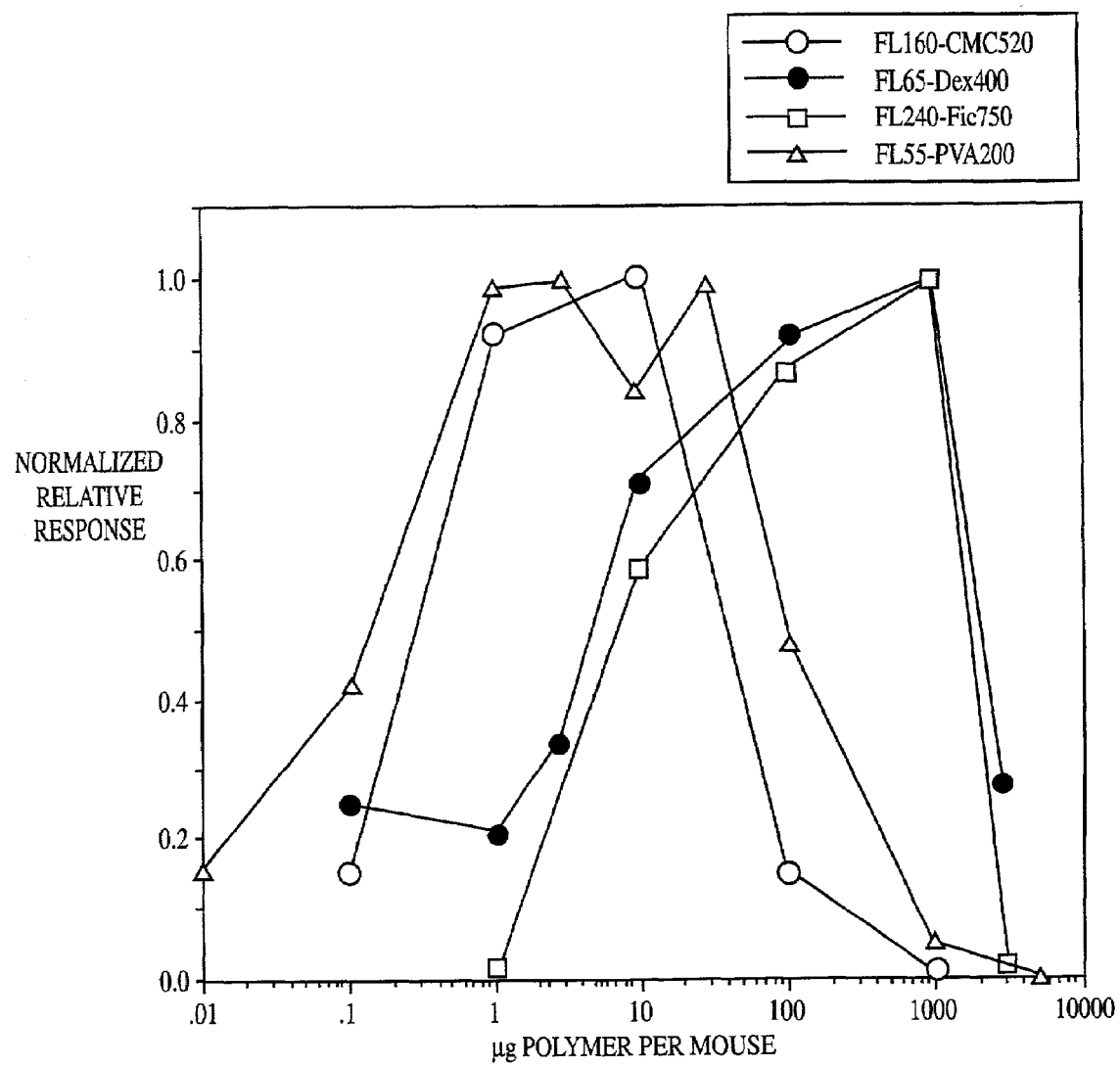
FIG. 23. In vivo normalized dose-response curves generated by four Fl-polymers with different carriers. Each point represents the mean of triplicate assays. Mice were injected with increasing doses of a Fl-polymer i.p. in saline (three mice/point), and PFC were measured after 4 days. Curves were normalized so that maximum response was assigned a value of 1, and other responses were expressed as fractions of the maximum response. The S.D. was less than 10%.
Figure 24:
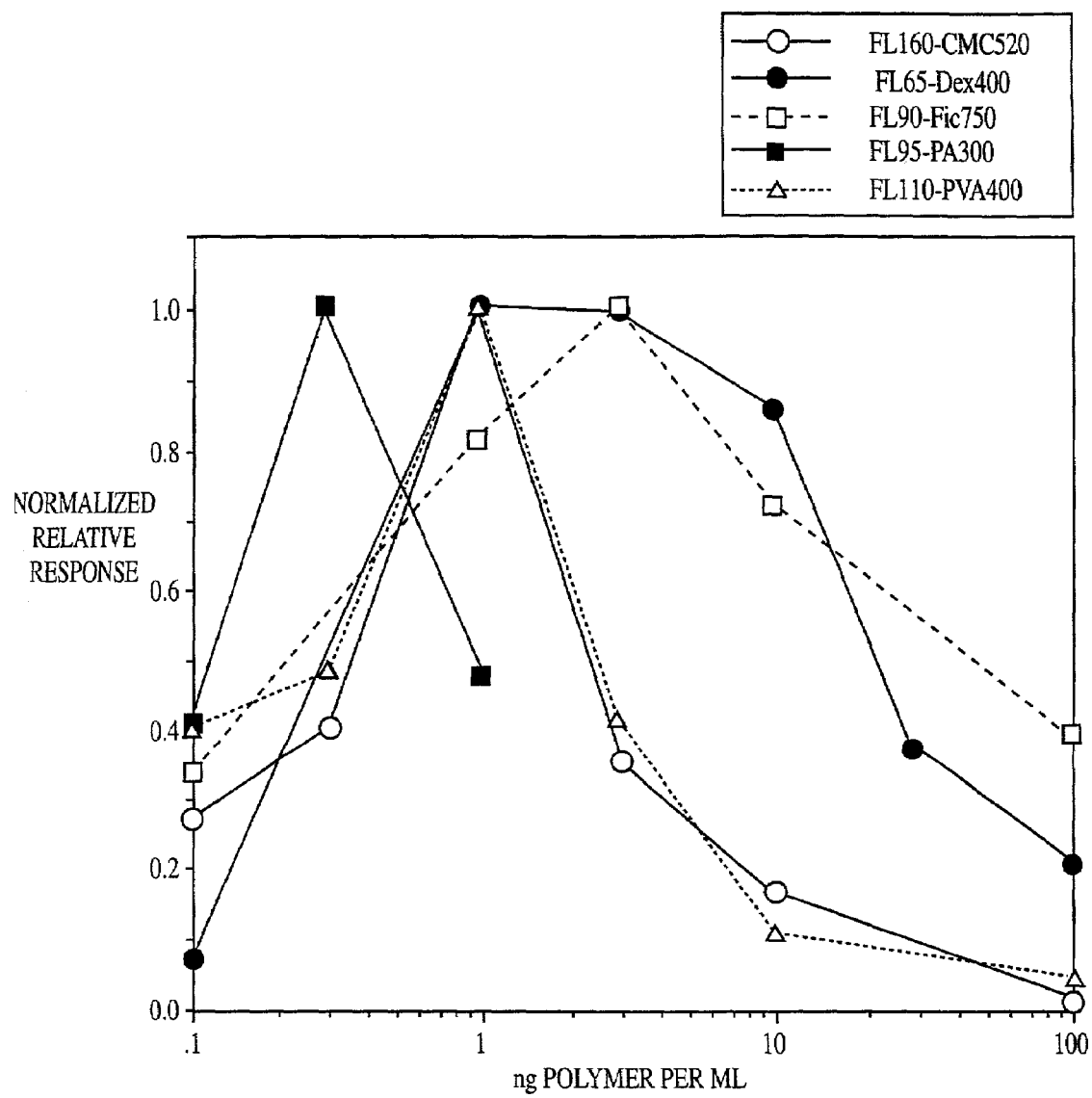
FIG. 24. In vitro normalized dose-response curves generated by five Fl-polymers with different carriers. Direct (IgM) anti-Fl PFC were measured after three days of culture of polymer with naive spleen cells. Curves were normalized so that maximum response was assigned a value of 1, and other responses were expressed as fractions of the maximum response.

In vivo anti-hapten dose-response curves generated by four different fluoresceinated polymers, Fl-Dex, Fl-Fic, Fl-CMC and Fl-PVA, are shown in FIG. 23. In vivo dose response curves, shown in FIG. 24, include the curve generated by an additional polymer Fl-PA. These curves are representative of the responses generated by all the immunogenic polymers used in this study. Each dose-response curve is bell-shaped, initially increasing with the dose of antigen until a maximum is attained and then decreasing at higher doses of antigen.

Each of the size-fractionated polymers tested was consistent in behavior in vitro and in vivo being either immunogenic or nonimmunogenic in both situations. Table 8 lists a number of representative polymers with the results of assays for their stimulation of anti-hapten antibody responses.

TABLE 8

| Polymer | Density (mM Fl/gm polymer) | Immune Response (in vitro[a] in vivo[b]) | |
|---|---|---|---|
| Fl$_{240}$Fic750 | 0.32 | + | + |
| Fl$_{90}$Fic750 | 0.12 | + | + |
| Fl$_{65}$Dex400 | 0.16 | + | + |
| Fl$_{60}$Dex170 | 0.35 | + | N.D.[c] |
| Fl$_{95}$PA300 | 0.32 | + | N.D. |
| Fl$_{230}$PA400 | 0.58 | + | N.D. |
| Fl$_{160}$CMC520 | 0.32 | + | + |
| Fl$_{26}$CMC110 | 0.24 | + | + |
| Fl$_{110}$PVA400 | 0.28 | + | N.D. |
| Fl$_{55}$PVA200 | 0.28 | + | + |
| Fl$_{14}$Fic40 | 0.35 | − | − |
| Fl$_{6}$Fic35 | 0.17 | − | − |
| Fl$_{14}$Dex40 | 0.35 | − | N.D. |
| Fl$_{47}$PA80 | 0.59 | − | N.D. |

TABLE 8-continued

| Polymer | Density (mM Fl/gm polymer) | Immune Response (in vitro[a] in vivo[b]) |
|---|---|---|
| $Fl_6CMC27$ | 0.22 | − − |
| $Fl_{14}PVA50$ | 0.28 | − − |

[a] Determined by measuring direct anti-Fl PFC after 3 day culture of naive spleen cells with antigen.
[b] Determined by measuring direct anti-Fl-PFC of spleen cells harvested 4 days after i.p. injection of antigen in saline without adjuvant.
[c] N.D. = not determined It is to be noted that the subscript number after the hapten abbreviation refers to the number of haptens per molecule (hapten valence), while the number after the carrier abbreviations refers to the molecular mass in kD. For example, $Fl_{65}Dex400$ refers to a molecule with 65 fluorescein groups on a dextran carrier, with a total molecular mass of 400,000 daltons.

Over a 4 log dose range, the group of polymers listed above the dotted line were immunogenic and the group below the dotted line were nonimmunogenic. Both groups included molecules with each of the five kinds of polymer carriers studied: Fl-Fic, Fl-Dex, Fl-PA, Fl-CMC and Fl-PVA. Thus all five Fl-polymers have the potential to be either immunogenic or -nonimmunogenic, irrespective of the chemical composition of the polymeric carrier. Examination of the molecular characteristics of the polymers in Table 8 indicates that immunogenicity is directly related to the molecular mass and the hapten valence. All polymers above the dotted line, had a hapten valence greater than 20 and a molecular mass larger than 100,000 daltons and were immunogenic. Polymers below the dotted line had a molecular mass less than 100,000 daltons and were not immunogenic at any dose tested. The hapten densities in both groups had approximately the same range: between 0.12 and 0.59 millimoles of fluorescein per gram of polymer. Thus, hapten density by itself was not a predictor of the presence or absence of immunogenicity.

Example 8

Antigen Specific Suppression Independent of Carrier Chemistry

The inhibiting properties of nonimmunogenic Fl-polymers are further illustrated by the following example.

Figure 25:
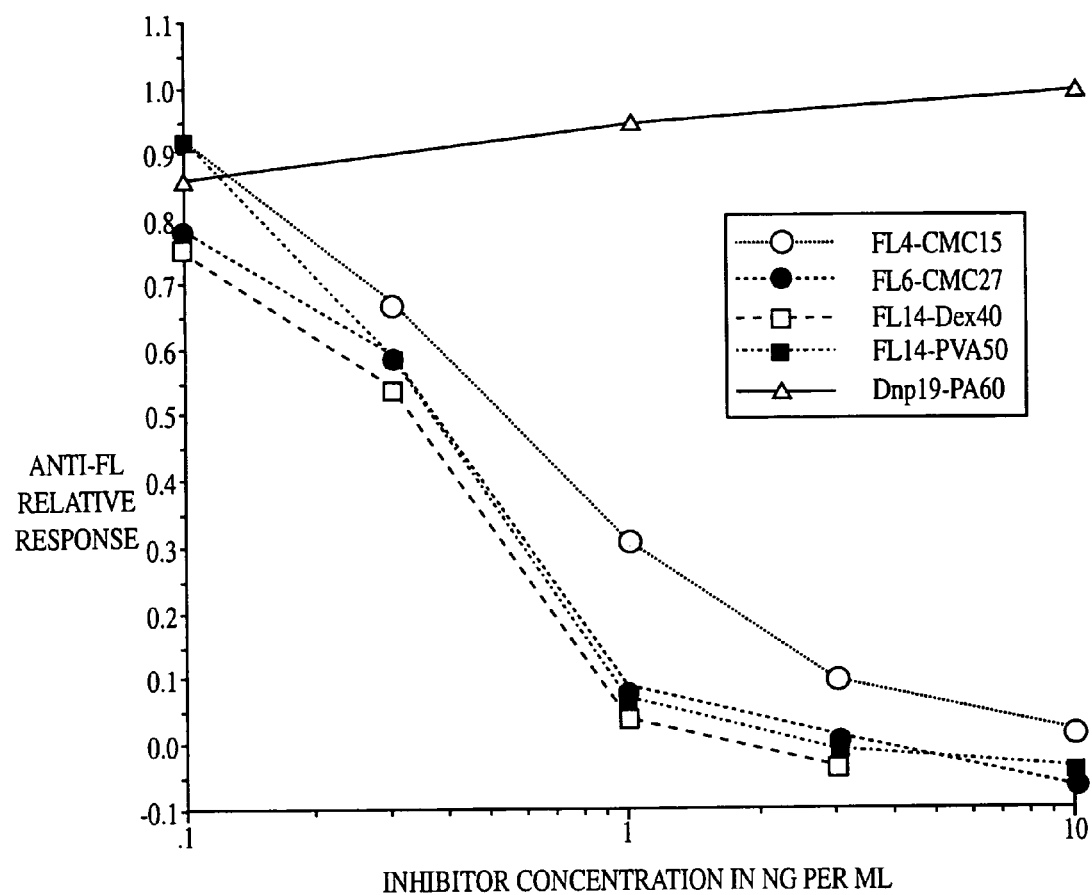
FIG. 25. Inhibition of the in vitro response to $Fl_{90}Fic750$ by non-stimulatory Fl-polymers. The IgM PFC response to $Fl_{90}Fic750$ alone was assigned a value of 1 and the response of cultures containing added amounts of nonimmunogenic polymers was expressed as the fractional relative response. The concentration of $Fl_{90}Fic750$ in each culture was kept constant at 3 ng per ml.

As shown above, soluble fluoresceinated polymers with molecular mass under 100,000 daltons and with hapten valence under 20 were unable to stimulate an anti-hapten response at any measured dose. However, this example shows that when mixed with optimal concentrations of stimulatory Fl-polymers and cultured with naive spleen cells in vitro, anti-hapten antibody production can be inhibited. FIG. 25 shows a representative example of such inhibition.

Naive spleen cells were cultured with a series of solutions formulated to contain increasing concentrations of the non-immunogenic polymers together with a constant concentration of the immunogenic polymer $Fl_{90}Fic750$. As can be seen, the inhibitory ability of the nonimmunogenic polymers increases with increasing concentration until complete inhibition of the anti-Fl response to the immunogenic polymer is reached at inhibitor concentrations between approximately 1 and 10 ng per ml.

FIG. 25 demonstrates "cross-inhibition", whereby Fl on the backbone carriers, PVA, Dex, or CMC can inhibit the anti-Fl response stimulated by Fl-Fic. The data indicate that the inhibitory potentials of these nonimmunogenic Fl-polymers are largely independent of specific carrier chemistry. As a control, FIG. 25 shows that the irrelevant hapten, Dnp, on a PA carrier could not inhibit the anti-Fl response. Carrier-independent inhibition is further evidenced in Table 9, where the ability of four nonimmunogenic Fl-polymers to inhibit the immune response to four immunogenic polymers with different carrier backbones is shown.

TABLE 9

Carrier Independent Inhibitory Ability of F1-Polymers

Figure 26:
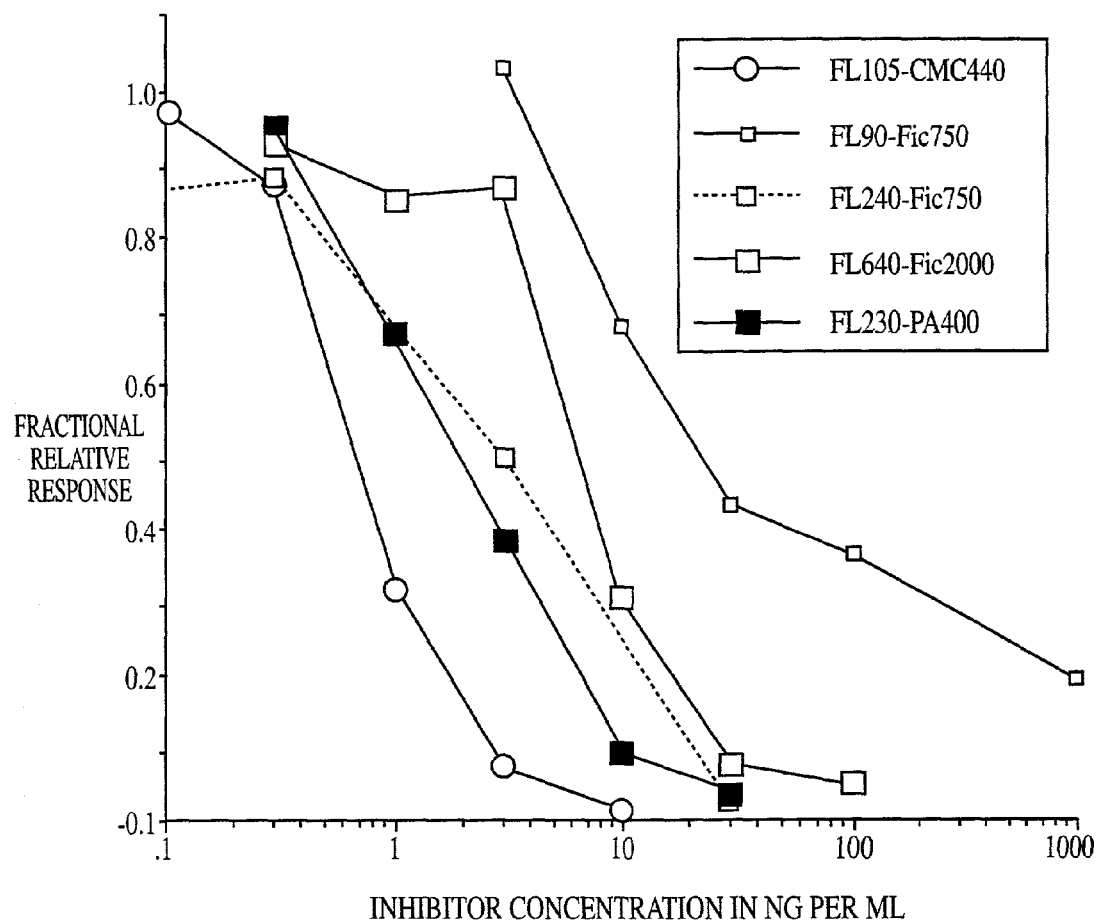
FIG. 26. Inhibition of the in vitro response to $Fl_{90}Fic750$ by high doses of immunogenic Fl-polymers. The IgM PFC response to 3 ng per ml of $Fl_{90}Fic750$ alone was assigned a value of 1, and the response of cultures containing added amounts of Fl-polymer was expressed as the fractional relative response.

| Inhibitory Polymer | Hapten Density (mM F1/gm polymer) | Concentration[a] (ng/ml) for 50% Inhibition of Response to | | | |
|---|---|---|---|---|---|
| | | $Fl_{90}Fic750$ | $Fl_{65}Dex400$ | $Fl_{110}PVA400$ | $Fl_{105}CMC440$ |
| $Fl_{14}Fic40$ | 0.35 | 0.5 | 1 | 1 | 0.3 |
| $Fl_{14}Dex40$ | 0.35 | 0.35 | 2 | N.D.[b] | N.D.[b] |
| $Fl_{14}PVA50$ | 0.28 | 0.4 | 3 | 0.5 | N.D.[b] |
| $Fl_6CMC27$ | 0.22 | 0.4 | 2 | 1 | 1 | a) Concentration giving 50% inhibition was determined by measuring the decrease of direct anti-F1 PFC caused by adding the inhibitory polymer to a culture containing a constant amount of immunogenic polymer.
b) N.D. = not determined FIG. 26 shows inhibition curves generated by five chemically different Fl-polymers when mixed in increasing amounts with a constant amount of $Fl_{90}Fic750$. One of the curves illustrates the self-inhibition caused by adding increasing amounts of $Fl_{90}Fic750$ to an optimally immunogenic concentration of the same polymer. For each of the Fl-polymers used, inhibition increases with dose. Although this may be termed "high-dose" inhibition, the actual in vitro molar concentration of inhibitor necessary for 50% inhibition of the response to $Fl_{90}Fic750$ did not exceed 30 pM for any of the Fl-polymers, and for $Fl_{105}CMC440$, it was as low as 2 pM.

The influence of hapten density and molecular mass individually on inhibitory ability was also measured. Table 10 compares the inhibitory abilities of pairs of Fl-polymers with similar molecular mass, but differing hapten densities. In each pair of molecules where the molecular mass was kept constant, the polymer with the higher hapten density was the better inhibitor, i.e., lower concentrations were required to cause a 50% inhibition of the response to $Fl_{90}Fic750$.

TABLE 10

Effect of Hapten Density on Inhibitory Ability

| Inhibitory Polymer | Hapten Density (mM FL/gm polymer) | Conc.[a] for 50% Inhib. of FL$_{90}$Fic750 Response | |
|---|---|---|---|
| | | (ng/ml) | pM |
| FL$_{240}$Fic750 | 0.32 | 5 | 7 |
| FL$_{90}$Fic750 | 0.12 | 25 | 33 |
| FL$_{230}$PA400 | 0.58 | 2 | 5 |
| FL$_{65}$Dex400 | 0.16 | 10 | 25 |

[a]Concentration giving 50% inhibition was determined by measuring the decrease of direct anti-Fl-PFC by adding the inhibitory polymer to a culture containing a constant amount (3 ng per ml) of Fl$_{90}$Fic750.

Table 11 compares the inhibitory abilities of two sets of polymers, one set with CMC as the carrier, and the other set with Ficoll as the carrier. The hapten densities in each set are similar, but the molecular weights differ. Included in the CMC carrier set are two nonimmunogenic polymers (Fl$_6$CMC27 and Fl$_4$CMC15); one nonimmunogenic polymer (Fl$_{14}$Fic40) is included in the Fic carrier set. In each set, regardless of immunogenic potential, the polymer with the higher molecular weight is the better inhibitor.

TABLE 11

Effect of Molecular Mass on Inhibitory Ability

| Inhibitory Polymer | Hapten Density (mM FL/gm polymer) | Conc. (pM)[a] for 50% Inhib. of FL$_{90}$Fic750 Response |
|---|---|---|
| FL$_{105}$CNC440 | 0.24 | 2 |
| FL$_{26}$CMC110 | 0.24 | 9 |
| FL$_6$CMC27 | 0.22 | 15 |
| FL$_4$CMC15 | 0.27 | 40 |
| FL$_{640}$Fic2000 | 0.32 | 4 |
| FL$_{240}$Fic750 | 0.32 | 6 |
| FL$_{14}$Fic40 | 0.35 | 9 |

[a]Concentration giving 50% inhibition was determined by measuring the decrease of direct anti-Fl-PFC by adding the inhibitory polymer to a culture containing a constant amount (4 pM) of Fl$_{90}$Fic750.

Example 9

A. Suppression of Ongoing T-cell Dependent Immune Response Against a Hapten

Figure 27:
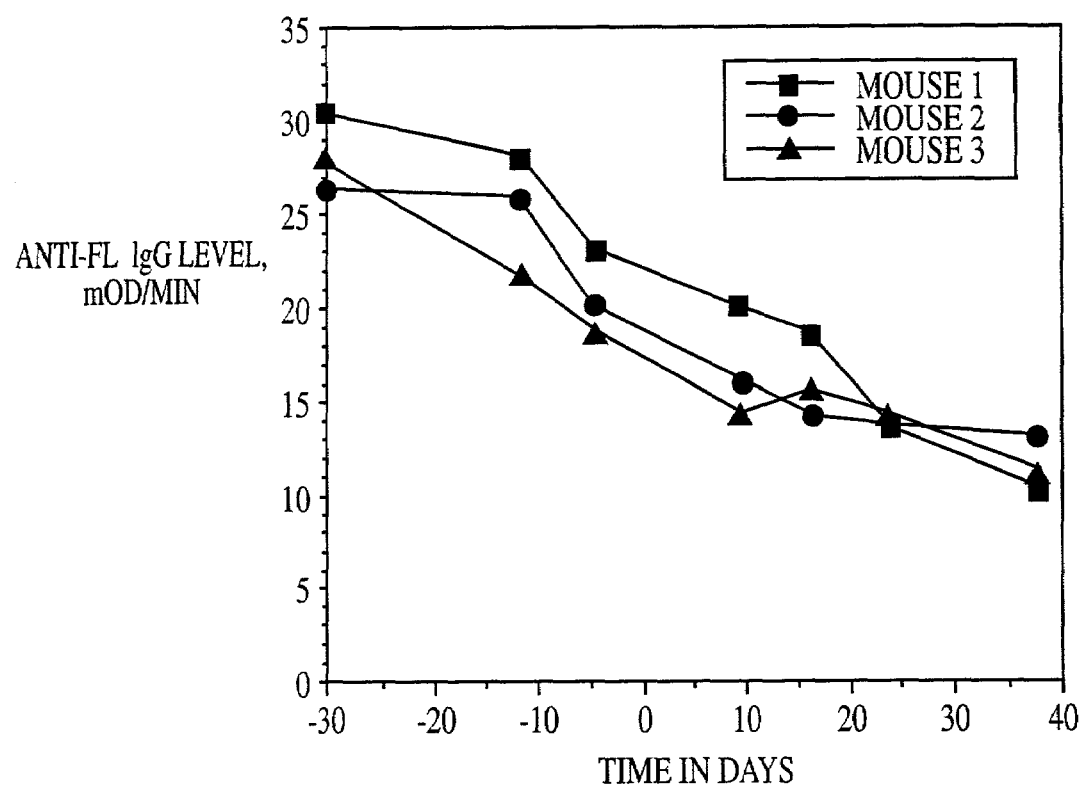
FIG. 27. Anti-fluorescein IgG antibody serum levels in immunized mice as a function of time. The mice have been repeatedly injected with fluoresceinated ovalbumin on aluminum hydroxide adjuvant and allowed to rest for several weeks before the bleedings shown on the Figure. All bleedings were analyzed in the same ELISA assay at serum dilutions of 10,000 fold.

Very strong T-cell dependent responses against haptens can be raised against haptenated proteins, such as hen egg ovalbumin (OVA) or bovine serum albumin (BSA), when these haptenated proteins are absorbed on aluminum hydroxide and repeated small injections are given. The response that results may contain high levels of both IgG and IgE antibodies directed against the hapten which is coupled to the injected protein. As an example, the serum anti-fluorescein IgG response levels of three individual mice, which had been immunized by this protocol with fluorescein substituted OVA over a time period of several months and then were followed for a number of weeks without further exposure to antigenic material, is shown in FIG. 27. These mice were part of a large cohort which had all been immunized simultaneously according to the same protocol. Some of these mice were then injected intraperitoneally with polymers which we had previously determined were inhibitory. Such polymers were soluble fluoresceinated polymers of high hapten substitution density, but with molecular weights under 100,000. These polymers were injected to test their ability to suppress an ongoing high level anti-fluorescein IgG antibody response (cure). The results from the injection of three different such polymers on the serum levels of individual mice are shown in FIGS. 28, 29 and 30, where the time scale of bleedings is the same as in FIG. 27.

Figure 28:
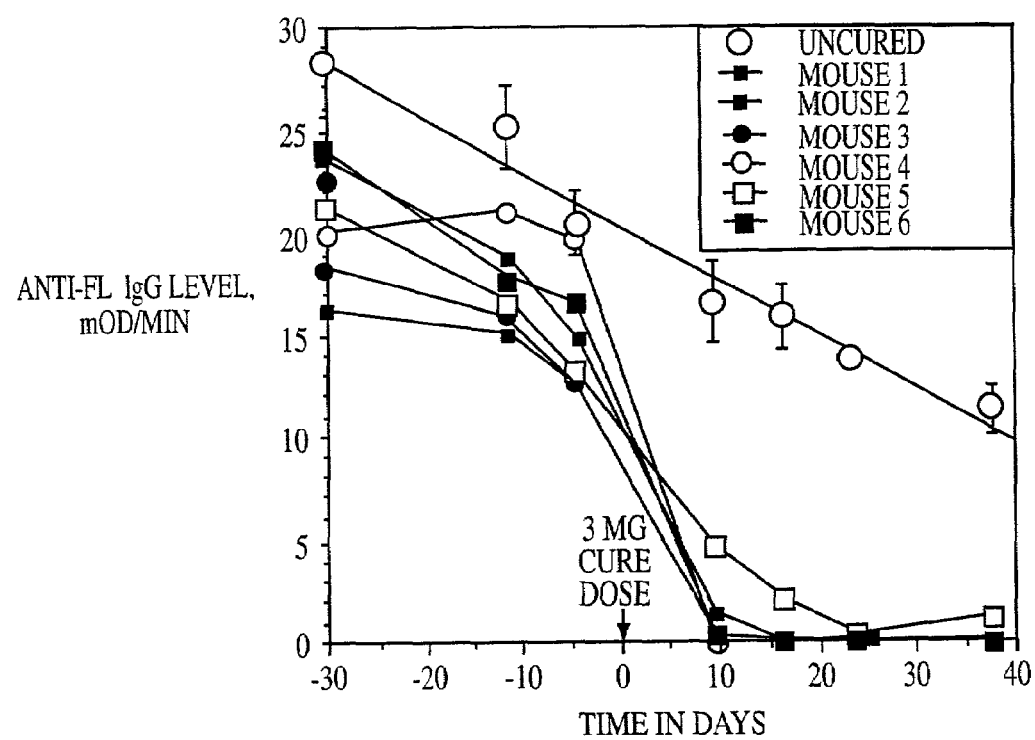
FIG. 28. Cure of anti-fluorescein IgG serum antibody level by the fluoresceinated polyacrylamide polymer FL30-Pa50, i.e., a 50 kD polyacrylamide polymer substituted with 30 fluorescein hapten groups. The time at which the dose of 3 mg of polymer was given has been arbitrarily designated day 0 on the time scale. The open circle data points are the averages of the data points shown in FIG. 27 for unsuppressed mice, with standard deviations and a least square fit straight line indicated.

The data in FIG. 28 show that, unlike the unsuppressed mice shown in FIG. 27, the mice which received a 3 mg does of a multiple FL substituted FL-Pa, FL30Pa50, had strongly diminished serum anti-Fl IgG antibody level for a period of a month or more. Of the 6 suppressed mice, the serum antibody levels of 5 mice fell quickly to levels too low to measure and remained so for the entire period. The serum antibody level in the sixth mouse fell more slowly and showed a slight recovery at the end of the time period.

Figure 29:
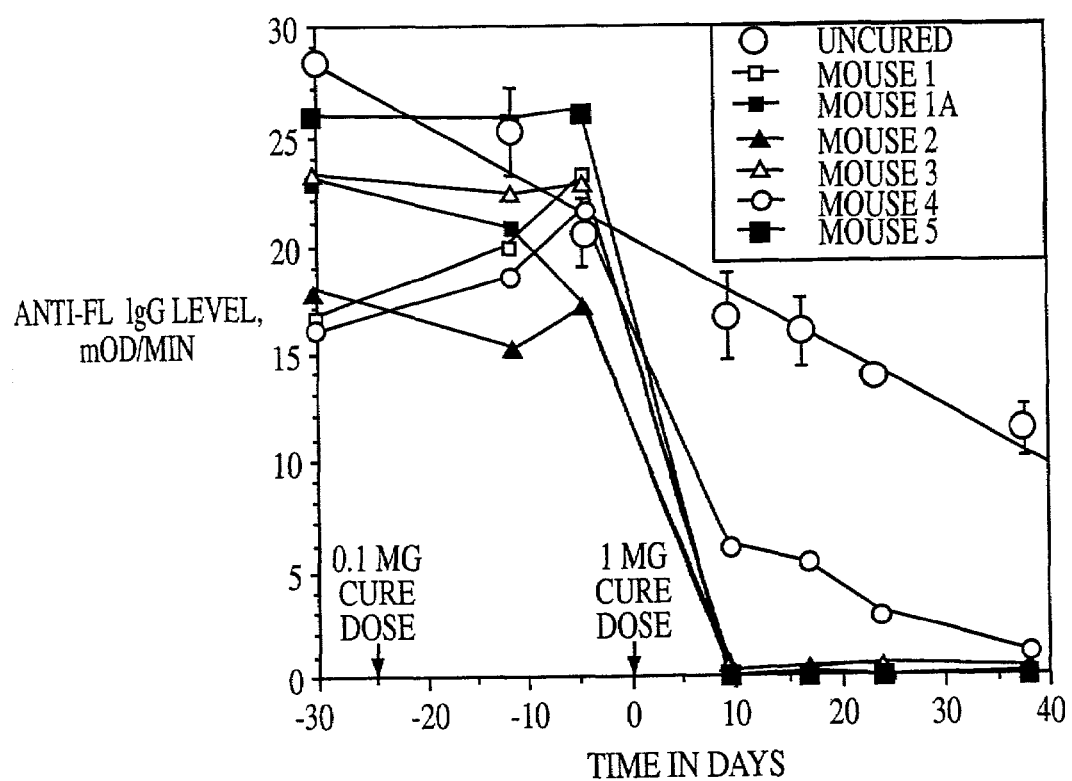
FIG. 29. Cure of anti-fluorescein IgG antibody level by the fluoresceinated dextran polymer FL25-Dex70, i.e., a 70 kD dextran polymer substituted with 25 fluorescein hapten groups. The time at which the dose of 1 mg of polymer was given was arbitrarily designated day 0 on the time scale. The open circle data points are the averages of the data points shown in FIG. 27 for unsuppressed mice, with standard deviations and least square fit straight line indicated.
Figure 30:
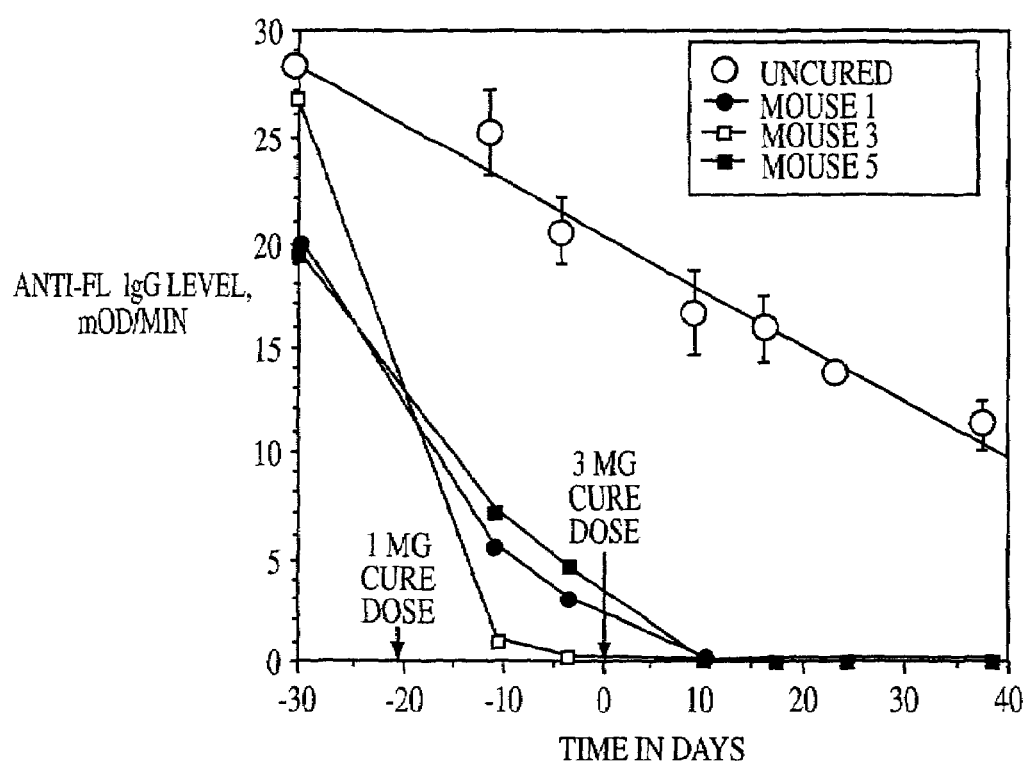
FIG. 30. Cure of anti-fluorescein IgG antibody response by the fluoresceinated dextran polymer FL30-Dex80, i.e., a 80 kD dextran polymer substituted with 30 fluorescein hapten groups. The time at which the dose of 3 mg of polymer was given was arbitrarily designated day 0 on the time scale. The open circle data points are the averages of the data points shown in FIG. 27 for unsuppressed mice, with standard deviations and least square fit straight line indicated.

When the polymer was dextran, FIG. 29, a dose of 0.1 mg of FL25Dex70 had no apparent effect on the serum anti-FL IgG antibody level, whereas a subsequent dose of 1 mg caused total suppression in 5 of the mice. The sixth mouse showed a sharp drop to a low level, followed by a slow and steady decline thereafter. The data in FIG. 30 show that a dose of 1 mg of FL30Dex80 caused a very substantial, but not total, suppression of the serum level of anti-FL IgG antibody. However, a subsequent dose of 3 mg brought about total suppression.

From the combined data of FIGS. 27, 28, 29 and 30, it is apparent that the injection of milligram quantities of appropriate haptenated polymers into an immunized mouse can cause profound and prolonged suppression of the level of serum anti-hapten IgG antibodies. This can be considered equivalent to the "cure" of an established humoral immune response.

In a subsequent experiment, an effort was made to test for the suppression (cure) of a high level anti-fluorescein response by the parallel measurement of the serum levels of both IgG and IgE (reaginic) antibodies, as well as the determination of the number of splenic lymphocytes producing anti-fluorescein antibody of the IgG class. In order to measure these different indices of suppression in the same experiment, a large number of mice were stimulated simultaneously with FL-OVA on aluminum hydroxide and subsequently subjected to different protocols of suppression and restimulation.

Very strong immune responses against the hapten, fluorescein, were raised in a large group of CAF1 mice by repeated injection of various doses of OVA which had been chemically substituted with fluorescein isothiocyanate to the level of 4.5 fluorescein hapten groups per ovalbumin molecule. In order to generate a strong and uniform immune response, the FL-OVA was adsorbed onto the adjuvant, aluminum hydroxide, Al(OH)$_3$, in the ratios of 0.1, 1, or 10 μg of FL-OVA per mg of aluminum hydroxide. A quantity of the resulting antigenic preparation containing 1 mg of Al(OH), was injected intra-peritoneally into a series of mice in order to bring about a strong antibody response against the fluorescein. After the second injection of antigen, the resulting T-cell dependent anti-FL IgG antibody level in the serum was uniformly very high.

Figure 31:
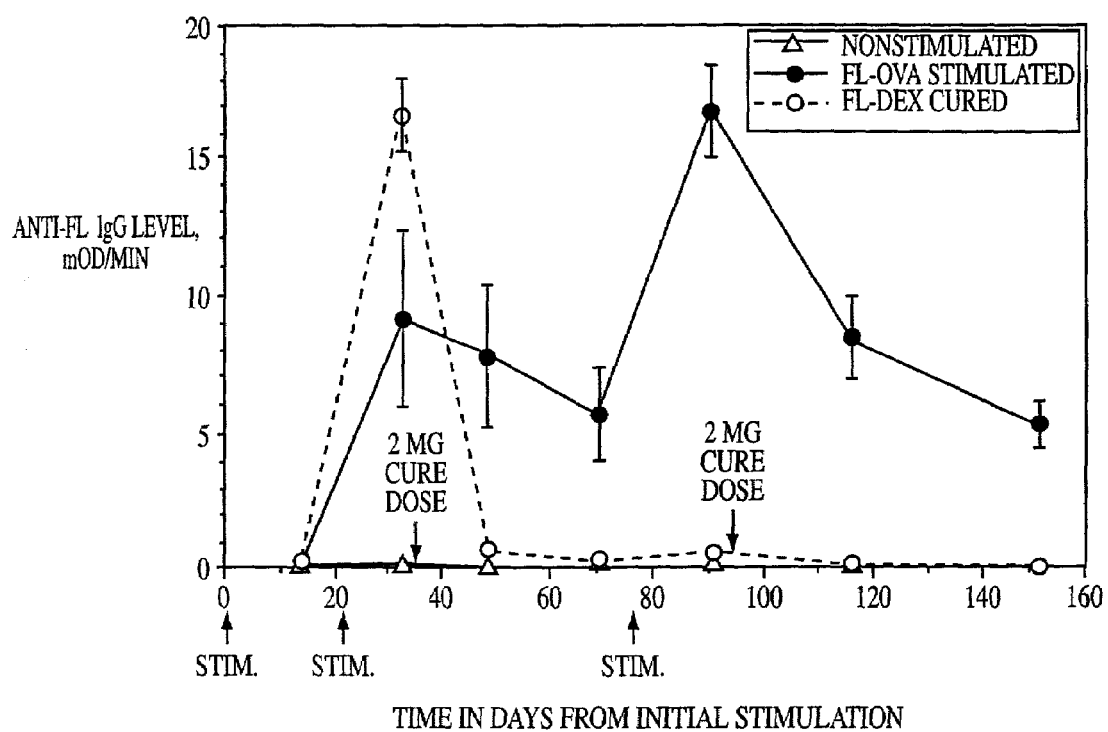
FIG. 31. Cure of anti-fluorescein IgG antibody response by the fluoresceinated dextran. ELISA assay results are shown from serum of mice diluted 100,000 fold. These mice were stimulated at the times indicated by doses of 10 μg of fluoresceinated ovalbumin absorbed on 1 mg of aluminum hydroxide. Cure was by injection of 2-mg of highly fluoresceinated dextran of average molecular weight approximately 40 kD at the times indicated. Data are from groups of three mice with mean and standard deviation indicated.
Figure 32:
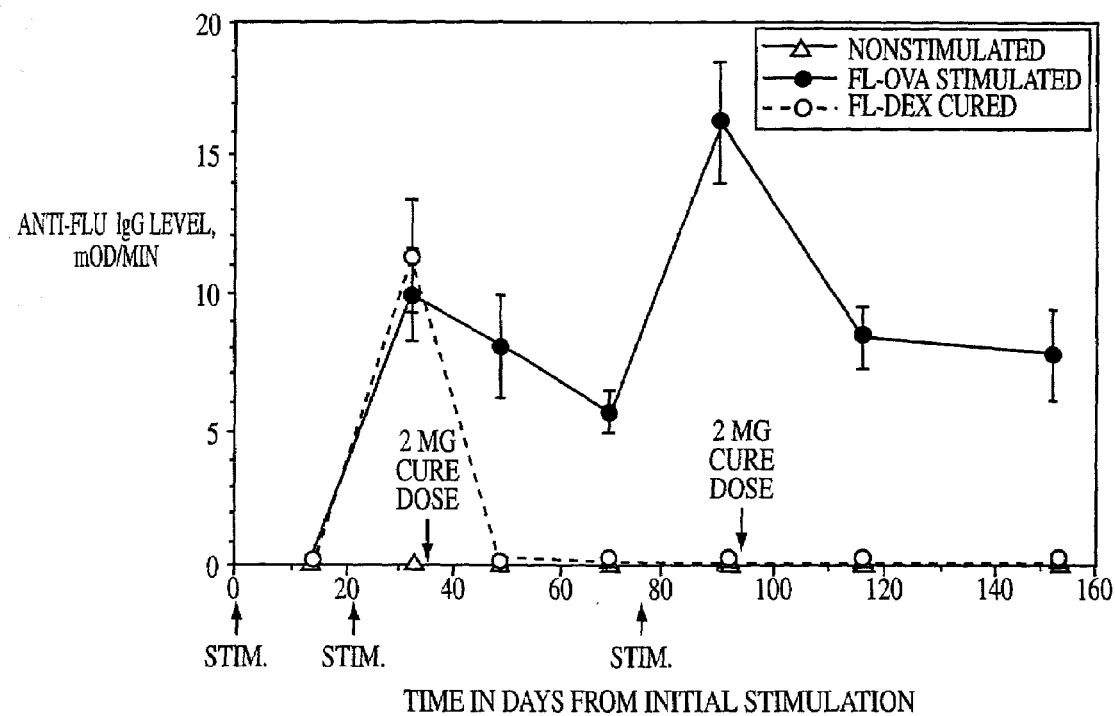
FIG. 32. Similar to FIG. 31, except that mice were stimulated at the times indicated by doses of 1 μg of fluoresceinated ovalbumin absorbed on 1 mg of aluminum hydroxide.
Figure 33:
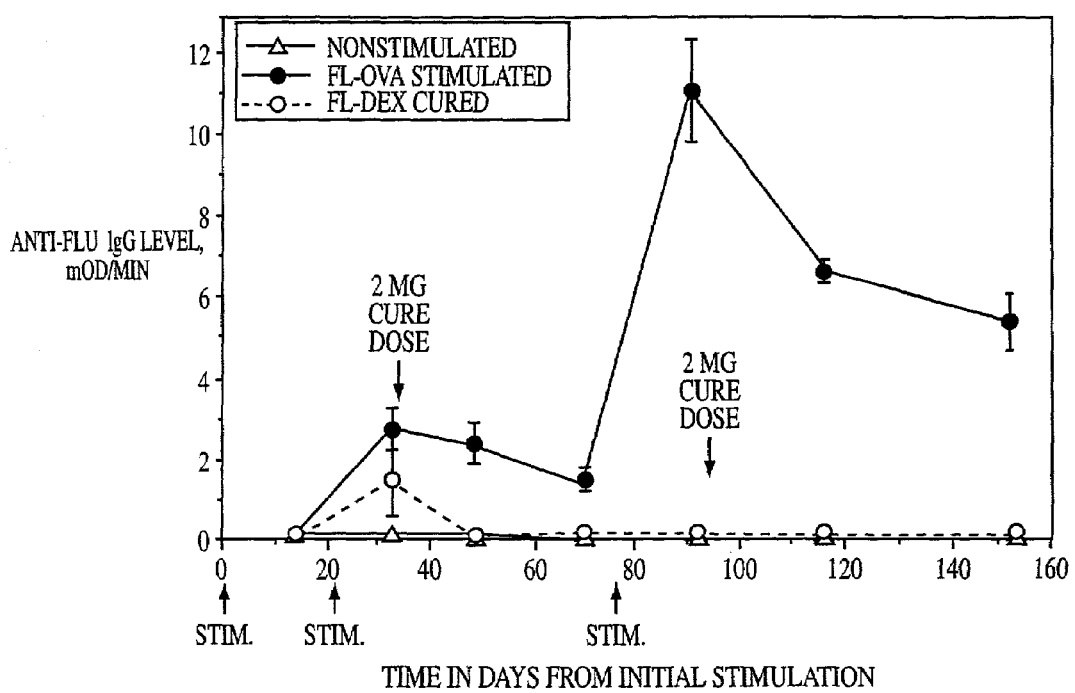
FIG. 33. Similar to FIG. 31, except that mice were stimulated at the times indicated by doses of 0.1 μg of fluoresceinated ovalbumin absorbed on 1 mg of aluminum hydroxide.
Figure 34:
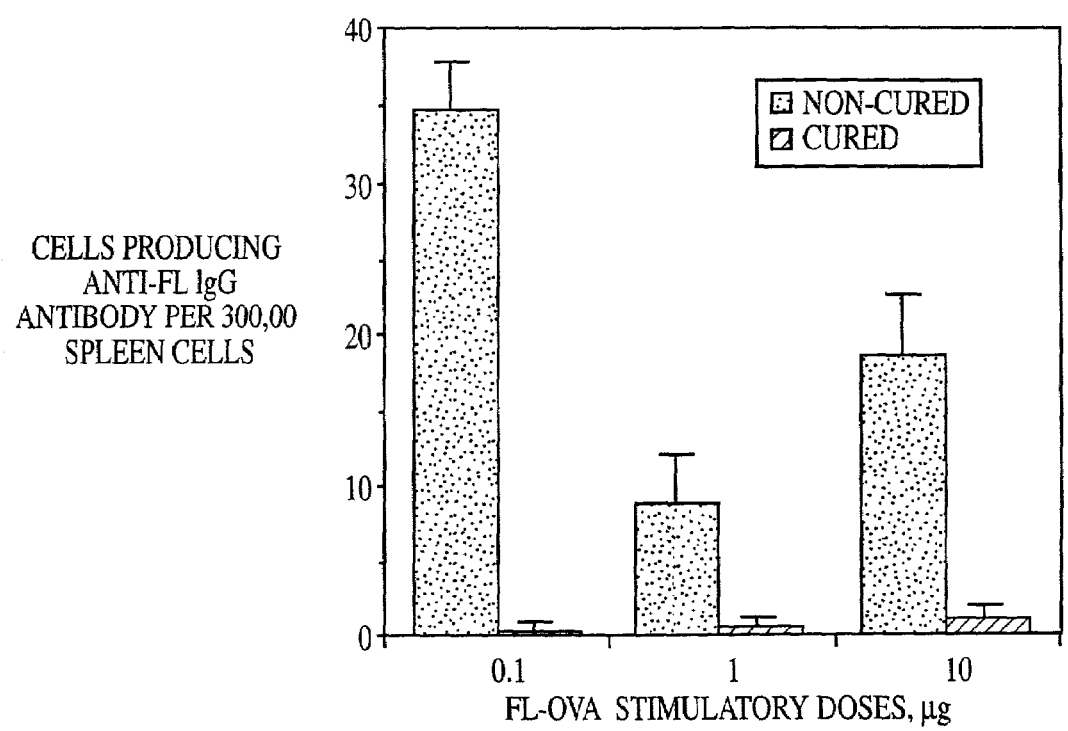
FIG. 34. Reduction by cure treatment of the number of splenocytes producing anti-FL IgG serum antibodies. The reduction in the population of antibody-secreting cells is substantial over a wide range of initially stimulatory doses of FL-OVA on aluminum hydroxide.
Figure 35:
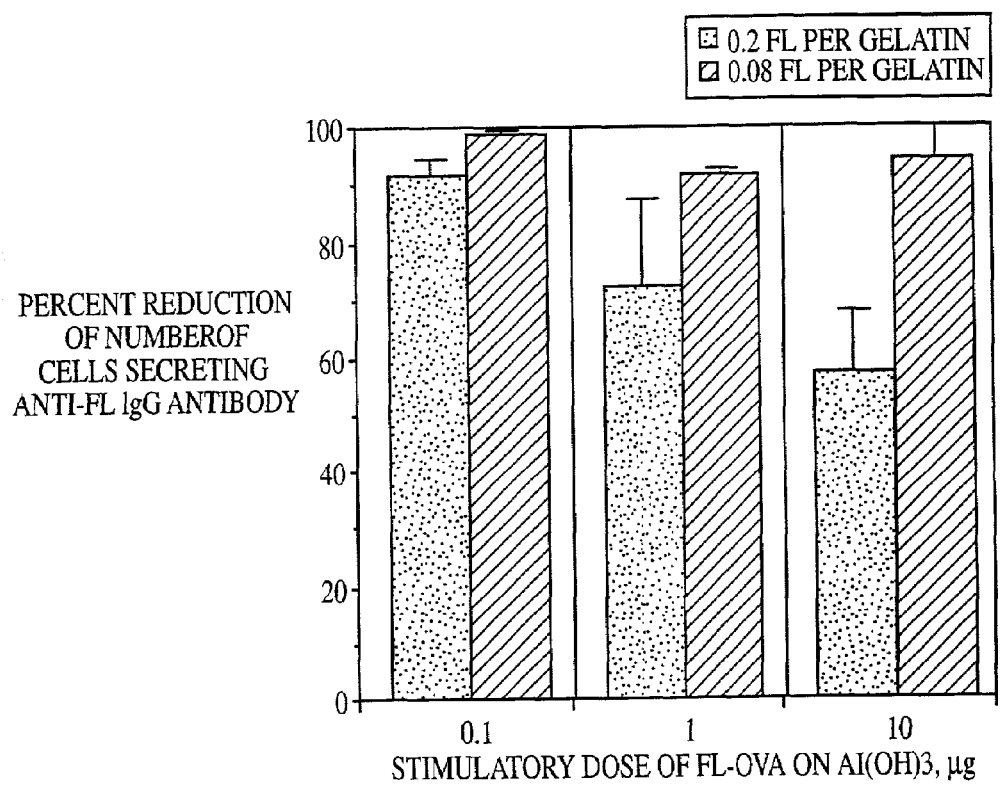
FIG. 35. Percent reduction of anti-fluorescein IgG producing lymphocytes from the spleens of mice which had been cured with FL-Dex. The mice had been treated as shown in FIGS. 31–33, with the final cure dose of FL-Dex given on day 95 and the spleen cells analyzed on day 125, 30 days later.
Figure 36:
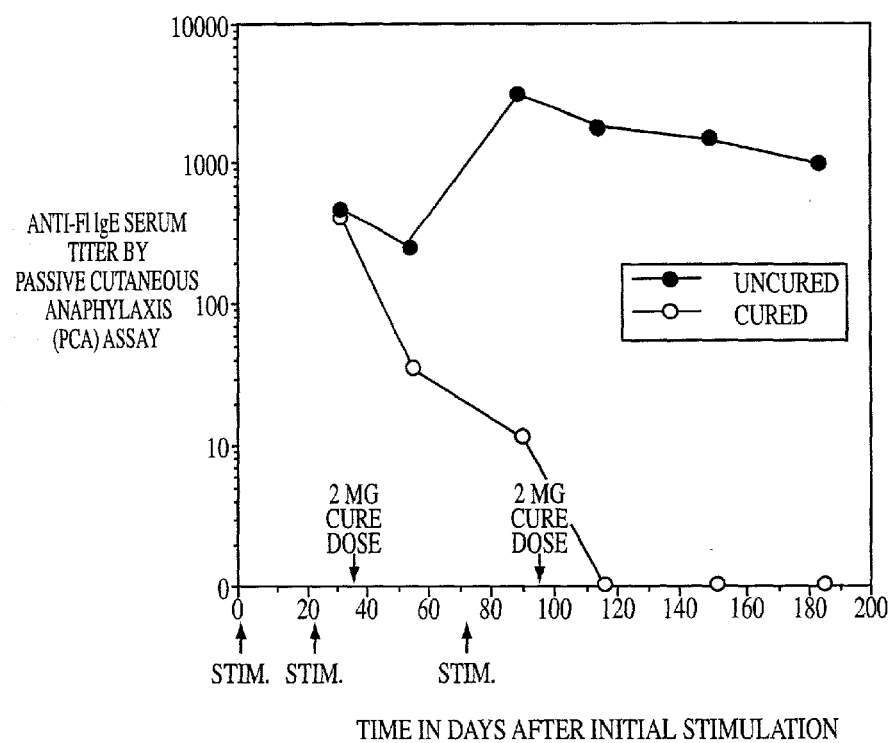
FIG. 36. Two separate PCA measurements, using different rats on different days, of the IgE antibody levels of pooled sera from cured and uncured mice, 6 mice per group. Stimulatory doses of 0.1 μg FL-OVA on 1 mg aluminum hydroxide were given on days 0, 21 and 71 to all the mice. For the cured mice, cure of the anti-fluorescein IgE serum antibody response was by treatment with 2 mg doses of FL30-Dex80 on days 34 and 95.

In order to measure the resulting anti-FL IgG antibody level, it was found necessary to dilute the serum 100,000 fold so that quantitative measurements could be made by ELISA technique. Measurement was made on 96 well plates coated with fluoresceinated gelatin, using affinity purified, alkaline phosphatase coupled anti-mouse IgG (μ chain) second antibody and optically following the rate of hydrolysis of nitrophenyl phosphate. As shown in FIGS. 31–33, anti-FL IgG measurements were made using a 100,000 fold serum dilution, with three mice per point, showing average and standard deviation of the measurements.

An effort was made to determine the generality of the observations by varying the stimulatory dose of FL-OVA over a 100 fold range, i.e., 0.1, 1, or 10 µg of FL-OVA on 1 mg of aluminum hydroxide were injected. A low level of fluorescein substitution on the gelatin which coated the ELISA analysis plates was used in order to emphasize the better binding, higher affinity, more clinically relevant anti-FL antibody molecules.

The elimination or "cure" of the resulting strong immune response was accomplished by the injection of an adequate dose (2 mg) of a non-stimulatory, but inhibitory, fluoresceinated polymer. The particular polymer used in this experiment was fluoresceinated dextran containing 30 fluorescein groups substituted on dextran with an average molecular mass of 80 kDa for resulting polymer (FL30-Dex80) as determined by high pressure liquid chromatography analysis. Since the mice had high circulating levels of antibody against fluorescein at the time they were "cured", it was important to administer the curative dose in steps over an extended time interval in order to avoid undesirable side reactions in the recipient animals. Accordingly, doses were increased a maximum of 10 fold every 2 hours beginning with an initial dose of 1 μg. This protocol produced no visual evidence of distress in the animal during or following the administration of the FL-Dextran. Cure doses were administered on day 35 when the immune response was very substantial, and also on day 95, following the attempt to restimulate the animals on day 75.

A direct comparison of the responses of the mice which had been stimulated repeatedly, with mice which had been stimulated and then cured, is shown in FIGS. 31, 32 and 33. These Figures show the dramatic decrease in the anti-FL antibody levels following the cure dose, as well as the lack of response to a subsequent restimulation on day 75. In order to demonstrate the range of effectiveness of the cure treatment, these Figures include data from mice which had been previously stimulated with high (10 μg), medium (1 μg) and low (0.1 μg) doses of the stimulatory antigen, FL-OVA on aluminum hydroxide. FIGS. 31, 32 and 33 clearly show that the serum anti-FLU IgG antibody level is very substantially reduced by a single cure treatment in each case, and is not restimulated by repeating the original process of stimulation.

In addition to the measurement of the level of circulating anti-fluorescein IgG antibody molecules in the blood, it is important to know the number of lymphocytes which are actively secreting such molecules into the serum. Ideally, suppression of an ongoing antibody response should cause a decrease in both the level of circulating specific antibody and also in the number of lymphocytes which secrete such molecules. The spot ELISA plaque assay method (Greene, G., et al., *J. Imm. Methods,* 129: 187–197, 1990) allows the measurement of the number of-spleen cells which are actively secreting IgG antibody specific for fluorescein.

When this method was used at 125 days to analyze the pooled spleen cells from 3 mice which had been stimulated three times (at 0,21 and 75 days) with different amounts of FL-OVA on aluminum hydroxide, substantial numbers of cells were found to be secreting anti-FL IgG antibodies in each case, FIG. 34, ("non-cured" bars). However, when cells were analyzed from the spleens of mice which had been stimulated by the same protocol, but which had also been cured on days 35 and 95 as discussed above, very substantial reductions in the number of cells producing anti-FLU IgG antibody molecules were found in each case, FIG. 34, ("cured" bars). These data indicate that the cure process not only eliminated the relevant free circulating antibody from the serum, but also eliminated most of the spleen cells capable of producing such antibody molecules. From the relative magnitudes of these two measurements the degree of inhibition of antibody producing cell caused by the suppression with FL-Dex was calculated and the resulting values are shown in FIG. 35.

The data shown above indicate that very substantial suppression of the specific immune response occurred as a result of the treatment with suppressive FL-Dex. From the data in FIG. 35, as well as additional data not shown, two different trends can be discerned relating the measured degree of suppression with the experimental conditions:

1. The measured suppression increases as the dose of immunogen which produced the immune response decreases, and 2. The measured suppression increases as the amount of epitope (fluorescein) coupled to the gelatin used for the spot-ELISA assay decreases, (i.e. the percent inhibition measured with 0.08 FL per gelatin is larger than when measured with 0.2 FL per gelatin). More measurements (data not shown) have indicated that this trend holds true across a wide range of hapten substitution density in the assays for cells producing anti-Fl antibodies in both the spot-ELISA assay for antibody-producing cells and the ELISA assay for serum levels of IgG antibody.

The two trends discussed above are consistent with the conclusion that the antibodies whose occurrence is most effectively inhibited by the suppressive polymers discussed above are those with the highest affinity for the hapten (FL). Since the correlation of allergy and autoimmune disease states with the presence of small amounts of high affinity antibody has often been made, this is a promising observation for application to medically relevant situations.

B. Cure of High Level Anti-FL IgE Response:

Many of the effects of allergy are due to the presence of antibodies of the IgE class, which can activate histamine releasing mast cells when exposed to the relevant antigenic material. A highly specific biological assay for the presence of such antibodies of the IgE class is the passive cutaneous anaphylaxis (PCA) test, wherein a few microliters of diluted serum from the animal under analysis is injected into the skin of a test animal. An hour or two later the test animal is injected intravenously with the relevant antigen in a saline solution containing soluble dye. In the skin regions where injected serum IgE antibodies against the antigen are present, visible dye color appears as a result of the activation of mast cells with subsequent release of mediator causing vascular leak. The greatest dilution of injected serum which will provoke an observable skin response is a measure of the IgE antibody titer in that serum. This is usually detectable down to a level of nanograms of the specific IgE antibody per ml of undiluted serum. When this biologically significant PCA test was applied to the serum from some of the mice which were stimulated and suppressed as shown in FIG. 32 above, the results shown in FIG. 36 were obtained.

FIG. 36 demonstrates that, after substantial levels of IgE anti-fluorescein antibody had been developed, a single injection of suppressive Fl-Dex brought the serum level of such IgE antibody to a very low level for several weeks (actually, the level was so low that it was experimentally indistinguishable from the background level of the measurement). Furthermore, the mice so treated were completely resistant to boosting with a repeated dose of antigen, whereas the control mice showed a very substantial increase in their IgE serum titer when boosted. It appears that the suppressive polymer injection caused a long lasting "cure" of an established allergic type response in the mice.

In summary, experimental tests of the ability of suppressive forms of fluoresceinated polymers to suppress or "cure" a strong ongoing T-cell dependent immune response against the fluorescein hapten have been made. The results indicate that clinically relevant IgG and IgE antibodies specific for the hapten can be effectively eliminated, as measured by dramatic and long lasting reductions in:

1. Serum anti-hapten IgG antibody level;
2. The number of splenic lymphocytes secreting anti-hapten IgG antibody; and
3. Serum anti-hapten IgE antibody level.

C. Reduction of Serum Anti-penicillin IgE

The penicillin allergy is among the most clinically distressing drug allergy since administration of penicillin (or its related compounds) is still the treatment of choice for many diseases. However, many people are allergic (i.e. show immediate-type hypersensitivity reactions) to penicillin or become so while undergoing long-term penicillin therapy. Described below are the data that indicate that the immune response to penicillin can, in fact, be specifically suppressed using this technology.

The experimental details that follow apply to the study set forth in this Example.

Animals:

CAF, (BALB/cXA) female mice were obtained from Cumberland Farms, Clinton, Tenn. and were approximately 10 weeks old when first immunized. Male Sprague-Dawley rats weighing 320–380 g were obtained from Holtzman Co., Madison, Wis.

Chemicals: Bovine serum albumin (BSA) Fraction V was obtained from Miles Laboratories, Inc. Penicillin G (sodium salt) and crystallized chicken ovalbumin (OVA) were obtained from Sigma Chemical Corporation, St. Louis, MO, p-Chloromercuribenzoate (PCMB) was obtained from Calbiochem, Los Angeles, Calif., Evans Blue was purchased from Eastman Kodak, Rochester, N.Y. and ethylene diamine (EDA) was ordered from MCB Manufacturing Chemicals, Cincinnati, Ohio.

Hapten-carrier Conjugates:

Benzylpenicilloyl-bovine serum albumin (BPO-BSA) and benzylpenicilloyl-ovalbumin (BPO-OVA) were prepared by incubating BSA or OVA with Penicillin G (benzylpenicillin) in 0.5 M $K_2CO_3$, pH 10.0 at room temperature (Nakawaga et al, Int. Archs. Allergy Appl. Immunol. 63:212 (1980)). Various incubation times yielded different epitope densities. The number of haptens per carrier is denoted by subscript, i.e. OVA substituted with four BPO groups is $BPO_4$-OVA. The degree of substitution was determined by a modification of the penamaldate assay (Parker, C. W. Methods in Immunology and Immunochemistry, Williams and Chase eds. Vol. I, p. 133, Academic Press, NY (1967)). 0.1 ml of $2\times10^{-3}$ M PCMB in 0.05 M carbonate, pH 9.2 is added to 1.0 ml of the penicilloyl-carrier conjugate in 0.05 M carbonate, pH 9.2. The approximate penicilloyl concentration should be 2 to $4\times10^{-3}$ M. After mixing and allowing to stand at room temperature for 5–10 minutes, a reading is made at 285 mµ ($\epsilon=2.38\times10^4$). The incremental increase, after correction for uncombined PCMB (0.038 at a final concentration of $2.82\times10^{-4}$M) and dilution (protein concentration is 91% of original) is due to the penamaldate formed from PCMB and the penicilloyl group.

Figure 37:
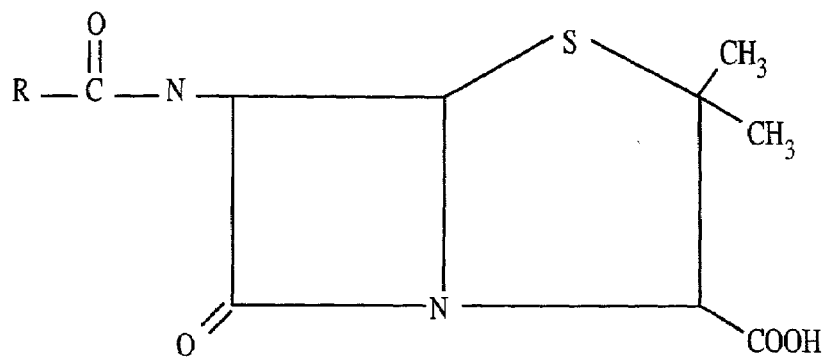
FIG. 37. The structures of penicillin and the penicilloyl hapten. R is a benzyl group for Penicillin G (benzyl penicillin). In the penicilloyl hapten, the internal amide bind of the β-lactam ring is replaced by an amide bind involving a primary amine from the carrier.
Figure 37:
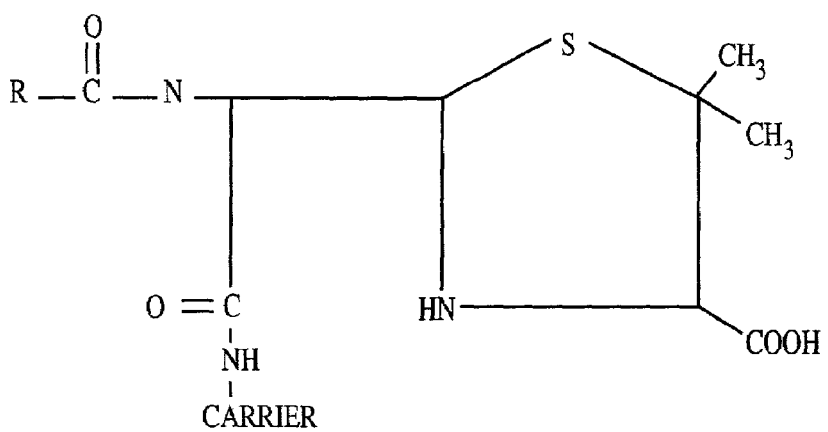

Benzylpenicilloyl-polyacrylamide (BPO-PA) was made by carefully size-fractionating linear PA by gel filtration as described above. Incubating the PA with ethylene diamene (EDA) at 50° C. for 90 minutes followed by extensive dialysis results in the formation of heavily substituted EDA-PA. This was then conjugated with penicillin by the method used to prepare the protein conjugates. The resulting haptenated polymer was then refractionated by gel filtration to relative size homogeneity. (See FIG. 37)

Immunizations: Two groups of four mice each were injected intraperitoneally (i.p.) with 1 µg of $BPO_4$-OVA on 1 mg $Al(OH)_3$ in 0.10 ml of 0.01 M Tris, 0.15 M NaCl buffer, pH 8.3. A booster injection of 3 µg $BPO_4$-OVA on 1 mg $Al(OH)_3$ was given two and one-half weeks after the primary injection. Approximately three and one-half months after the primary immunization, the mice were re-challenged with 3 µg $BPO_4$-OVA on 1 mg $Al(OH)_3$.

Suppression: One of the above groups of four mice received an i.p. injection of 1 mg of BPO-PA in 0.25 ml phosphate buffered saline (0.01 M phosphate, 0.15 M NacL, pH 7.4 PBS). This polyacrylamide had an approximate molecular weight of 40,000 (determined by equilibrium ultracentrifugation) and was substituted with approximately 25 BPO groups per polyacrylamide molecule. Prior studies have shown this preparation of BPO-PA to be non-immunogenic at any dose.

Assay:

IgE content was determined by a modification of the passive cutaneous anaphylaxis (PCA) assay (Ovary, Int. Archs. Allergy Appl. Immun. 3:293 (1953)). Equal volumes of serum from mice in each group were pooled and 0.1 ml volumes of diluted serum were injected into the skin of rats. After two hours, 4 mg $BPO_8$-BSA plus 10 mg Evans Blue Dye in 0.5 ml PBS was injected intravenously (i.v.) and twenty minutes later the rats were sacrificed, skinned, and the titer (the reciprocal of the highest dilution yielding a lesion at least 5 mm in diameter) was determined.

Figure 38A:
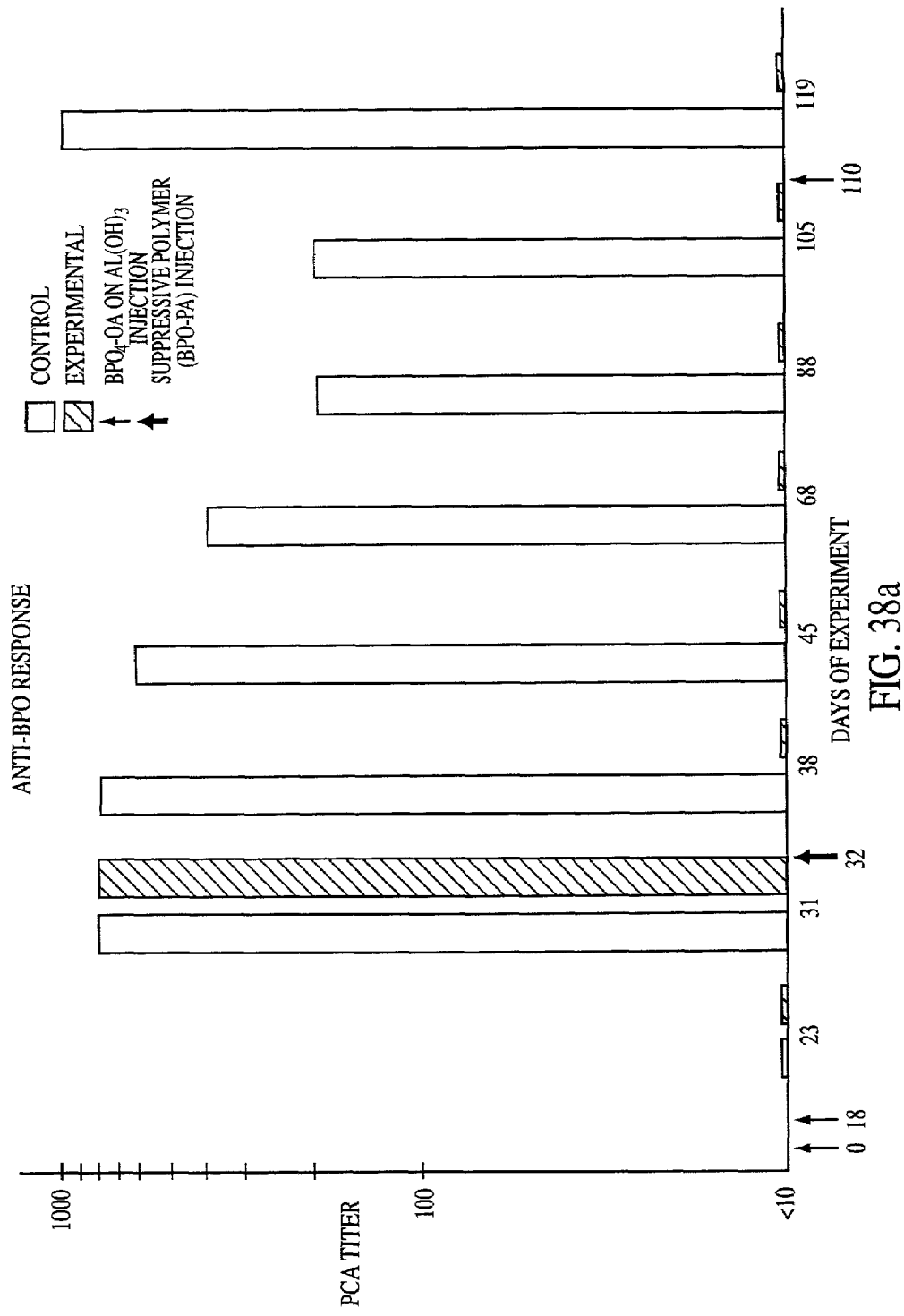
FIG. 38. Administration of the suppressive polymer BPO-PA virtually abolishes the anti-BPO response (FIG. 38a), while the anti-OA response (FIG. 38b) is unaffected. Not only does the anti-BPO titer remain undetectable for two months, but the mice are tolerized by the BPO-PA and are unresponsive to a "booster" injection given on day 110.
Figure 38B:
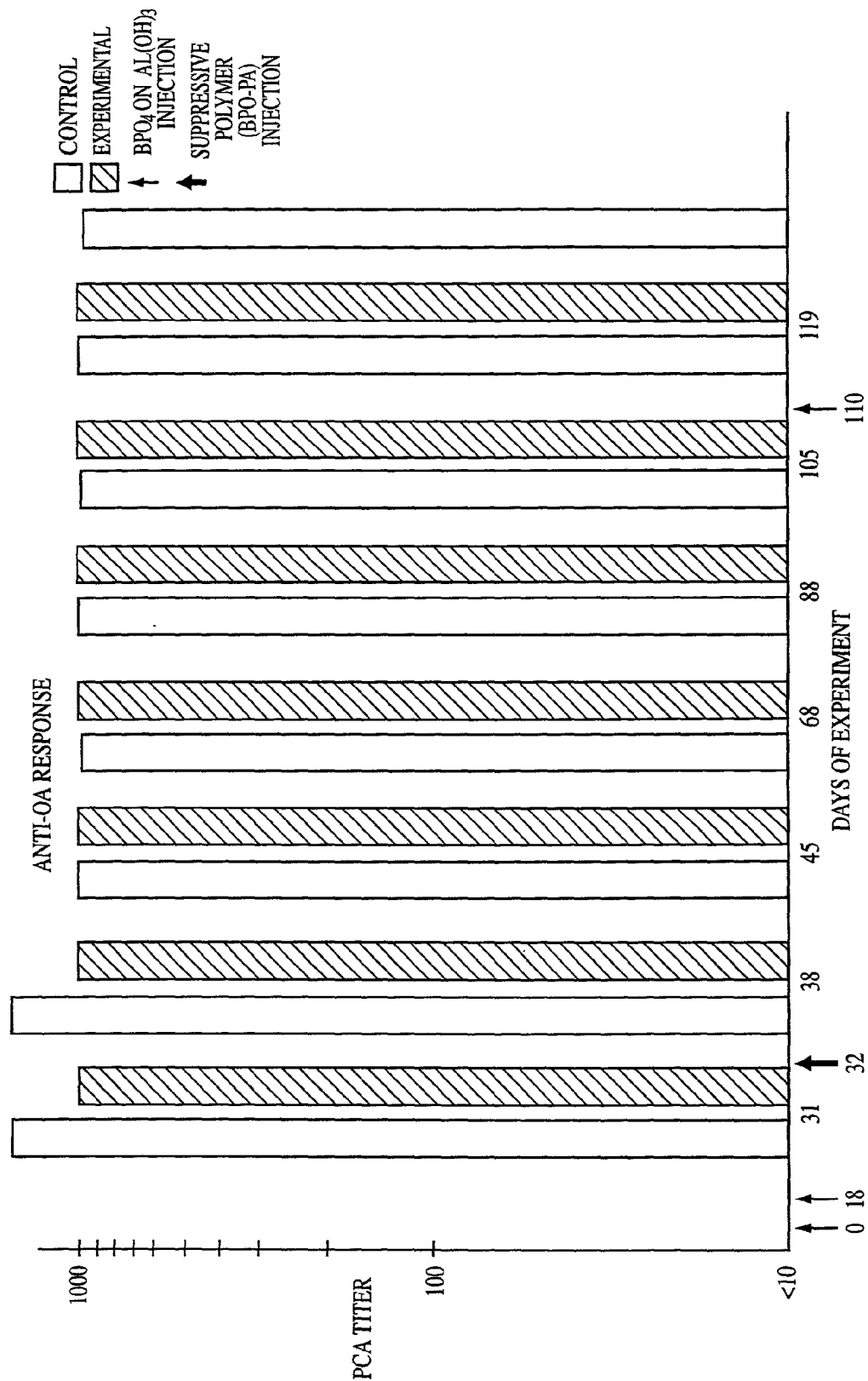

Mice injected with $BPO_4$-OVA on $Al(OH)_3$ gel developed an anti-BPO IgE response (FIG. 38) as measured by PCA assay. This anti-BPO response is the murine correlate of human penicillin allergy. Four mice were injected with a suppressive dose of 1 mg of the polyacrylamide haptenated with BPO (BPO-PA). Within one week of receiving the suppressive dose of BPO-PA, serum levels of anti-BPO IgE in the experimental group declined by greater than 98% (FIG. 38a) while the levels of anti-OVA IgE remained constant (FIG. 38b). That is, the response of the experimental group to the BPO hapten, after suppression, was less than 1/80 of the control group response.

Approximately two and one-half months after the experimental group received its suppressive dose of BPO-PA, both groups were boosted with an i.p. injection of 3 µg of $BPO_4$-OVA on 1 mg $Al(OH)_3$. The mice in the control group had an anti-BPO response even greater than the original response while the mice in the experimental group were unresponsive to the "boosting" injection (FIG. 38a). Therefore, the suppression induced by the BPO-PA is not only fast (within one week), but lasts several months. Furthermore, it tolerizes the mice so that they are unresponsive to additional exposure to the BPO hapten.

Figure 39:
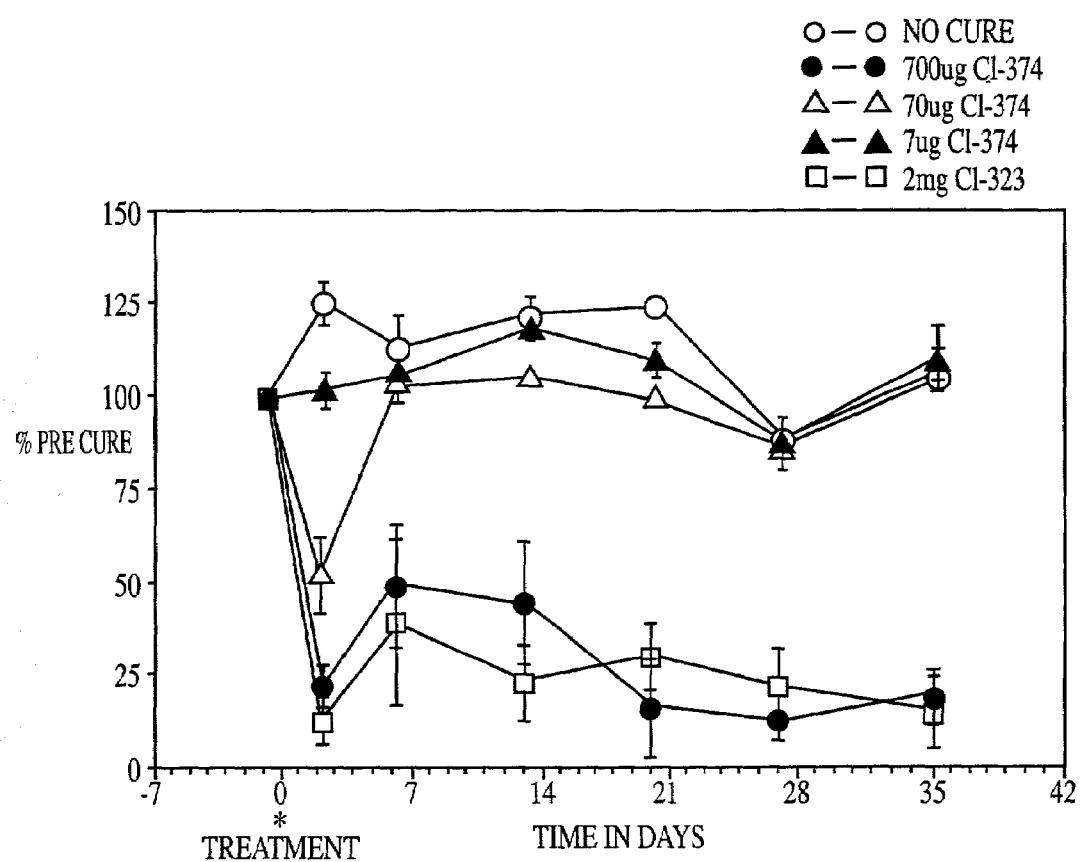
FIG. 39. Supression of ongoing anti-fluorescein IgG response using valence restricted scaffolds.

D. Use of Valence-restricted Cyclodextrin Based Conjugates as Suppressive Constructs Balb/c mice were immunized and subsequently boosted twice with Fl-BSA adsorbed on to aluminum hydroxide to raise high titre IgG anti-Fl antibodies. These mice were divided into groups and treated either with the valence-restricted scaffold bearing seven FITC groups (CI-0374) as described in Example 1H above at three different doses or with dextran of 70,000 dalton substituted with 60 FITC groups (CI-0323) at a dose shown in previous experiments to be optimally suppressive. Another group was immunized with the buffer alone as a control. Mice were bled at intervals following these treatments and sera were assayed by ELISA for IgG anti-Fl antibodies as described in previous Examples. It is apparent (see FIG. 39) that the valence-restricted scaffold can induce dose-dependent, long-lasting suppression of the anti-FL response similar to that induced by the Fl-dextran construct.

Example 10

T-cell Dependent Antibody Responses to Proteins and Protein Oligomers

An assumption of the Immunon model of immune responsiveness is that monomeric protein molecules, which contain only a single copy of each kind of potential epitope, should not be immunogenic if administered in monomeric soluble form. However they may be immunogenic if administered in polymerized form or if they are polymerized into closely spaced arrays absorbed on adjuvants, on cell surfaces, as soluble or insoluble aggregates, or by some other process within the body.

Immunogenicity of Polymeric BSA: Measurement of Anti-BSA IgM:

The results obtained from the study of polymerized BSA will be described first.

Figure 40:
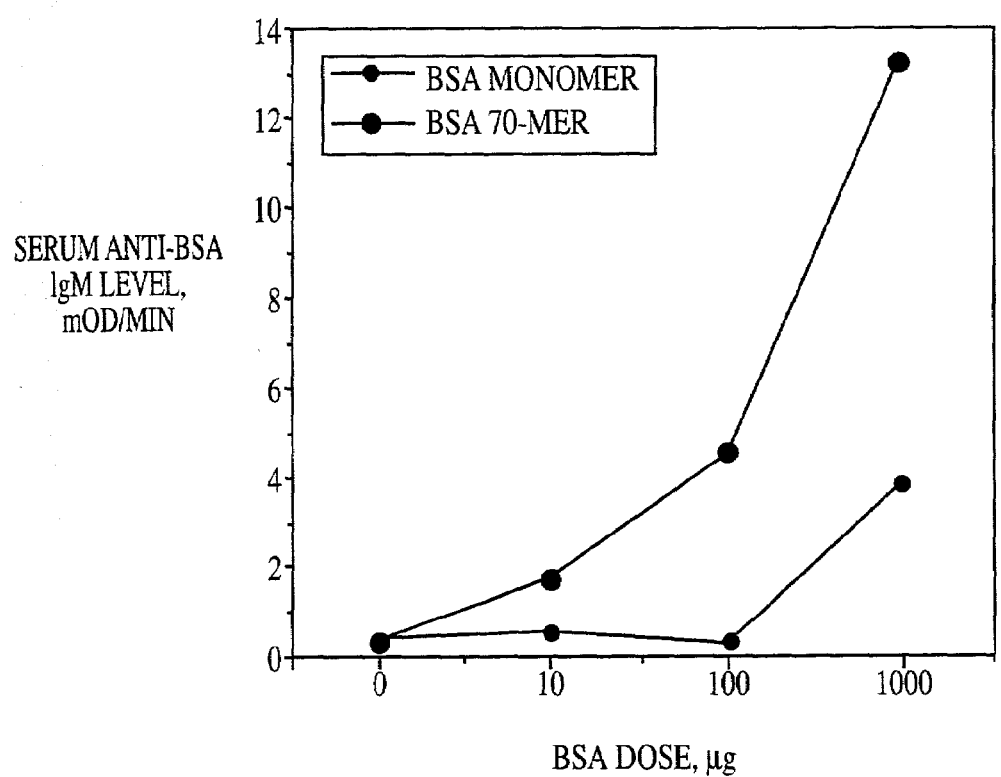
FIG. 40. Serum anti-BSA IgM dose-response for monomeric and polymerized BSA. CAF1/J mice were injected with 10, 100 or 1000 μg of monomeric (68 kD) or carbodiimide cross-linked 70-meric (5000 kD) preparations of BSA. The IgM antibody response was measured by ELISA at day 6 for serum dilutions of 200 fold. Data are the average of 3 mice per point.

As was the case with the previous haptenated dextran studies, the anti-BSA IgM serum levels were found to rise rapidly, peaking at about 6 days and then declining to a plateau level. FIG. 40 shows that soluble highly polymerized BSA (a "70-mer," containing 70 BSA monomers) is capable of raising IgM antibodies even at very low doses, whereas monomeric BSA requires substantially higher doses to bring up detectable IgM levels against BSA.

Figure 41:
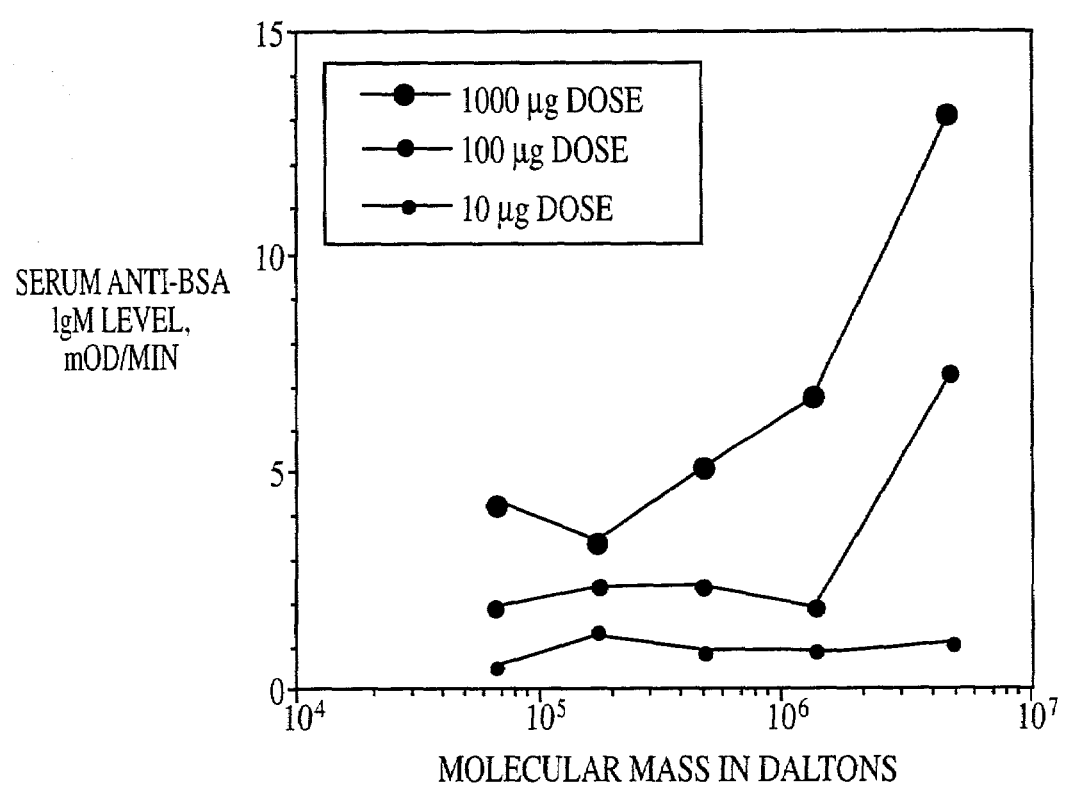
FIG. 41. Effect of BSA multiplicity on response. Data similar to that shown in FIG. 40 for BSA complexes having molecular multiplicity of approximately 1, 3, 7, 20 and 70 (BSA monomer has a mass of 68 kD).

When data from a series of polymers of BSA of differing molecular weight is compared, in FIG. 41, the immunogenicity, as measured by IgM levels at day 6, is found to increase most rapidly at the higher molecular weights, but is strongly dose dependent at all molecular weights.

Figure 42:
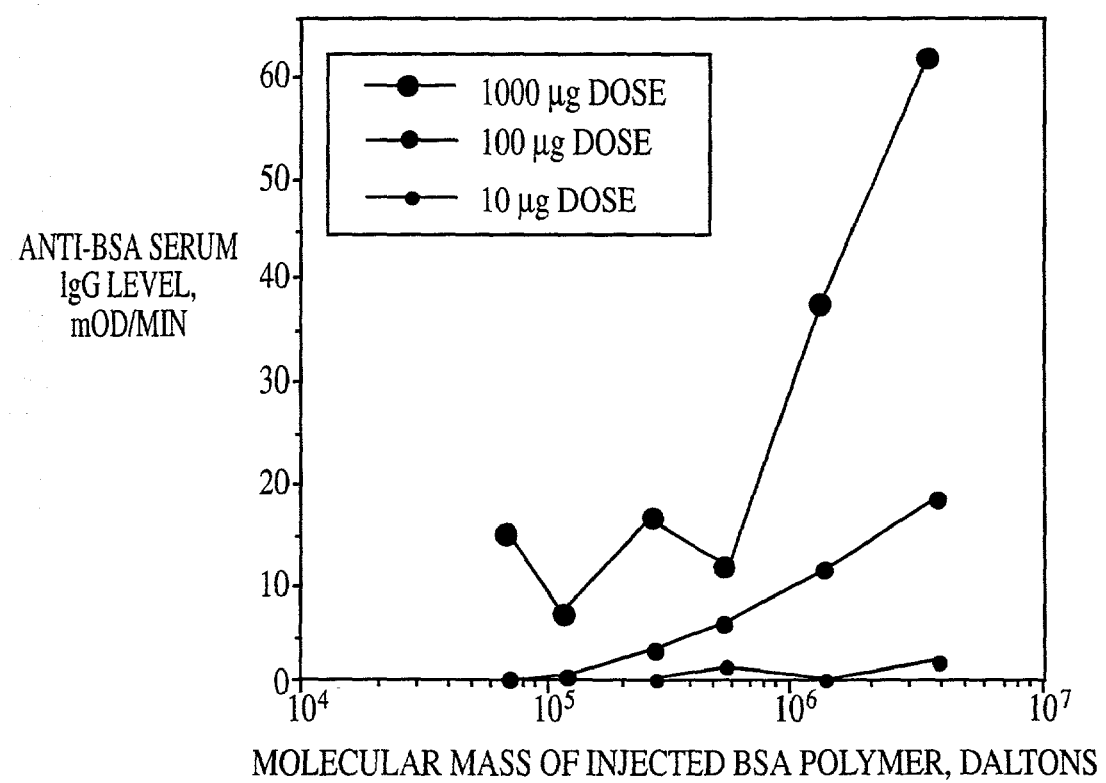
FIG. 42. Effect of BSA multiplicity on serum IgG response. Serum anti-BSA IgG antibody levels 14 days after a single injection of BSA polymers of different molecular masses at various doses. Serum was diluted 1000 fold, 3 mice averaged per point.
Figure 43:
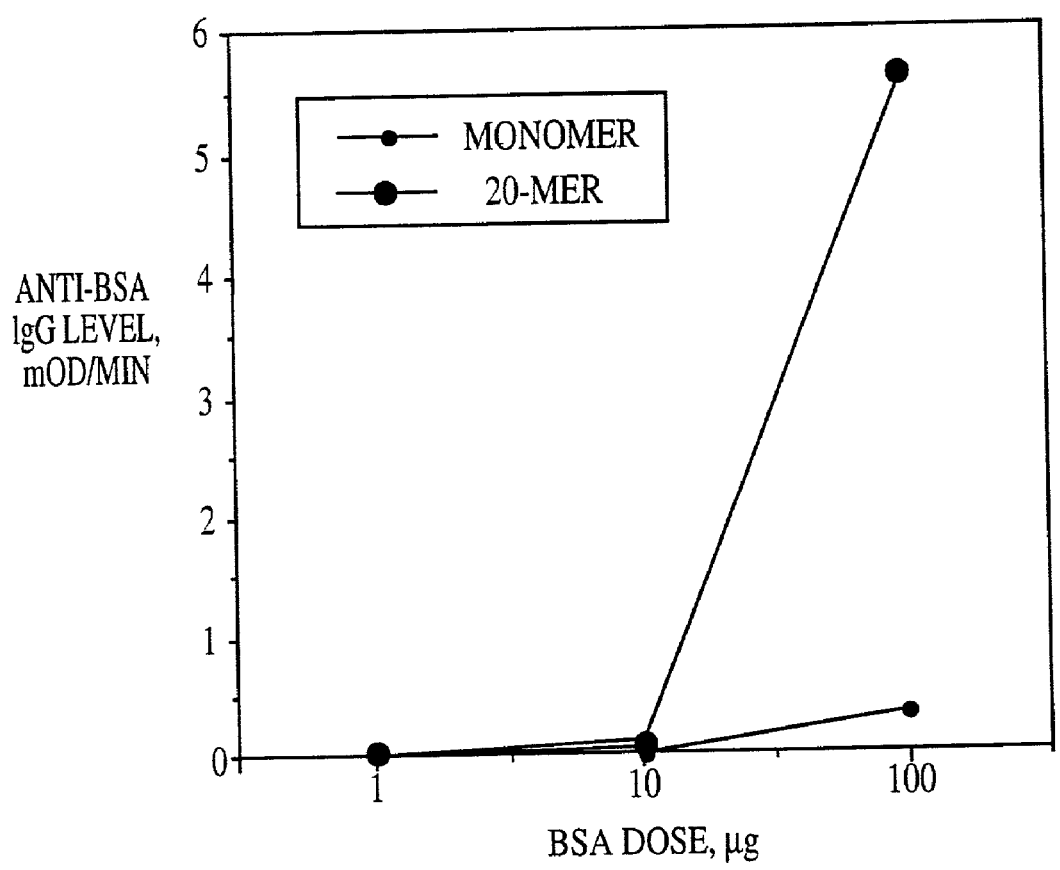
FIG. 43. Serum anti-BSA dose-response for multiple injections of monomeric or carbodiimide cross-linked 20-meric BSA. The anti-BSA IgG response is shown after three injections given 30 days apart. Serum was diluted 4000 fold for ELISA assay.
Figure 44:
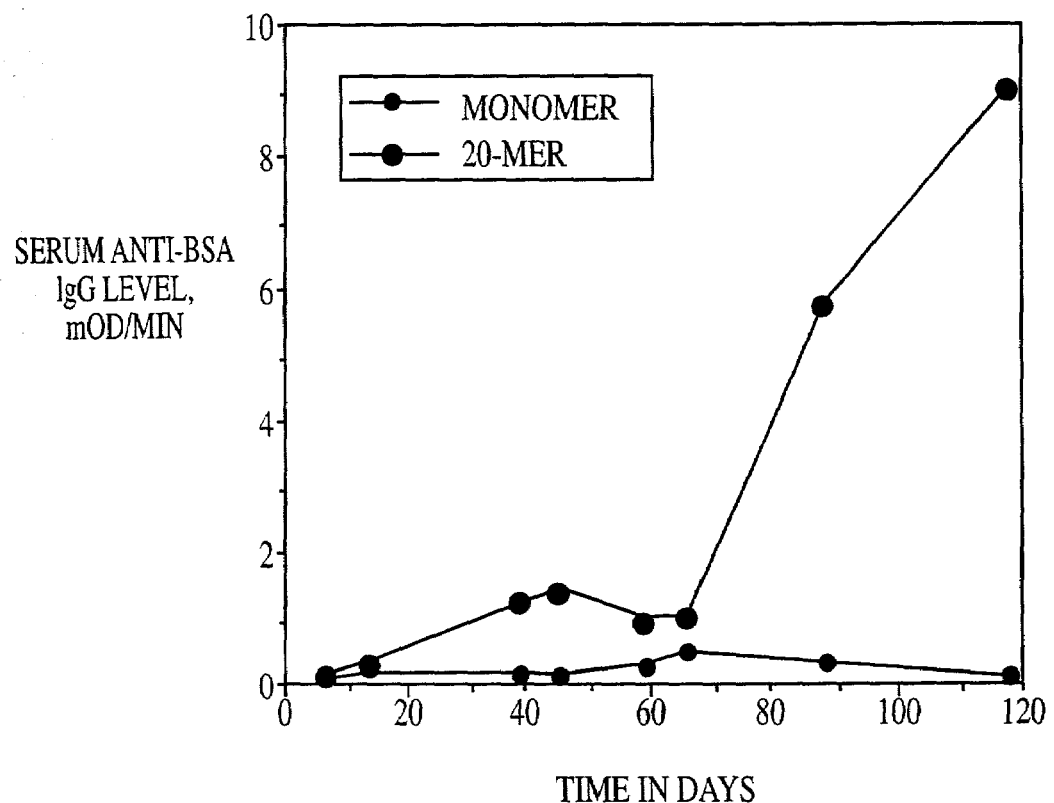
FIG. 44. Effect of multiple injections on serum anti-BSA IgG response to a BSA "20-mer" given at very low dose. One µg of either monomeric or carbodiimide cross-linked 20-meric BSA polymer, 1400 kD, was injected on a monthly basis. A total of 5 Ag (5 injections) was given. Data are averaged from 3 mice.

Immunogenicity of Polymeric BSA: Measurement of Anti-BSA IgG:

By day 14 after the injection of the soluble polymers of BSA, substantial isotypic class switching had occurred and anti-BSA IgG antibodies were found to be present for some combinations of antigen dose and molecular mass, FIG. 42. When multiple small injections of BSA polymers were given, the response was very dependent upon the molecular weight of the BSA polymer. FIG. 43 illustrates experiments in which mice were given three injections 30 days apart of 1, 10, or 100 μg of BSA polymers in saline. As was true for single injections, the anti-BSA IgG serum levels were strongly dose and polymer size dependent. FIG. 43 indicates that monomeric BSA is not very effective in producing an anti-BSA IgG response even after repeated injections in saline at doses up to 100 μg. In contrast, preparations containing polymers of substantial size were very effective. This observation was confirmed when the total number of consecutive injections, on a monthly basis, was increased to five, as is illustrated in FIG. 44. FIG. 44 illustrates more clearly a trend which was evident in the previous Figures, i.e., that significant amounts of antibody are raised only to the polymeric form of soluble BSA when small doses are administered. It is also clear that even very small doses (1 μg) of highly polymeric protein can be immunogenic in the absence of adjuvant, if they are administered repeatedly.

Figure 45:
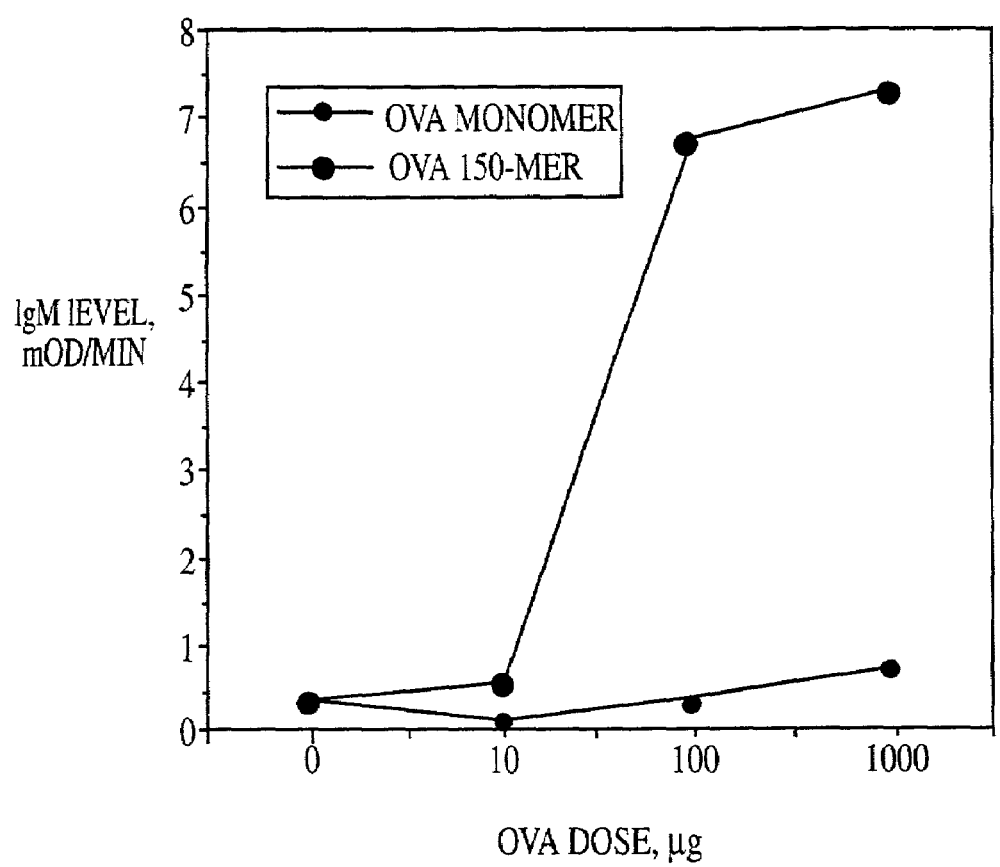
FIG. 45. Serum anti-OVA IgM dose-response 5 days after injection of OVA monomer or glutaraldehyde cross-linked 150-mer.

Immunogenicity of Polymeric OVA: Anti-OVA IgM:

Results which were very similar to those obtained with polymerized BSA were obtained when polymerized ovalbumin, OVA, was used as antigenic material. The primary response to monomeric and highly polymerized OVA, both injected in saline, is shown in FIG. 45.

Figure 46:
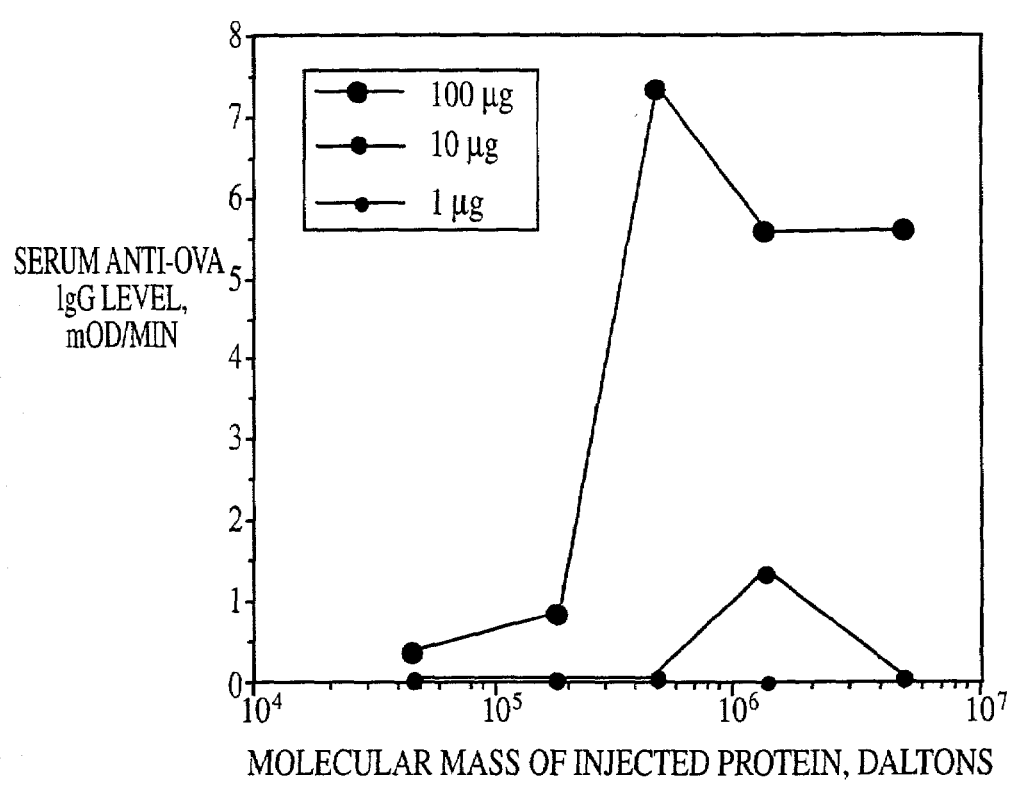
FIG. 46. Serum anti-OVA IgG response to multiple injections of monomeric or glutaraldehyde cross-linked OVA fractions of different molecular sizes. Serum was diluted 4000 fold for ELISA assay.

Immunogenicity of Polymeric OVA: Anti-OVA IgG:

When glutaraldehyde polymerized OVA was size fractionated and several different doses of the individual fractions were injected three times at monthly intervals, the immune response was found to depend strongly on the OVA-polymer size and the dose, FIG. 46 The variations of response with dose and polymer size are roughly comparable to those found with polymers of BSA, FIG. 42.

Figure 47:
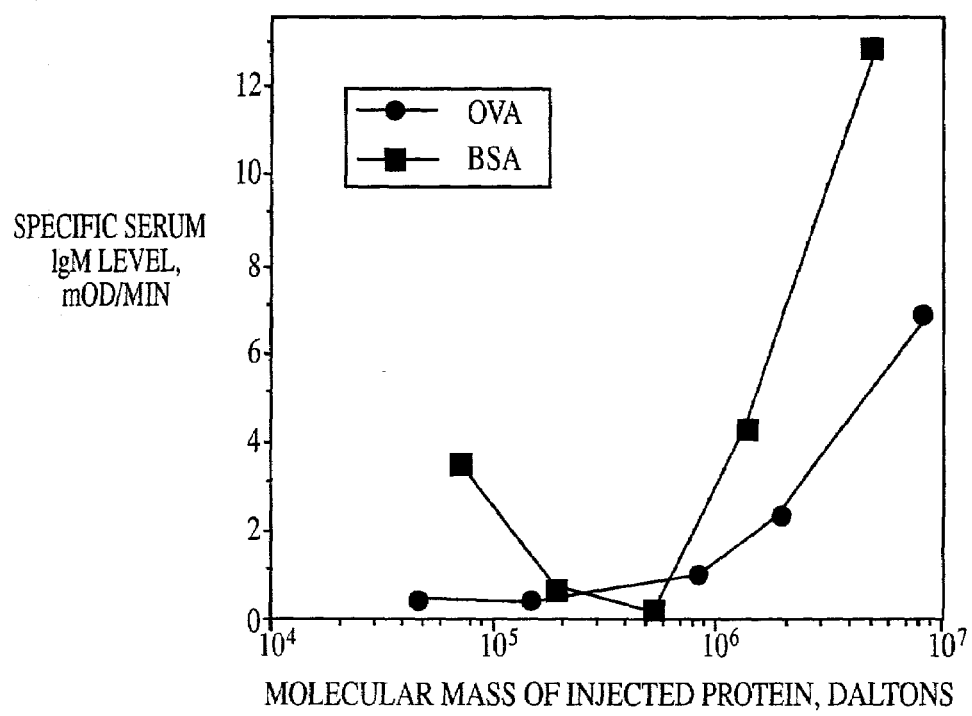
FIG. 47. Comparison of serum IgM response generated by monomeric and various polymeric sizes of BSA and OVA. Three monthly 1 mg injections of monomeric or polymerized BSA or OVA were given in saline. Serum was diluted 200 fold.

A comparison of the primary IgM responses to 1 mg of either polymerized BSA or polymerized OVA, at short times after administration of antigen, FIG. 47, shows a substantial degree of similarity. Both Figures show increasing immunogenicity with increasing polymerization.

Figure 48:
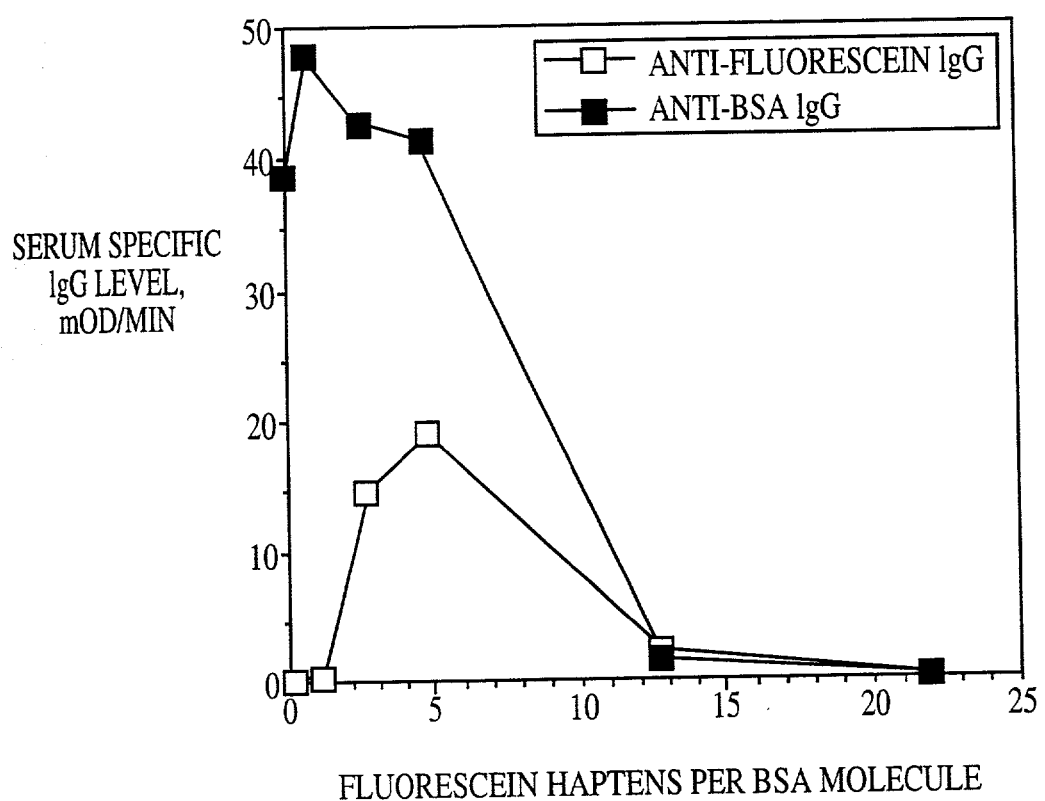
FIG. 48. comparison of the anti-fluorescein and anti-BSA serum IgG response generated by a fluoresceinated BSA polymer. Samples of a BSA polymer (20-mer) as haptenated with fluorescein isothyocyanate, yielding preparations with different amounts of fluorescein per BSA monomer unit. Mice were injected with 4 biweekly doses of 100 µg each in saline, for a total dose of 400 µg. Serum was assayed for IgG antibodies to fluorescein and to BSA.

Anti-fluorescein Response Generated by Fluoresceinated BSA Polymers:

In order to determine the immune response to a hapten on polymerized protein, fluorescein was coupled to BSA polymer at a number of different levels of substitution, and the immune response was determined after several injections, as shown in FIG. 48.

The results demonstrate that the anti-hapten response was of the desired IgG isotype. It rose with increasing degree of substitution, peaking at approximately 5 fluoresceins per BSA monomer unit, or a total of 100 fluoresceins per BSA 20-mer. It then fell rapidly to very low levels with increasing substitution. On the other hand, the immune response to the BSA itself remained relatively constant with increasing fluorescein substitution until approximately 5 haptens had been added, whereupon it, rather surprisingly, also fell rapidly. This indicates that there is also an optimum level of substitution of polymerized proteins with peptide epitopes of types potentially useful for vaccines. Construction of maximally immunogenic adjuvant-free vaccines using this type of chemistry is contemplated.

It can concluded from the foregoing results that:

1) Polymeric BSA and OVA, administered without adjuvant, stimulate considerable IgM and IgG anti-protein responses.

2) The immunogenicity of these poly-proteins increases with increasing protein multiplicity.

3) Immunogenicity of poly-proteins is strongly dose-dependent, the immunogenicity increasing with increasing dose.

Example 11

Suppression of Antibody Responses to Peptides from Extrinsic Antigens and Autoimmune Antibody Responses Against Epitopes on Endogenous Proteins The following materials and methodologies are referenced in the description of experimental results that follows:

Mice—Balb/c femal mice were obtained from either the Jackson Laboratory, Bar Harbor, ME or Harlan/Sprague Dawley, Indianapolis, Ind. They were used at 8–10 weeks of age.

Figure 49:
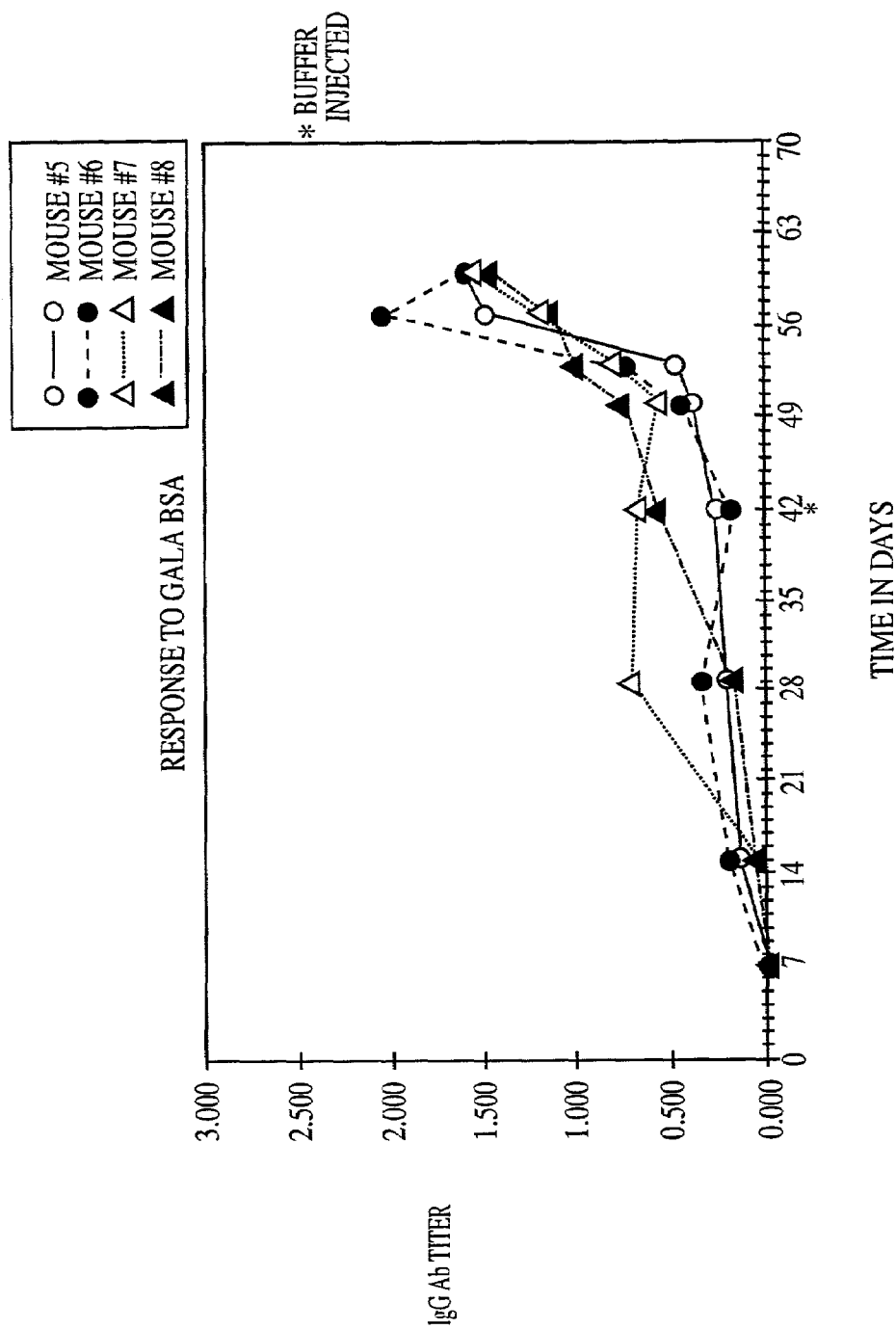
FIG. 49. Levels of IgG peptide (GALA)-specific antibodies in serum.
Legend: Mouse #5 ○—○; Mouse # 6 ○ - - - ○;
Mouse #7 Δ - - - ; Mouse #8 ▲-•-•-▲; *=buffer injected.

Immunization Protocols—To raise IgG antibodies (Abs), mice were given a single intraperitoneal injection of 10–50 μg peptide-BSA conjugate adsorbed on aluminum hydroxide. Test bleeds were taken at various times thereafter and anti-peptide IgG Ab titers measured. To test the immunogenicity of peptide-dextran conjugates, mice were injected intraperitoneally with 100 µg doses of dextran backbone to which peptides were conjugated at various substitutions ratios. Bleeds were taken at weekly intervals and levels of IgM and IgG peptide-specific Abs in the sera were measured (FIG. 49). The suppressive peptide-dextran conjugates were administered in the following way unless otherwise indicated: 1, 10 and 100 µg doses were injected at 2-hourly intervals, with the 1 and 10 µg doses being given intravenously whereas the high dose was given intraperitoneally ("cure" treatment). Subsequent doses to maintain suppression were given at weekly intervals.

ELISA Assay—Antibody titers were measured by standard solid-phase ELISA assay. Microtiter plates (Immunolon II, Dynatech Labs, Alexandria, Va.) were coated overnight at 4° C. with peptide-gelatin conjugates at 0.1 µg/well. After blocking plates with PBS/gelatin, various dilutions of antisera were added and incubated at room temperature for two hours. Plates were washed and antibody binding was detected with horseradish peroxidase-conjugated isotype-specific antibodies (Kirkegaard and Perry Labs, Gaithersburg, Md.) followed by the ABTS substrate. Data are expressed as $OD_{405mm}$ of the ABTS product. Antibodies directed against linker regions were detected using an irrelevant peptide-gelatin preparation and these readings were subtracted from those for specific binding.

The first peptide chosen for study was a sixfold repeat of a glutamic acid-alanine-leucine-alanine sequence (EALA using single letter amino acid code) followed by the peptide sequence glycine-alanine-glycine-arginine-glycine-aspartic acid-serine-proline-alanine-amide SEQ ID NO:21. This peptide will be referred to herein as (EALA).

Figure 50:
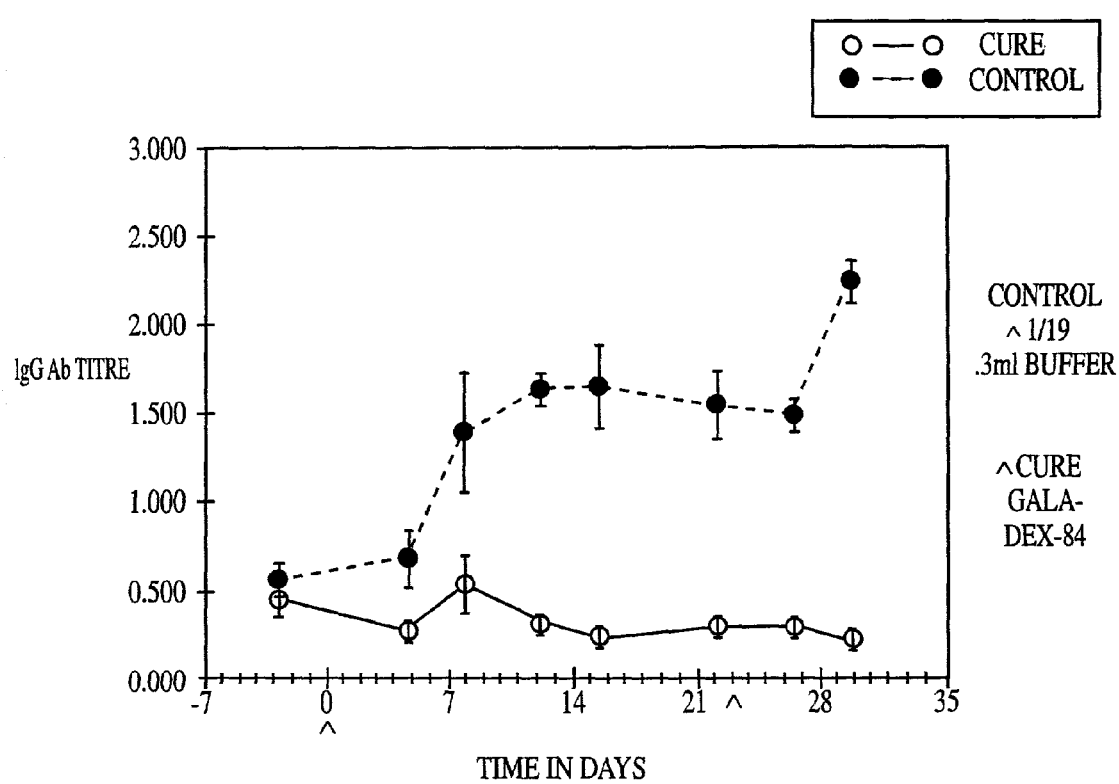
FIG. 50. Prevention of rise in antibody levels by EALA-DEX-84. Cure ○—○; control ●-•●; Control 1/19 0.3 ml buffer; Cure EALA DEX-84.

Defined EALA-dextran conjugates were synthesized on 84,000 MW Dextran (EALA-Dex$_{84}$) that were verified to be non-immunogenic. Using these conjugates, the ongoing anti-EALA IgG response elicited by EALA-BSA was suppressed. Forty-six days after injection of EALA-BSA, these mice were split into two groups one of which received EALA-dex$_{84}$ in increasing doses of 1, 10 and 100 µg dextran backbone and the other of which received three injections of buffer alone. The mice were bled three days later and at three day intervals thereafter and the antisera tested for any reduction in their anti-EALA IgG titers. FIG. 50 clearly indicates that EALA-dex$_{84}$ prevented the rise in Ab levels that continued to progress in the untreated mice. The low levels persisted for at least 21 days. At this point another cure was performed using the same regimen to see if the low response of suppressed mice could be effectively abolished altogether. Although the response was not reduced further by EALA-dex$_{84}$ administration, it was maintained at low levels for at least another 14 days while that of the control mice still appeared to increase.

For the second study a different peptide was chosen that has been studied extensively by the immunologic community. This peptide, referred to as 159, represents residues 331–339 of chicken ovalbumin (OVA). The peptide consisting of residues 323–339 of this protein, referred to here as 104, is a dominant epitope on OVA recognizable by helper T cells particularly in H2$^d$ mice.

When 104 is arrayed on dextrans of high molecular weights, and these conjugates are injected into Balb/c (H2$^d$) mice, high IgG Ab responses are rapidly obtained. In addition, when 104 was arrayed on BSA, precipitated with aluminum hydroxide and injected into mice, an extremely vigorous antibody response was seen. Interestingly, it was found that approximately 40–50% of the antibody response to 104, either arrayed on dextran or BSA could be attributed to the C-terminal 10 amino acids represented by 159. This system then is analogous to a more complex antigen (such as a protein) wherein a short, linear sequence of amino acids is recognized by a significant proportion of the antibodies generated to the entire antigen.

Using this model, the ability to specifically and selectively suppress a response to a defined epitope of a more complex system was demonstrated. Initial studies designed to better characterize this system revealed that peptide 159, when arrayed on 65,000 MW dextran was not immunogenic, as predicted by the Immunon model. However this peptide can be recognized by B cells since BSA conjugates raise good antibody responses to 159. Furthermore, as mentioned above, a substantial portion of antibodies raised by the 104-conjugates are directed against 159 as indicated both by direct binding in ELISA assay and by competition assay using free 159 to inhibit binding of anti-104 antibodies to 104-gelatin.

Figure 51:
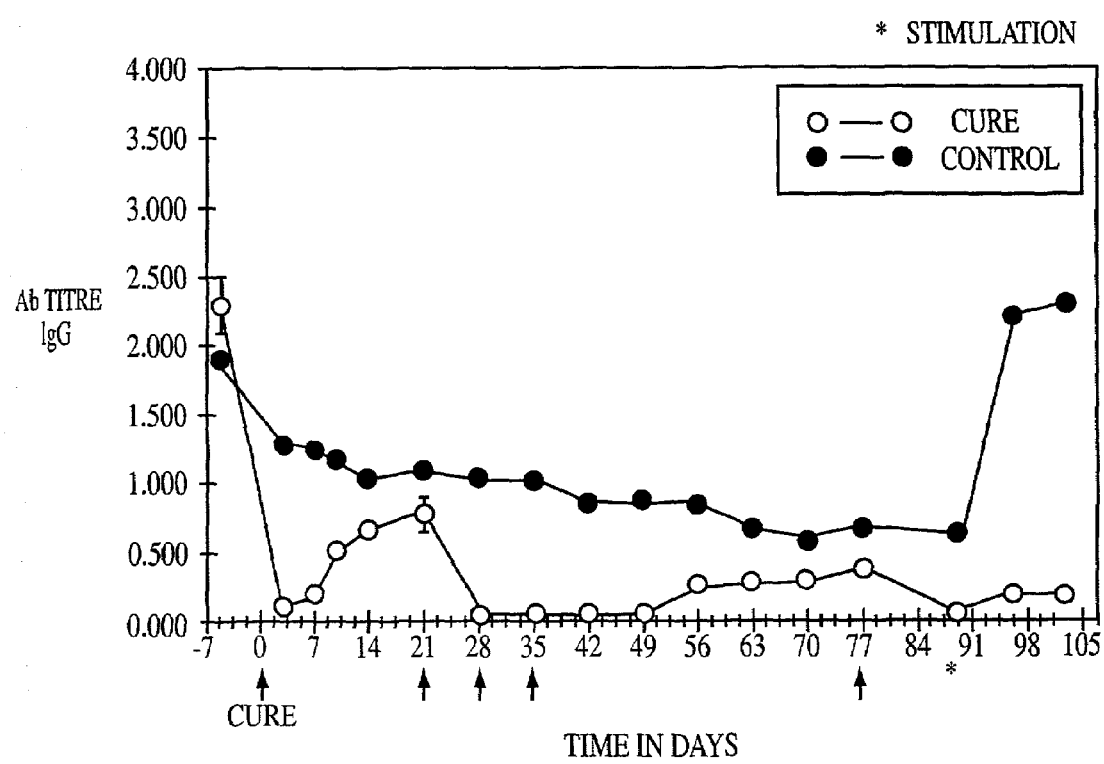
FIG. 51. Specific suppression of 104 response directed towards the 159 epitope(s). Bleed after day 77 cure was on day 83; on day 84—bleed d7=d91. Legend ↑ "Cure" mice were injected with various doses of $159_{10}$-$dex_{40}$; control mice were injected with saline. * Control and cured mice were injected intraperitoneally with 10 µg 104-BSA.

FIG. 51 demonstrates the ability to suppress specifically the portion of the 104 response that was directed towards the 159 epitope(s). IgG antibodies were raised to 104 by injection of Balb/c mice with 104-BSA adsorbed on to alum. High titers were raised both to 104 and to 159 (FIG. 51). Forty days after the immunizing injection (day 0 in the Figure), groups of eight mice were either injected with saline or with 1, 10 and 100 µg dextran of 40,000 molecular weight conjugated with 159 at a ratio of 10 moles peptide/mole dextran (ie 159$_{10}$-dex$_{40}$). Mice were subsequently bled at day 3 and then at 7 day intervals and assayed for responses to both 159 and 104. FIG. 51 shows the responses after the cure and indicates that the response to 159 was dramatically reduced immediately after treatment but that the antibody titer rebounded virtually to control levels within 14 days. The response to 104 in treated mice followed the same pattern of reduction and recovery as the 159 response but was only reduced at day 3 to about 60% of the precure response whereas the 159 response is reduced to about 9% of precure levels. In other words, approximately 40% of the response to 104 is removed by administration of 159$_{10}$-dex$_{40}$ indicating that this portion of the 104 response is directed against epitopes in the 159 sequence. In fact, up to 40% of the 104 response can indeed be completed successfully with soluble 159 in solution phase competition assays (data not shown).

The cure was then repeated as before but using 200 µg as the largest dose. In-addition, 200 µg doses were given at weekly intervals thereafter to see if continuous administration of suppressive conjugate would maintain a chronic suppression of the 159 response. FIG. 51 shows that this second cure again essentially completely inhibited the response to 159 measured 7 days later and this was comparable to the reduction seen after the first cure (the response was 13% of precure levels 7 days after the first cure and 10% of precure levels 7 days following the second cure).

Furthermore, the response to 159 remained suppressed over the next 40 days during which 159$_{10}$-dex$_{40}$ was injected intraperitoneally at weekly intervals. Injections were then stopped and antibody responses were monitored for approximately 30 more days and were found to stay suppressed, although the responses did tend to increase slightly so that the titers approached the declining antibody levels of the control mice (FIG. 51). At this point, mice were again cured (day 77) with 1, 10 and 100 µg 159-dex and subsequently boosted intraperitoneally with 104-BSA, as were the control mice. It is clear that cured mice can withstand this challenge since although the antibody responses of control mice were substantially boosted (as would be expected), those of the cure mice were not significantly changed from pre-challenge levels.

It appears therefore that the effect of $159_{10}$-$dex_{40}$ is not only to suppress the ongoing anti-159 antibody response but also to inactivate the specific memory B cells such that they can no longer respond to the challenge with 104-BSA. This indicates that the suppression occurs at the level of the specific B cells and is not just an apparent suppression caused by anti-159 antibodies being absorbed to the circulating conjugates and thus being effectively removed from the sera.

To test whether there were in fact fewer B cells responding to 159 in the cured mice than in controls, spleens of sample mice from each group were enumerated for antibody secreting cells by the spot ELISA assay. Table 12 indicates that there was indeed a dramatic difference in the numbers of spleen cells secreting anti-159 antibodies between cured and control animals. In cured animals, the number of spots was negligible whereas high numbers occurred in the controls. This indicates that the administration of $159_{10}dex_{40}$ has caused the functional deletion of 159-specific B cells which can therefore no longer differentiate into antibody secreting cells upon subsequent stimulation with specific antigen.

TABLE 12

| STATUS OF MICE | Ab TITERS TO 159 $OD_{405\ nm}$ | COATING ANTIGEN µg/ml | SPOTS/ WELLS | SEM |
|---|---|---|---|---|
| CURE | 0.219 | 100 | 3 | 1.5 |
| " |  | 50 | 3.7 | 0.88 |
| " |  | 1 | 2.3 | 0.33 |
| " |  | 100 | 2.7 | 0.7 |
| " |  | 50 | 4 | 1.4 |
| " |  | 1 | 1.3 | 0.66 |
| CURE | 0.231 | 100 | 3.3 | 2.1 |
| " |  | 50 | 3.3 | 3.3 |
| " |  | 1 | 1.7 | 1.7 |
| " |  | 100 | 3.3 | 1.2 |
| " |  | 50 | 4 | 1 |
| " |  | 1 | 0 | 0 |
| CONTROL | 2.299 | 100 | 31 | 4.8 |
| " |  | 50 | 21 | 0.6 |
| " |  | 1 | 36 | 5 |
| " |  | 100 | 29 | 1 |
| " |  | 50 | 25 | 3.5 |
| " |  | 1 | ND | ND |
| CONTROL | 2.429 | 100 | 60 | 5.8 |
| " |  | 50 | 55 | 8 |
| " |  | 1 | 49 | 1.1 |
| " |  | 100 | 53 | 2.7 |
| " |  | 50 | 63 | 4.3 |
| " |  | 1 | ND | ND |

Spleens from individual mice were enumerated for cells secreting anti-159 antibodies. Two × $10^5$ cells were added to each well.
ND = not determined Example 12

Treatment of Autoimmune Disease

From the studies described above, the ability of the Immunon technology to suppress ongoing antibody responses to extrinsic antigens is clear. Its applicability to spontaneous autoimmune processes is established by the results that follow.

While there are a number of models of autoimmune disease (experimental autoimmune encephalomyelitis (EAE) for multiple sclerosis, experimental autoimmune myasthenia gravis, collagen induced arthritis for rheumatoid arthritis, etc.) they all suffer from a common paradigmatic problem: the symptom complex exhibited in the experimental animal requires the administration of an extrinsic antigen for the induction of the disease.

In many cases, in order for the symptoms to be maintained, continued, regular administration of antigen is required otherwise the disease process wanes. The relevance and applicability of these models to spontaneously occurring autoimmune processes in man is unclear. There is, however, a model of autoimmune disease in mice (the NZB/NZW mouse model of human systemic lupus erythematosus—murine lupus) that parallels the human with great fidelity. It is spontaneous and does not require the administration of extrinsic antigen for its induction or maintenance; the spectrum of antibodies generated are similar to that seen in human lupus; the disease manifestations are the same with glomerulonephritis being primary; and, the distribution of disease with regard to the sex of the animal is the same (females develop earlier and more severe cases of the disease than males). It is this model of autoimmunity that was chosen to demonstrate the utility of this technology with regard to autoimmune disease.

Animals suffering from murine lupus exhibit the production of both anti-histone as well as anti-DNA antibodies. In preliminary experiments, the distribution of antibodies directed against histone proteins in these mice was shown to be predominantly limited to the amino terminal region of H2B. In fact, in greater than 90% of the mice tested the antigenic region of this protein was found to reside between residues 3 and 12 inclusively

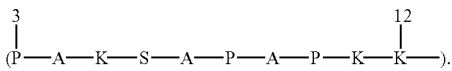

In order to demonstrate the ability to suppress this response, a peptide referred to as CI-0084

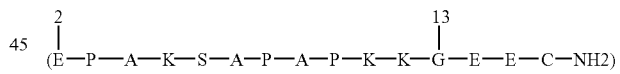

was synthesized and conjugated to 65,000 molecular weight dextran (for details see synthesis section above). This peptide consists of residues 2 through 13 of H2B along with two glutamic acids and a cysteine. The glutamic acids were included in order to render the overall charge on the peptide neutral at physiologic pH and the cysteine was included for the conjugation chemistry. The final constructs were then given to mice with already established antibody titers to both histone and DNA.

Figure 52A:
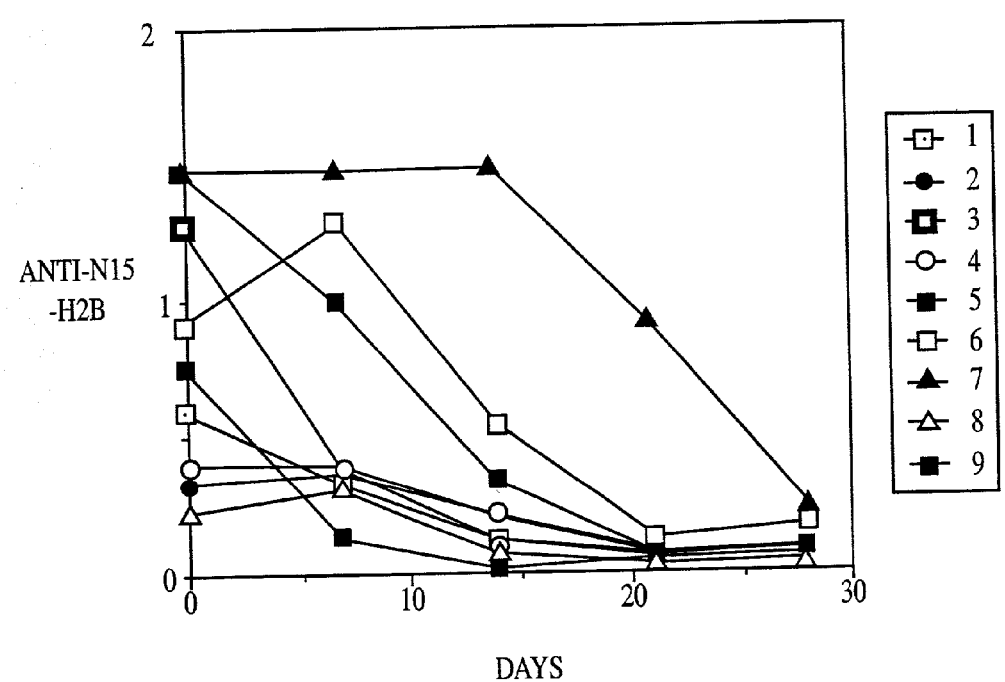
FIG. 52a is experimental group.
Figure 52B:
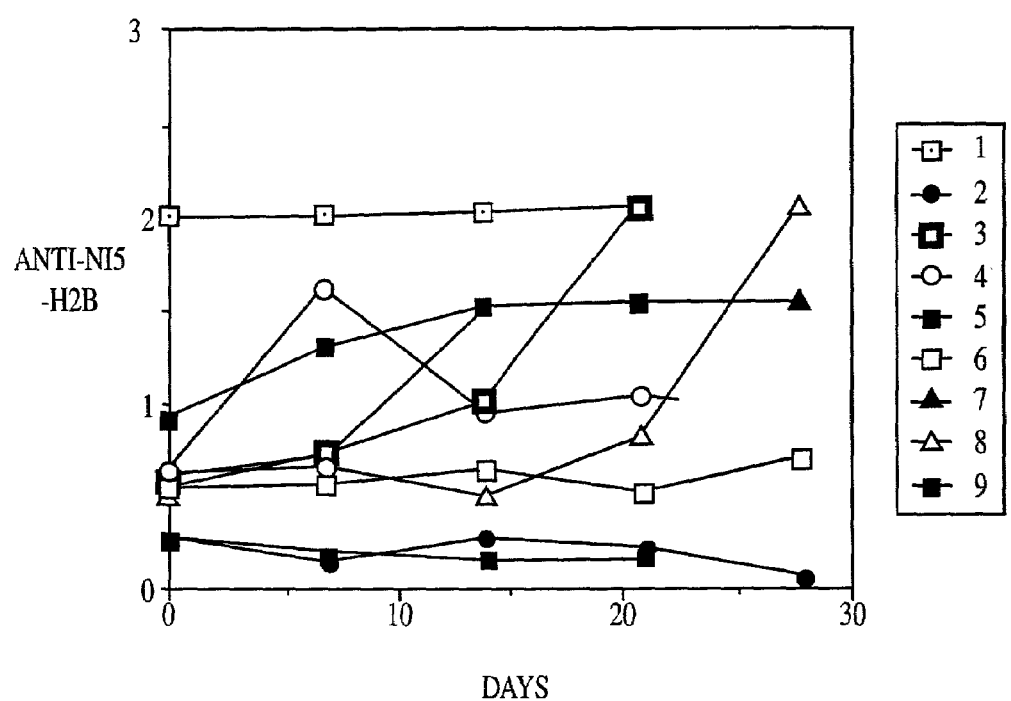
FIG. 52b is control group.
Protocol:
Day 1—1, 10, 100 µg I.V. or 100 µg I.P.
Day 3—200 µg I.P.
Day 9—200 µg I.P.
Day 16—200 µg I.P.
Day 23—200 µg I.P.
Legend: mouse # -□-1; -○-2; -□-3;- -4;-□-5; -□-6;-▲-7;-Δ-8;-□-9.
Figure 53A:
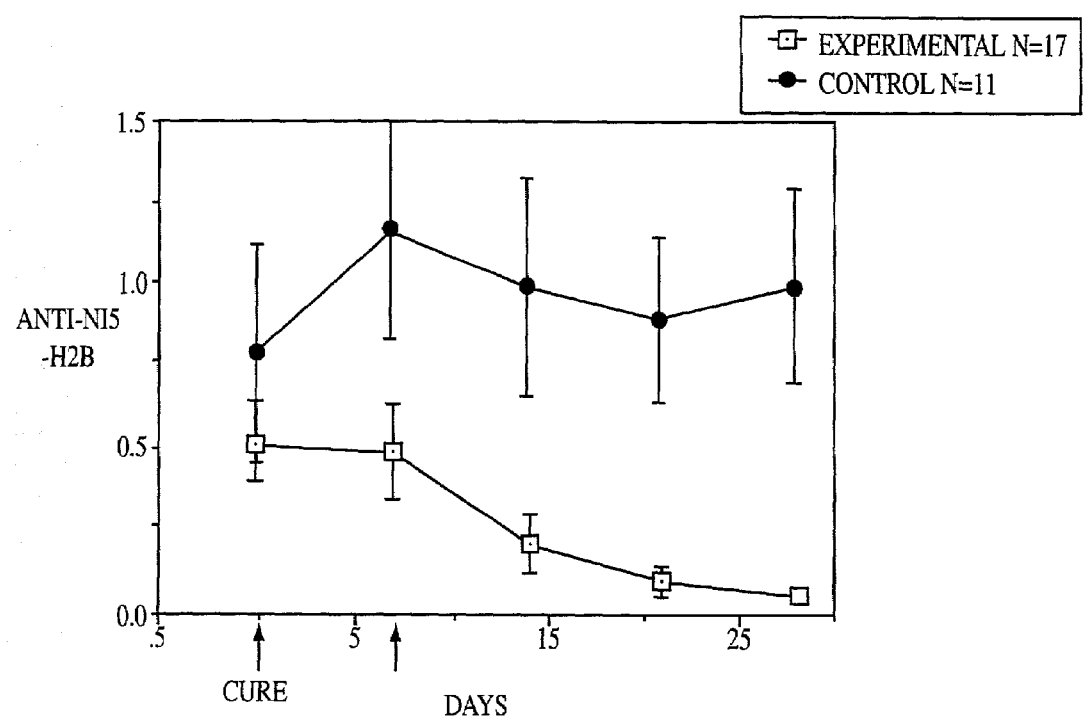
FIG. 53a—Anti-N15-H2B.
Figure 53B:
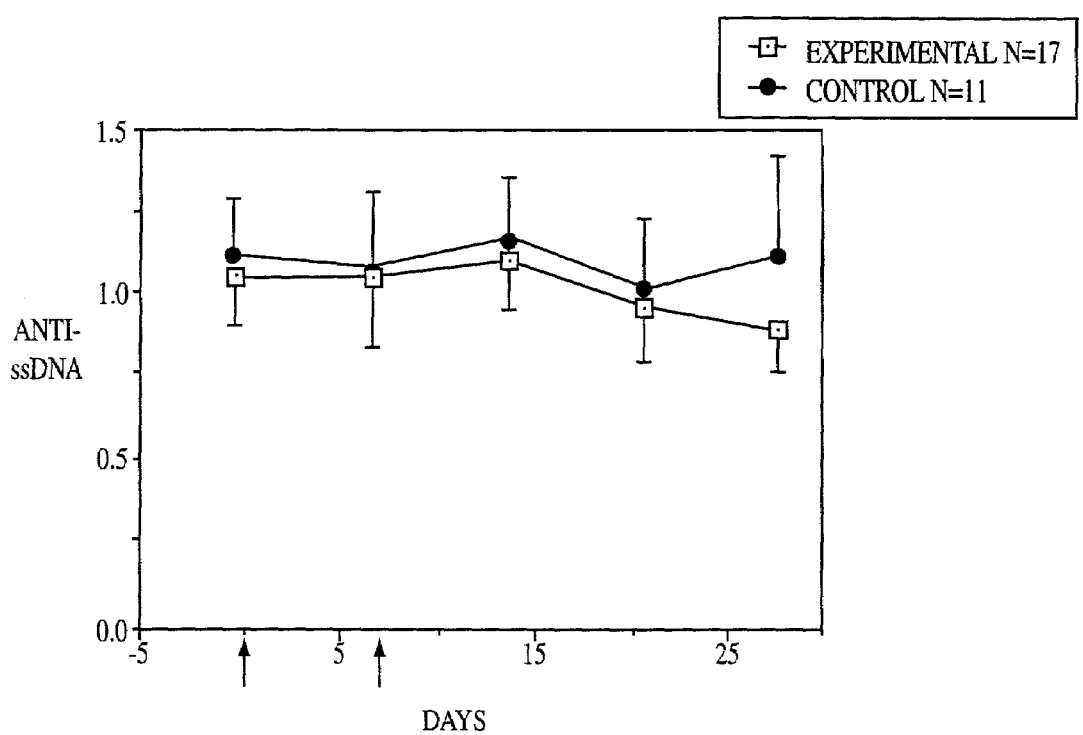
FIG. 53b—Anti-ssDNA.
Legend: Experimental=-□-, N=17; Control=-○-, N=11.

The protocol for conjugate administration is included in FIG. 52. As can be seen, in all of the mice that received the suppressive conjugate anti-histone antibody titers were suppressed to background levels whereas animals that received control conjugates showed no significant changes (or in many cases actual increases) in their anti-histone levels. The specificity of suppression is illustrated in FIG. 53 wherein anti-histone responses are shown to be suppressed while anti-DNA antibody levels are essentially unchanged. In addition to the suppression of circulating antibody titers, enumeration of the B-cell population secreting anti-histone and anti-DNA antibodies in control or "cured" mice was found to parallel the measured antibody levels. Animals treated with the histone specific suppressive conjugates (which reduced circulating antibody titers by greater than 95%) were found to have no detectable cells actively secreting anti-histone antibodies while the control animals had a population of anti-histone antibody secreting cells that were too numerous to quantitate using our standard protocols. Both groups (control and cured) had both equivalent numbers of anti-DNA secreting cells as well as antibody titers. These data clearly illustrate the ability of the Immunon technology to suppress a spontaneous, ongoing autoimmune response on an antigen specific basis.

Example 13

Stimulation and Suppression of Fluorescein Specific T-cell Response by Fluorescein Substituted Soluble Polymers Measurements were made of biologically relevant responses of a T-cell line, after exposure to defined, soluble, polymeric molecules containing haptens capable of binding specifically to the T-cell surface antigen receptors. The responses obtained in these experiments with T-cell lines were found to be in close agreement with the expectations based on the Immunon model. This was true for both the dose-response behavior of the T-cells to individual haptenated polymer preparations and the dose-inhibition behavior observed when stimulatory polymers and non-stimulatory (suppressive) polymers were administrated together. The findings confirmed the fact that the general rules of stimulation and competitive inhibition implicit in the Immunon theory could be applied both to B-cells, which give rise to cells secreting antibody molecules, and to T-cells, which have diverse functions in the regulation of the immune response.

The T-cells used in these experiments were derived from a human T-cell line (Jurkat), which has been widely used as a model of resting peripheral human T-cells. The Jurkat T-cell was transfected with genes encoding both the alpha and the beta polypeptide chains of a fluorescein-specific human T-cell antigen receptor. This transfected Jurkat line was shown to be functional, since it could produce the lymphokine, interleukin-2, upon treatment with conventional T-cell activators, such as a combination of anti-receptor antibody and phorbol ester in the culture medium. When tested for their response to specific antigen, the resulting modified (transfected) Jurkat T-cells were found to bind soluble fluoresceinated polymers directly to the transfected antigen receptors on their cell surface. Appropriate soluble fluoresceinated polymers, i.e., those of high molecular mass and containing a large number of fluorescein epitopes, caused functional activation of the T-cell transfectants. Activation of the T-cells by these soluble polymers was demonstrated by either of two different assays:

1) Production of T-cell interleukin-2.
2) Production of an intracellular calcium flux.

Soluble polymers of smaller molecular mass and substituted with fewer hapten groups did not activate the transfected T-cells, but were nevertheless potent inhibitors of the activation caused by the larger, more heavily haptenated polymers.

Figure 54A:
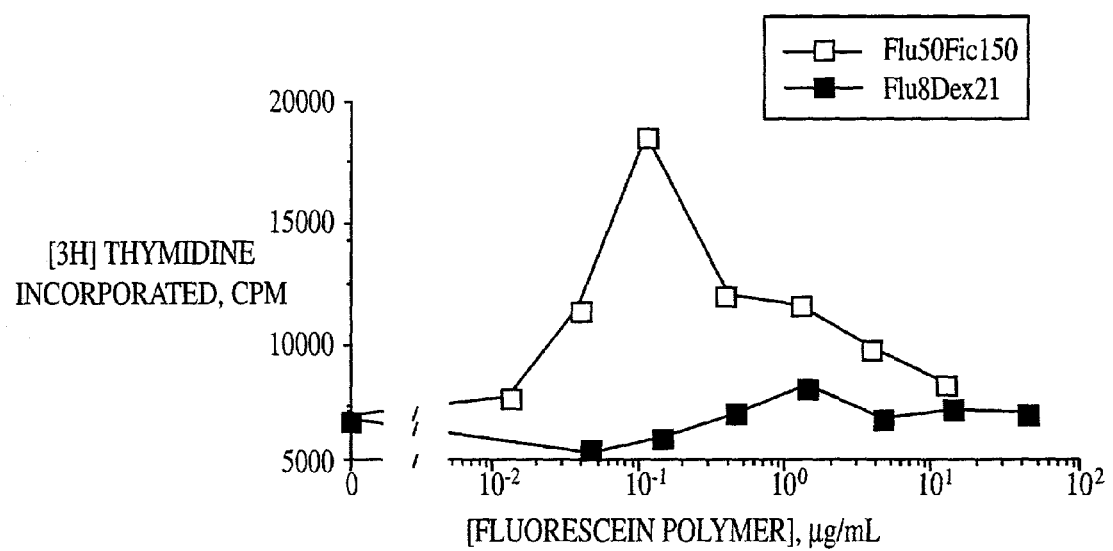
FIG. 54. Activation and inhibition of T-cell interleukin-2 production by soluble fluorescein polymers. Transfected T-cell line 1B2 was treated with phorbol ester, 3 ng per ml, and with various concentrations of soluble fluorescein polymers as indicated in the Figure. After incubation, supernatant solution was removed and assayed for IL-2 by measuring proliferation of an IL-2-dependent cell line, CTLL2. Proliferation of the CTLL2 cells is measured by the incorporation of radioactive thymidine into cellular DNA. In part (a), the T-cell response to two fluorescein polymers of different molecular weight and valence were measured at various concentrations. In part (b), for various indicated concentrations of the stimulatory polymer, the inhibitory polymer was added at four concentrations: none (open squares); 0.48 µg/ml (closed triangles); 4.8 µ/ml (X symbols); and 15 µg/ml (closed squares).

FIG. 54 demonstrates, for a particular pair of fluoresceinated polymers, a representative example of the experimental data described above. FIG. 54(a) shows that a heavily fluorescein-substituted Ficoll preparation of molecular mass over 100 kDa, FL50-Fic150, activated the transfected Jurkat T-cells to produce interleukin-2, as measured by tritiated thymidine incorporation by an IL-2 sensitive cell line. The dose-response stimulation curve is bell shaped, as was observed in the similar mouse B-cell studies previously described. In contrast, the same Figure shows that a fluorescein-substituted dextran, FL8-Dex21, of a similar epitope density but molecular mass well below 100 kDa, was not capable of stimulating the same transfected T-cells at any comparable dose.

Figure 54B:
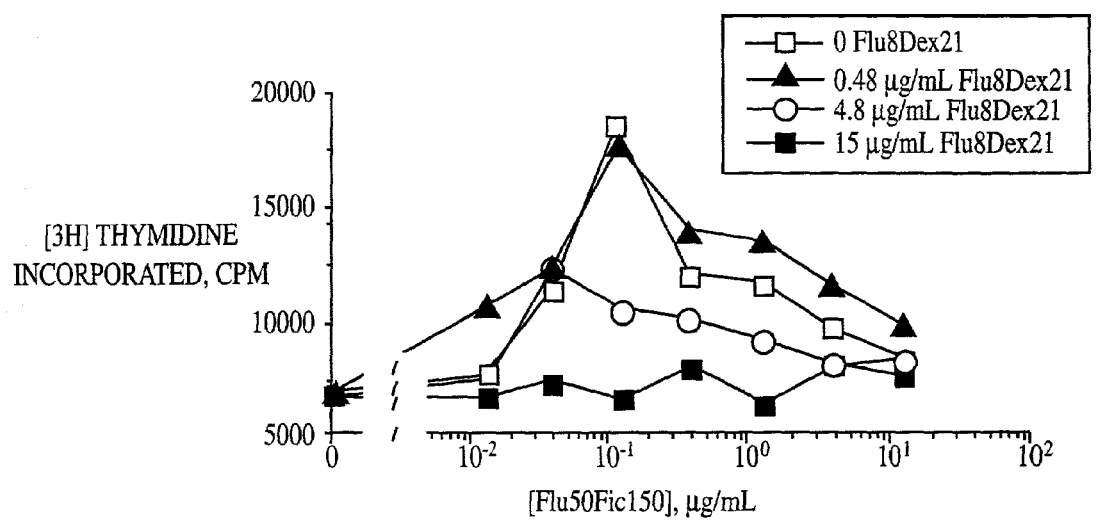

However, FIG. 54(b) shows that when the two polymers were simultaneously added to the transfected T-cells, increasing amounts of the non-stimulatory smaller polymer can be clearly seen to inhibit increasingly the activating ability of the larger, stimulatory, polymer in a dose-dependent manner.

Figure 55:
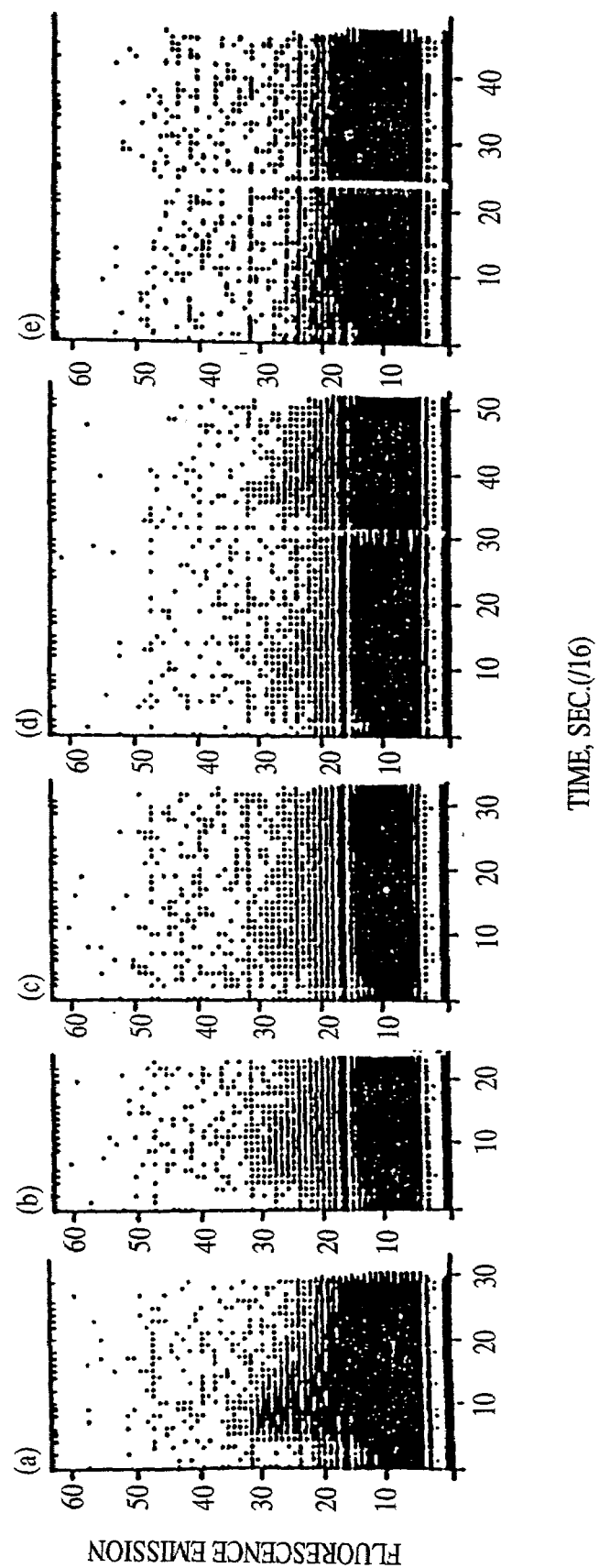
FIG. 55. Activation and inhibition of intracellular calcium flux in T-cells by soluble fluorescein polymers. Transfected T-cells were loaded with the calcium sensitive fluorescent dye, Indo-1 AM (Molecular Probes, Eugene, Oreg.). Fluorescence emission at two wavelengths, 405 and 480 nm, was determined upon excitation at 355 nm for individual cells, using a Coulter MDADS flow cytometer. In the Figure, each dot represents the calcium concentration in a single cell at some instant in time, with time shown in units of 16 seconds on the abscissa. The transfected cells were analyzed for 20 seconds and then various fluorescein polymers were added in the complete absence of phorbol ester or accessory cells. Substantial intracellular calcium concentration rises in at least 10% of the cells were seen when the cells were treated with the stimulatory polymer, FL50-Fic150, at concentrations of 38 µg/ml (a), and 3.8 µg/ml (b), but less calcium flux at 380 µg/ml (c). However, the inhibitory polymer, FL11-Fic46, did not induce any substantial calcium flux at any measured dose, but caused substantial inhibitory effect (d and e). Stimulatory polymer, FL50-Fic150, 38 µg/ml (d) and 3.8 µg/ml (e), was added after a short incubation of the cells with inhibitory polymer. In both cases the calcium flux induced by the stimulatory polymer is almost eliminated.

Similar activation and inhibitory effects were observed when intracellular calcium flux was measured for the transfected T-cells using soluble fluoresceinated polymers, FIG. 55. In this particular example, which is representative of a number of similar measurements, a large highly substituted polymer FL50-Fic150, stimulated the rapid activation of intracellular calcium flux when added at low or moderate dose (a and b), but not at high dose, (c). A non-stimulatory polymer of smaller size but similar epitope density, FL11-Fic46, caused a lack of response by the cells to stimulatory polymer, again demonstrating competitive inhibition (d and e).

The entire contents of all references cited hereinabove are incorporated herein by references.

What is claimed is:

1. A method of making a non-immunogenic construct comprising at least two copies of an epitope of a T-dependent antigen bound to a pharmaceutically acceptable non-immunogenic carrier, which copies bind to a B cell membrane immunoglobulin receptor specific for the epitope but fail to form an immunon, comprising
   (a) providing a non-immunogenic soluble carrier that has been subjected to a preparative sizing technique to remove substantially most high molecular weight soluble carrier molecules, wherein the carrier is not poly (D-Glu/D-Lys), and an epitope molecule of a T-dependent antigen;
   (b) coupling two or more of the epitope molecules to the non-immunogenic soluble carrier that has been subjected to the preparative sizing technique of step (a) to yield a conjugate preparation; and
   (c) subjecting the conjugate preparation to size fractionation to yield a non-immunogenic epitope coupled construct,
   thereby yielding a non-immunogenic construct which is free of high molecular weight immunostimulatory molecules.

2. The method of claim 1, wherein the epitope comprises a peptide epitope.

3. The method of claim 1, wherein the epitope comprises a carbohydrate epitope.

4. The method of claim 1, wherein the epitope comprises a nucleic acid.

5. The method of claim 4, wherein the nucleic acid comprises a phosphorothioate nucleic acid.

6. The method of claim 1, wherein the epitope comprises a glycolipid epitope.

7. The method of claim 1, wherein the epitope is derived from an allergen.

8. The method of claim 1, wherein the epitope is derived from an autoimmune antigen.

9. The method of claim 1, wherein the non-immunogenic carrier comprises a dextran, a Ficoll, a carboxymethylcellulose, a polyvinyl alcohol, a synthetic polymer of D amino acids or a polyacrylamide.

10. The method of claim 1, wherein the non-immunogenic carrier comprises a protein oligomer.

11. The method of claim 10, wherein the protein oligomer comprises an immunoglobulin or albumin.

12. The method of claim 1, wherein after the preparative sizing technique the non-immunogenic carrier has a molecular weight of less than about 100,000 daltons.

13. The method of claim 12, wherein after the preparative sizing technique the non-immunogenic carrier has a molecular weight of less than about 40,000 daltons.

14. The method of claim 1, wherein the preparative sizing technique comprises size exclusion gel chromatography.

15. The method of claim 1, wherein the preparative sizing technique comprises ultrafiltration.

16. The method of claim 1, wherein the copies of the epitope are bound to the non-immunogenic carrier by a spacer molecule.

17. The method of claim 16, wherein the spacer molecule comprises an epsilon amino caproic acid or a delta amino valeric acid.

18. The method of claim 1, wherein the non-immunogenic constmct comprises less than 20 copies of the epitope.

19. The method of claim 1, wherein the non-immunogenic construct is immunosuppressive when administered in pharmacologically effective amounts.

20. The method of claim 19, wherein the non-immunogenic construct suppresses T-cell dependent antibody production.

21. The method of claim 1, wherein the non-immunogenic construct is tolerogenic when administered in pharmacologically effective amounts.

* * * * *

SEQUENCE LISTING

<160> NUMBER OF SEQ ID NOS: 23

<210> SEQ ID NO 1
<211> LENGTH: 33
<212> TYPE: PRT
<213> ORGANISM: Mus musculus

<400> SEQUENCE: 1

Pro Glu Pro Ala Lys Ser Ala Pro Ala Pro Lys Lys Gly Ser Lys Lys
 1               5                  10                  15

Ala Val Thr Lys Ala Gln Lys Lys Asp Gly Lys Lys Arg Lys Ala Tyr

```
                20                  25                  30
Cys

<210> SEQ ID NO 2
<211> LENGTH: 16
<212> TYPE: PRT
<213> ORGANISM: Mus musculus

<400> SEQUENCE: 2

Pro Glu Pro Ala Lys Ser Ala Pro Ala Pro Lys Lys Gly Ser Lys Cys
1               5                   10                  15

<210> SEQ ID NO 3
<211> LENGTH: 16
<212> TYPE: PRT
<213> ORGANISM: Mus musculus

<400> SEQUENCE: 3

Cys Ala Pro Lys Lys Gly Ser Lys Lys Ala Val Thr Lys Ala Gln Lys
1               5                   10                  15

<210> SEQ ID NO 4
<211> LENGTH: 16
<212> TYPE: PRT
<213> ORGANISM: Mus musculus

<400> SEQUENCE: 4

Ala Pro Lys Lys Gly Ser Lys Lys Ala Val Thr Lys Ala Gln Lys Cys
1               5                   10                  15

<210> SEQ ID NO 5
<211> LENGTH: 16
<212> TYPE: PRT
<213> ORGANISM: Mus musculus

<400> SEQUENCE: 5

Cys Lys Ala Val Thr Lys Ala Gln Lys Lys Asp Gly Lys Lys Arg Lys
1               5                   10                  15

<210> SEQ ID NO 6
<211> LENGTH: 10
<212> TYPE: PRT
<213> ORGANISM: Mus musculus

<400> SEQUENCE: 6

Ser Ala Pro Ala Pro Lys Lys Gly Ser Lys
1               5                   10

<210> SEQ ID NO 7
<211> LENGTH: 11
<212> TYPE: PRT
<213> ORGANISM: Mus musculus

<400> SEQUENCE: 7

Lys Ser Ala Pro Ala Pro Lys Lys Gly Ser Lys
1               5                   10

<210> SEQ ID NO 8
<211> LENGTH: 12
<212> TYPE: PRT
<213> ORGANISM: Mus musculus

<400> SEQUENCE: 8

Ala Lys Ser Ala Pro Ala Pro Lys Lys Gly Ser Lys
```

-continued

```
<210> SEQ ID NO 9
<211> LENGTH: 13
<212> TYPE: PRT
<213> ORGANISM: Mus musculus

<400> SEQUENCE: 9

Pro Ala Lys Ser Ala Pro Ala Pro Lys Lys Gly Ser Lys
 1               5                  10

<210> SEQ ID NO 10
<211> LENGTH: 14
<212> TYPE: PRT
<213> ORGANISM: Mus musculus

<400> SEQUENCE: 10

Glu Pro Ala Lys Ser Ala Pro Ala Pro Lys Lys Gly Ser Lys
 1               5                  10

<210> SEQ ID NO 11
<211> LENGTH: 7
<212> TYPE: PRT
<213> ORGANISM: Mus musculus

<400> SEQUENCE: 11

Glu Pro Ala Lys Ser Ala Pro
 1               5

<210> SEQ ID NO 12
<211> LENGTH: 9
<212> TYPE: PRT
<213> ORGANISM: Mus musculus

<400> SEQUENCE: 12

Glu Pro Ala Lys Ser Ala Pro Ala Pro
 1               5

<210> SEQ ID NO 13
<211> LENGTH: 11
<212> TYPE: PRT
<213> ORGANISM: Mus musculus

<400> SEQUENCE: 13

Glu Pro Ala Lys Ser Ala Pro Ala Pro Lys Lys
 1               5                  10

<210> SEQ ID NO 14
<211> LENGTH: 14
<212> TYPE: PRT
<213> ORGANISM: Mus musculus

<400> SEQUENCE: 14

Glu Pro Ala Lys Ser Ala Pro Ala Pro Lys Lys Gly Glu Cys
 1               5                  10

<210> SEQ ID NO 15
<211> LENGTH: 15
<212> TYPE: PRT
<213> ORGANISM: Mus musculus

<400> SEQUENCE: 15

Glu Pro Ala Lys Ser Ala Pro Ala Pro Lys Lys Gly Glu Glu Cys
 1               5                  10                  15
```

```
<210> SEQ ID NO 16
<211> LENGTH: 25
<212> TYPE: PRT
<213> ORGANISM: Mus musculus
<220> FEATURE:
<221> NAME/KEY: VARIANT
<222> LOCATION: (1)...(25)
<223> OTHER INFORMATION: Xaa = O-ACA/Pro

<400> SEQUENCE: 16

Cys Xaa Ala Asp Ser Gly Glu Gly Asp Phe Leu Ala Glu Gly Gly
 1               5                  10                  15

Val Arg Gly Pro Arg Val Val Val Tyr
            20                  25

<210> SEQ ID NO 17
<211> LENGTH: 15
<212> TYPE: PRT
<213> ORGANISM: Mus musculus

<400> SEQUENCE: 17

Glu Pro Ala Lys Ser Ala Pro Ala Pro Lys Lys Gly Glu Glu Cys
 1               5                  10                  15

<210> SEQ ID NO 18
<211> LENGTH: 11
<212> TYPE: PRT
<213> ORGANISM: Mus musculus

<400> SEQUENCE: 18

Glu Ala His Ala Glu Ile Asn Glu Ala Gly Arg
 1               5                  10

<210> SEQ ID NO 19
<211> LENGTH: 37
<212> TYPE: PRT
<213> ORGANISM: Mus musculus

<400> SEQUENCE: 19

Cys Gly Ala Gly Glu Ala Leu Ala Glu Ala Leu Ala Glu Ala Leu Ala
 1               5                  10                  15

Glu Ala Leu Ala Glu Ala Leu Ala Glu Ala Leu Ala Gly Ala Gly Arg
            20                  25                  30

Gly Asp Ser Pro Ala
            35

<210> SEQ ID NO 20
<211> LENGTH: 24
<212> TYPE: PRT
<213> ORGANISM: Mus musculus

<400> SEQUENCE: 20

Glu Ala Leu Ala Glu Ala Leu Ala Glu Ala Leu Ala Glu Ala Leu Ala
 1               5                  10                  15

Glu Ala Leu Ala Glu Ala Leu Ala
            20

<210> SEQ ID NO 21
<211> LENGTH: 33
<212> TYPE: PRT
<213> ORGANISM: Mus musculus

<400> SEQUENCE: 21
```

```
                                            -continued

Glu Ala Leu Ala Glu Ala Leu Ala Glu Ala Leu Ala Glu Ala Leu Ala
  1               5                  10                  15

Glu Ala Leu Ala Glu Ala Leu Ala Gly Ala Gly Arg Gly Asp Ser Pro
                 20                  25                  30

Ala

<210> SEQ ID NO 22
<211> LENGTH: 10
<212> TYPE: PRT
<213> ORGANISM: Mus musculus

<400> SEQUENCE: 22

Pro Ala Lys Ser Ala Pro Ala Pro Lys Lys
  1               5                  10

<210> SEQ ID NO 23
<211> LENGTH: 15
<212> TYPE: PRT
<213> ORGANISM: Mus musculus

<400> SEQUENCE: 23

Glu Pro Ala Lys Ser Ala Pro Ala Pro Lys Lys Gly Glu Glu Cys
  1               5                  10                  15
```